United States Patent [19]
Fleming

[11] Patent Number: 5,658,322
[45] Date of Patent: Aug. 19, 1997

[54] BIO-ACTIVE FREQUENCY GENERATOR AND METHOD

[75] Inventor: Janet E. Fleming, San Diego, Calif.

[73] Assignee: Regeneration Technology, Tijuana, Mexico

[21] Appl. No.: 541,182

[22] Filed: Oct. 11, 1995

[51] Int. Cl.$^6$ .................................................... A61N 1/18
[52] U.S. Cl. ................................. 607/50; 607/66; 607/67
[58] Field of Search ................................. 607/50, 66, 67, 607/142; 331/34, 179; 327/105–107

[56] References Cited

U.S. PATENT DOCUMENTS

| | | | |
|---|---|---|---|
| 4,255,790 | 3/1981 | Hondeghem | 364/487 |
| 4,738,250 | 4/1988 | Fulkerson et al. | 607/50 |
| 4,895,154 | 1/1990 | Bartelt et al. | 607/50 |
| 4,919,139 | 4/1990 | Brodard | 607/66 |
| 5,048,523 | 9/1991 | Yamasawa et al. | 607/66 |
| 5,285,781 | 2/1994 | Brodard | 607/66 |
| 5,447,526 | 9/1995 | Karsdon | 607/39 |

FOREIGN PATENT DOCUMENTS 003234A  8/1985  Denmark .................. 607/50

*Primary Examiner*—William E. Kamm
*Assistant Examiner*—Carl H. Layno
*Attorney, Agent, or Firm*—Gilliam, Duncan & Harms

[57] ABSTRACT

A system and method for generating bio-active frequencies. Such generated frequencies are very precise and are accurate within 0.001 Hz. The frequencies are used to advantage in health science applications such as killing microorganisms and viruses and enhancing tissue regeneration and may be used in various commercial and industrial applications, such as food processing. A specific precise frequency synthesizer is controlled by a programmable control that instructs the synthesizer to generate a specific precise frequency or a series of precise frequencies. A keyboard is actuable by a user to select a specific frequency or sequence of frequencies or a preprogrammed series of frequencies. Depending upon the specific frequency being generated, a circuit gates the generated signal ON or OFF with a predetermined determinable periods being selected for such ON/OFF periods. Immediately prior to initiation of a specific precise frequency signal a warning auditory signal is made to alert a user of the device and the frequency signal is gradually increased at a predetermined rate from zero to a predetermined level controllable by a user. A display indicates information representative of the specific frequencies selected and the period of running of each. Application electrodes for the device are disclosed as well as an indicator as to whether the electrodes are in proper contact with a subject.

39 Claims, 23 Drawing Sheets

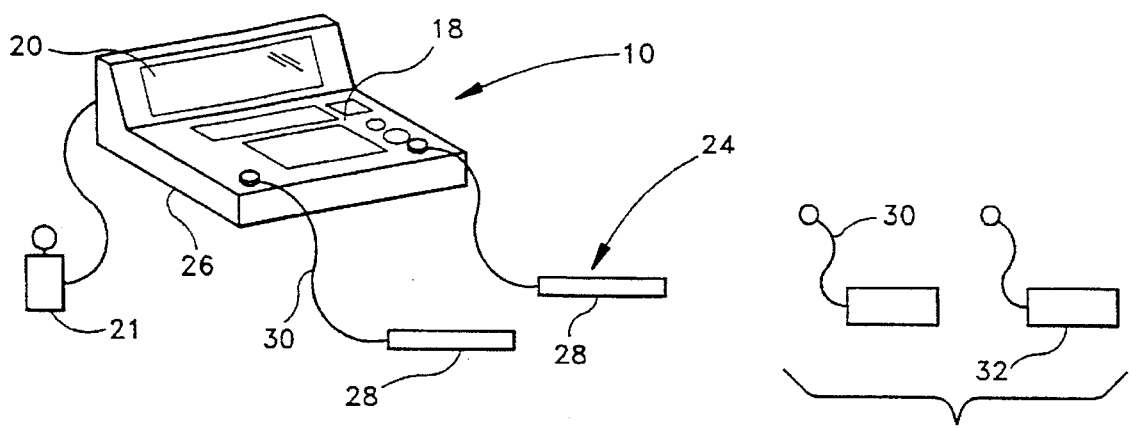
FIG. 9
FIG. 10
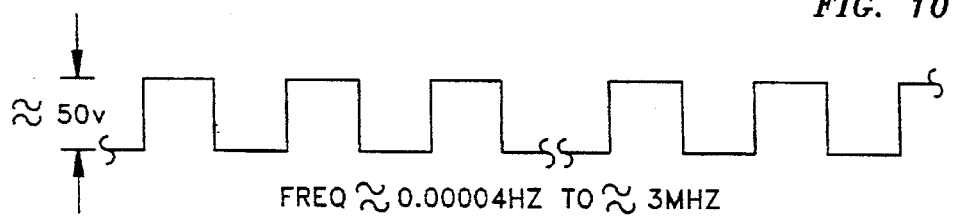
FIG. 11
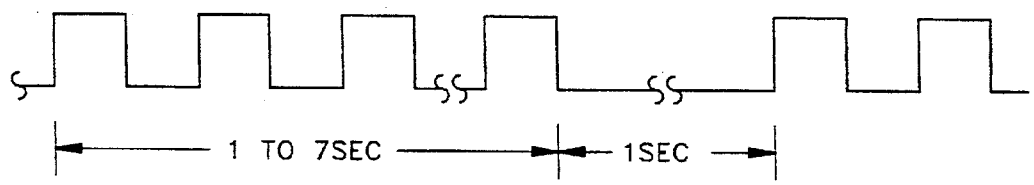
FIG. 12
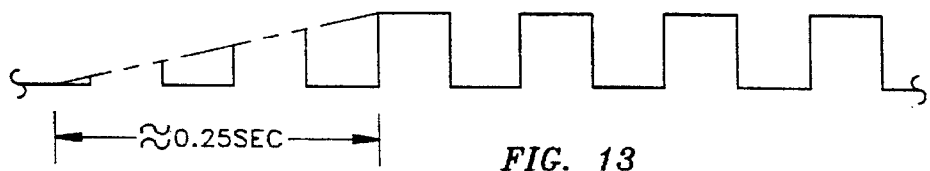
FIG. 13
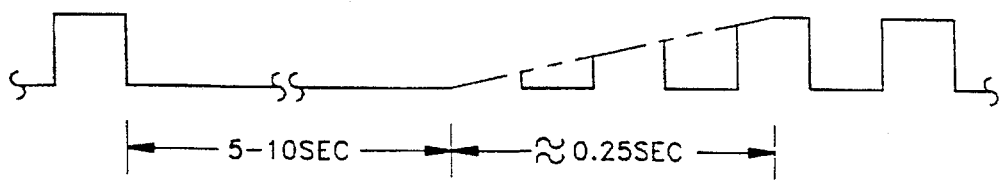
FIG. 14

BIO-ACTIVE FREQUENCY GENERATOR AND METHOD

BACKGROUND OF THE INVENTION

1. Field of the Invention

This invention relates in general to an improvement in the field of devices for health science applications and other applications that include industrial control of microorganisms, and more particularly but not by way of limitation, to a device and method for generating with extremely high accuracy specific frequencies and sequences of specific frequencies that are particularly adapted for killing micro-organisms and viruses and for enhancing metabolic tissue functions in mammals.

2. Description of the Prior Art

The use of electrical stimulation in heath science applications involving humans has long been known and it has been reported that one of the earliest attempts to suppress organic pain and other neurophysical effects utilizing electrical stimulation may have occurred as early as 2,000 years ago, when it was reported that gout could apparently be successfully treated by placing a diseased extremity in a tub of water containing electric eels. Apparently, attempts were also made to treat headaches with a similar treatment.

Since that early time many devices and methods have been devised to use electricity and electromagnetic fields for medical purposes. For example, U.S. Pat. No. 4,598,713 was issued on Jul. 8, 1986 to Achim Hansjurgens et al for ELECTROSTIMULATION THERAPY DEVICE AND METHOD. This device relates to electrostimulation therapy of the electrical interference therapy type. In this therapy medium frequency voltages with frequencies in the range of a few thousand Hz are applied over at least two circuits, each with one pair of electrodes, which differ from each other by a low frequency range of from a few to a few hundred Hz, so that stimulations, and thereby therapeutically effective oscillations called beats, occur with correspondingly low frequency in the body. This device stores data representative of signals having predetermined instantaneous value variations with time. These values are used to construct electrical signals having curves that represent both the medium frequency output signals and the interference beats with sufficient stability of frequency that makes possible small spacing of adjacent frequencies.

U.S. Pat. No. 5,304,486 issued to Donald C. Chang for a METHOD OF AND APPARATUS FOR CELL PORATION AND CELL FUSION USING RADIO FREQUENCY ELECTRICAL PULSE relates to the poration and fusion of cells using high-power radio frequency electrical pulses. A power function generator applies a continuous AC electrical field and/or a high-power pulsed radio frequency electrical field to induce cell congregation by the process of dielectrophoresis which porates or fuses the cells. The method can be used with a variety of cells including animal cells, human cells, plant cells, protoplasts, lipsosomes, bacteria and yeasts. It also can introduce into such cells a large variety of chemical agents including DNA, RNA, antibodies, proteins, drugs and inorganic chemicals.

U.S. Pat. No. 4,917,092 was issued on Apr. 17, 1990 to G. A. Todd et al for TRANSCUTANEOUS NERVE STIMULATOR FOR TREATMENT OF SYMPATHETIC NERVE DYSFUNCTION. This nerve stimulator is to be used in T.E.N.S. (Transcutaneous Electrical Nerve Stimulation) therapy and provides for generating pulses with the pulse width, rate, and amplitude being modulated over a modulation cycle to stimulate the autonomic and central nervous system of a patient. A sympathetic nerve dysfunction is treated with a low frequency of pulses, while through the strength-duration modulation at higher pulse rates the patient's nociceptors are addressed so that the autonomic nervous system is stimulated for more than 5% of the amount of time as said central nervous system.

U.S. Pat. No. 4,509,520 was issued on Apr. 9, 1985 for an ELECTRICAL STIMULATING APPARATUS and is directed toward stimulating osteogenesis in a living body. The device is a light weight, low drain, battery operated stimulating instrument to carried by a patient during treatment for applying a high frequency alternating current treatment signal to the skin of the patient according to a treatment program and creating a record of such treatment. A stimulating signal of 60 Hz is generated and has a square or sine waveform.

U.S. Pat. No. 4,305,390 issued to M. R. Swartz for a METHOD FOR GENERATING OXYGEN IN AN EXCITED ELECTRONIC STATE AND INACTIVATION OF MICROORGANISMS and contemplates a system for inactivation of such microorganisms and their products, for example, Herpes simplex viruses by superposition of a component such as methylene blue plus light, oxygen and electricity. This system generates the superoxide radical anion and consequently hydrogen peroxide and the hydroxyl radical, both of which enter into the inactivation process.

U.S. Pat. No. 4,428,050 discloses a tanning device for monitoring time integrated exposure to UV radiation and indicating the achievement of preselected dosages of such exposure for obtaining a desired tan.

U.S. Pat. No. 4,535,775 discloses a method healing bone fractures non-invasively by applying to electrodes coupled to the skin of a living body in the vicinity of a bone fracture an alternating voltage having a wave form that is symmetrical with respect to the axis, a frequency in the range of 20–100 KHZ and a value in the range from about 2 to 10 volts peak to peak.

It has also been found that each species of life has its own unique electronic signature. Accordingly, every micro-organism has its own specific molecular oscillation pattern. It has also been found that if such micro-organism is subjected to a specific precise electrical frequency signal at a predetermined amplitude it is possible to inactivate or kill such micro-organism while not effecting any other micro-organism or tissue. While the process by which such inactivation of the micro-organism takes place when subjected to such precise frequency signal is not fully understood, it is apparent that such procedure is efficacious. Also, it has been found that subjecting the tissue of a mammal to a specific precise frequency signal does enhance tissue regeneration. For present purposes, such precise frequency signals are termed bio-active frequencies and it is apparent that a need exists for a device to generate upon command such precise bio-active frequency electrical signals for desired applications which may include health science applications and other industrial and commercial applications. Such a device would be able to generate specific bio-active frequency signals selected by a user of the device as well as to generate specific bio-active frequency signals that were preprogrammed into the device for selection by a user for a particular health science, industrial or commercial application. It is believed that such need is fulfilled by the present invention and the particular method employed by it to generate such bio-active frequencies as desired.

SUMMARY OF THE INVENTION

Briefly stated, the present invention contemplates and method to generate an electrical output signal having a precise frequency and particularly adapted for use in applications for which it may be particularly suited such as health science applications and other applicable industrial and commercial applications. The particular precise frequency signal generated may be a single frequency signal that is generated for a predetermined period of time or may be a first frequency signal that is generated for a predetermined period of time and which is then followed by a second or further frequency signals that are also generated for predetermined periods of time or may be a beat frequency created by heterodyne action of two carrier frequences as in an optional antenna array designed for use with this device. The precise frequency output signal may also be a continuous signal or may be interrupted for predetermined periods of time to provide a signal that is ON for a controllable period of time and then OFF for a constant recurring interval. The continuous precise frequency signal is believed to be particularly useful in the inactivation of micro-organisms while the frequency signal that is periodically (pulsed) interrupted is believed to be useful for tissue regeneration purposes and metabolic tissue functions for mammals.

The system of the present invention for generating such precise frequency output signals includes a frequency synthesizer means that is a response to a control signal to generate a precise frequency output signal. A programmable control means is coupled to the frequency synthesizer means and is operated to generate a determinable control signal selected by a user of the system for application to the frequency synthesizer means. The control means may be programmed to generate single precise frequency signal or it may be programmed to generate a sequence of control signals for generation of a series of frequency output signals, such sequence of precise frequency output signals may be termed the SEQUENCE programs. The control means may also be preprogrammed so that a particular command from a user of the system is operative to generate a predetermined sequence of precise frequency output signals, such series of precise frequency output signals may be termed the AUTO programs. The programmable control means also stores instructions associated with a particular specific frequency which indicate whether the precise frequency output signal is to be generated as a continuous signal or whether periodic interruption intervals are to be interposed into the signal. If an interruption interval is to be interposed into the precise frequency output signal, that interval is determined to be generally around one second in duration. The period that the precise frequency output signal is ON between intervals is controllable by a user of the system and will be from about one to seven seconds.

An output circuit is coupled to the frequency synthesizer means for generation of an amplified output signal that is coupled to application means for use in a particular desired application such as health science applications and other selected industrial and commercial applications. In the instance of the application of the amplified output signal to mammals, the amplitude of the output signal may be adjusted for maximum efficiency while avoiding undue discomfort to the subject of such signal. Further, the present invention provides circuitry associated with the output signal that provides for the amplified output signal, at the start of each specific frequency, to gradually have its amplitude increased from zero to a predetermined amplification level at a predetermined rate to avoid any inadvertent momentary discomfort to a recipient of the amplified output signal in a "soft" start of each precise frequency output signal. In addition, a no output signal interval is interposed at the start of each frequency signal and between each precise frequency signal in a sequence of frequencies so that an audio circuit may be activated to provide an auditory alert to the recipient of the amplified output signal of the ensuing change of the frequency signal.

The system is provided with a keyboard means for actuation by a user of the system to select a specific precise frequency output signal, or a sequence of precise frequency output signals or a preprogrammed sequence of frequency signals, the AUTO mode. Two separate controls are also actuable to determine amplitude level of the output signal and the ON pulse time of a precise frequency output signal that is subject to intervals of no signal. A display means is associated with the keyboard means to display information relating to actuation of the keyboard and to status of a particular output signal then being generated.

The amplified output signal generated by the output means is applied to a subject such as a mammal by spaced electrode means that are placed in direct contact with the subject in a predetermined manner. The electrode means may take several forms according to that Judged most applicable for the particular application. For example, the object to be treated may also be immersed in a vat or container of a conductive fluid medium such as water, which may or may not contain electrolytes, to improve conduction of the electrical precise frequency output signal therethrough. In an application such as food processing, the use of a conductive fluid medium is particularly well suited since it permits amplification of the precise frequency signal to a high levels that achieves greater penetration than is safe or easily tolerated by living subjects such as mammals.

The precise frequency output signal is generated in a manner to ensure maximum stability and is stable to at least 0.001 Hz. Such generated precise frequency output signal is also accurate to 0.000001 Hz at the lower service range of frequencies as will be set forth hereinafter.

The system of the present invention, other than the application means, is housed in a separable enclosure which is not intended to be opened by unauthorized parties. A security circuit is provided which is operative upon opening of the enclosure to disable the system.

Other features and attendant advantages of the present invention will become apparent to those skilled in the art from a reading of the following detailed description constructed in accordance with the accompanying drawings and wherein:

BRIEF DESCRIPTION OF THE DRAWINGS

FIG. 9 is a simplified perspective of the invention and an exemplary application electrode means.

FIG. 10 is a simplified perspective of an alternative application electrode means.

FIG. 11 is a waveform of one specific precise frequency output signal.

FIG. 12 is a waveform illustrating the gated ON/OFF intervals of a frequency output signal.

FIG. 13 is a waveform illustrating a soft start for the initiation of a frequency output signal.

FIG. 14 is a waveform illustrating the interval between two successive frequency output signals and the soft start of the succeeding frequency signal.

DETAILED DESCRIPTION OF THE DRAWINGS

Figure 1:
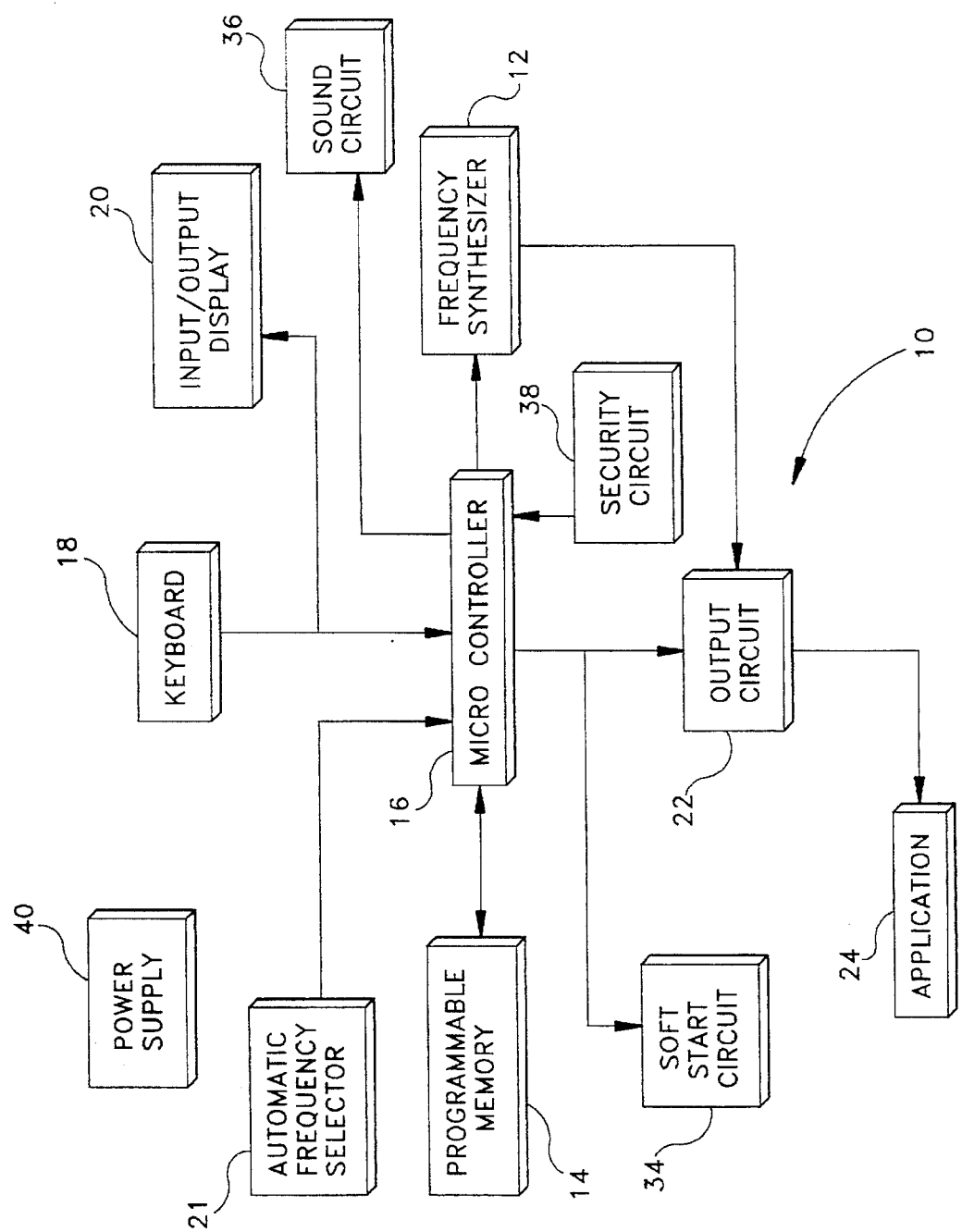
FIG. 1 is a block diagram a system constructed in accordance with a preferred embodiment of the present invention.

Referring now to the drawings in detail and in particular to FIG. 1, the reference character 10 generally designates a system constructed in accordance with a preferred embodiment of the invention. The system 10 includes a frequency synthesizer means 12 that is responsive to a control signal to generate a precise frequency output signal having a frequency selected from a range of about 0.00004 Hz. to 3 Mhz. The output waveform of the frequency synthesizer preferably has a square wave output with a 50% duty cycle. The frequency generated by the frequency synthesizer is very precise since for some health science applications a variance of 1 Hz. is acceptable while for other health science applications a variance of no more that 0.001 Hz. would be desirable. Accordingly, it is desirable for the frequency range of 0.00004 Hz to 3 Mhz. contemplated to be generated by the synthesizer 12 such that a variance of less than 0.001 Hz be achieved, which requirement is met by the frequency synthesizer means shown in greater detail hereinafter. A representation of such precise frequency output signal is seen in FIG. 11.

A programmable memory control means 14 is coupled to the frequency synthesizer circuit 12 through a suitable micro controller means 16 to instruct the frequency synthesizer 12 as to the specific frequency output signal the frequency synthesizer 12 is to generate. The control means 14, which will be seen in greater detail hereinafter, includes EPROM and EEPROM integrated circuits, and is operable to store control signals representative of a single specific precise frequency output signal and a sequence of precise frequency output signals. The control signals for the programmable storage means 14 for the generation of a particular frequency or frequencies may be generated by the actuation of a keyboard means 18 which is coupled through the micro controller 16 to the programmable memory control means Actuation of the keyboard means, which is seen most clearly in FIG. 2, by a user permits the selection of a single specific frequency and the selection of a sequence of predetermined frequencies. In addition, a user of the system 10 may also choose a predetermined sequence of specific frequencies by choosing only one number which is representative of a number of such predetermined frequencies that are arranged in a predetermined sequence.

Figure 2:
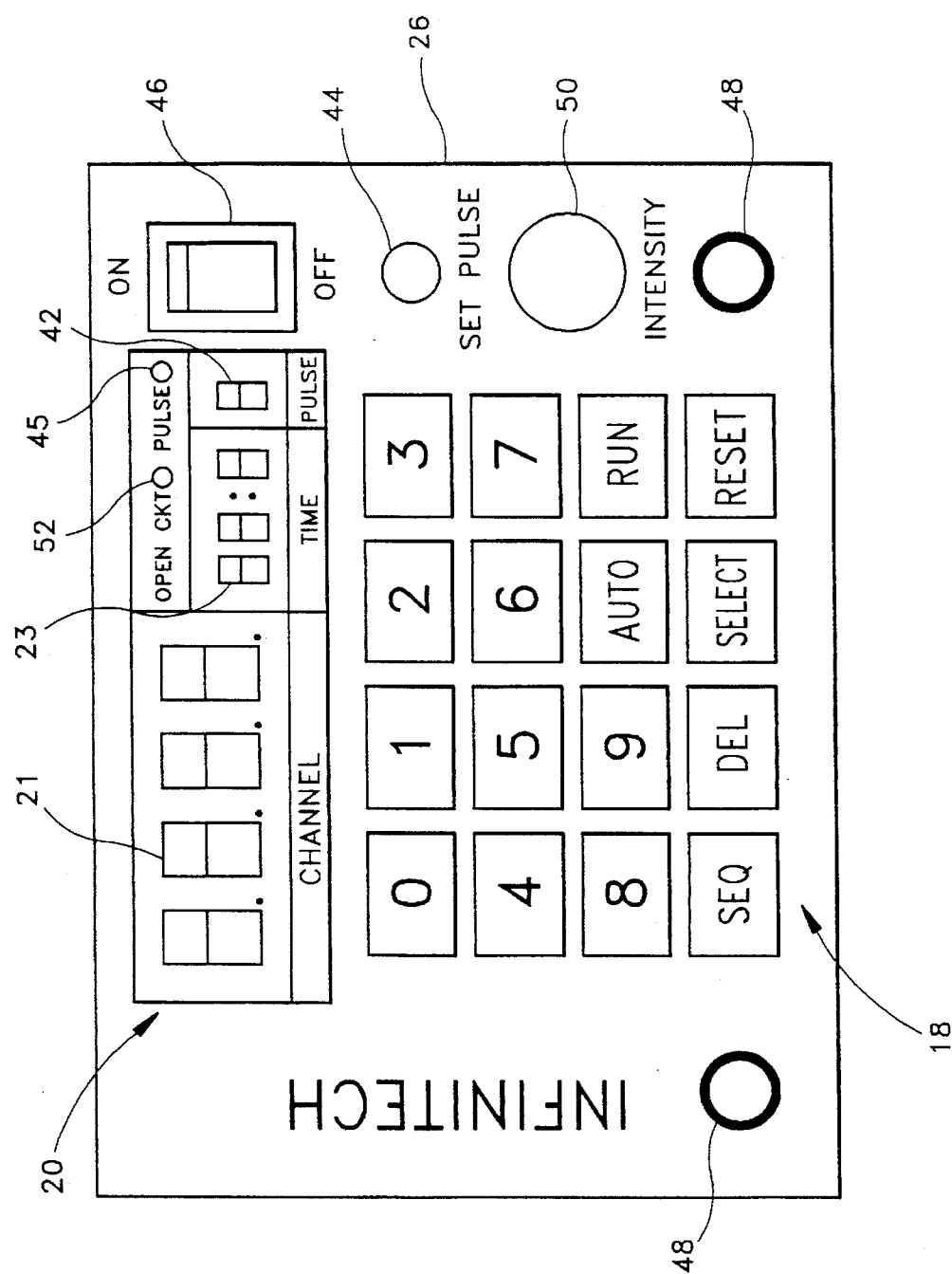
FIG. 2 a perspective of the display and keyboard of the block diagram of FIG. 1.
Figure 3A:
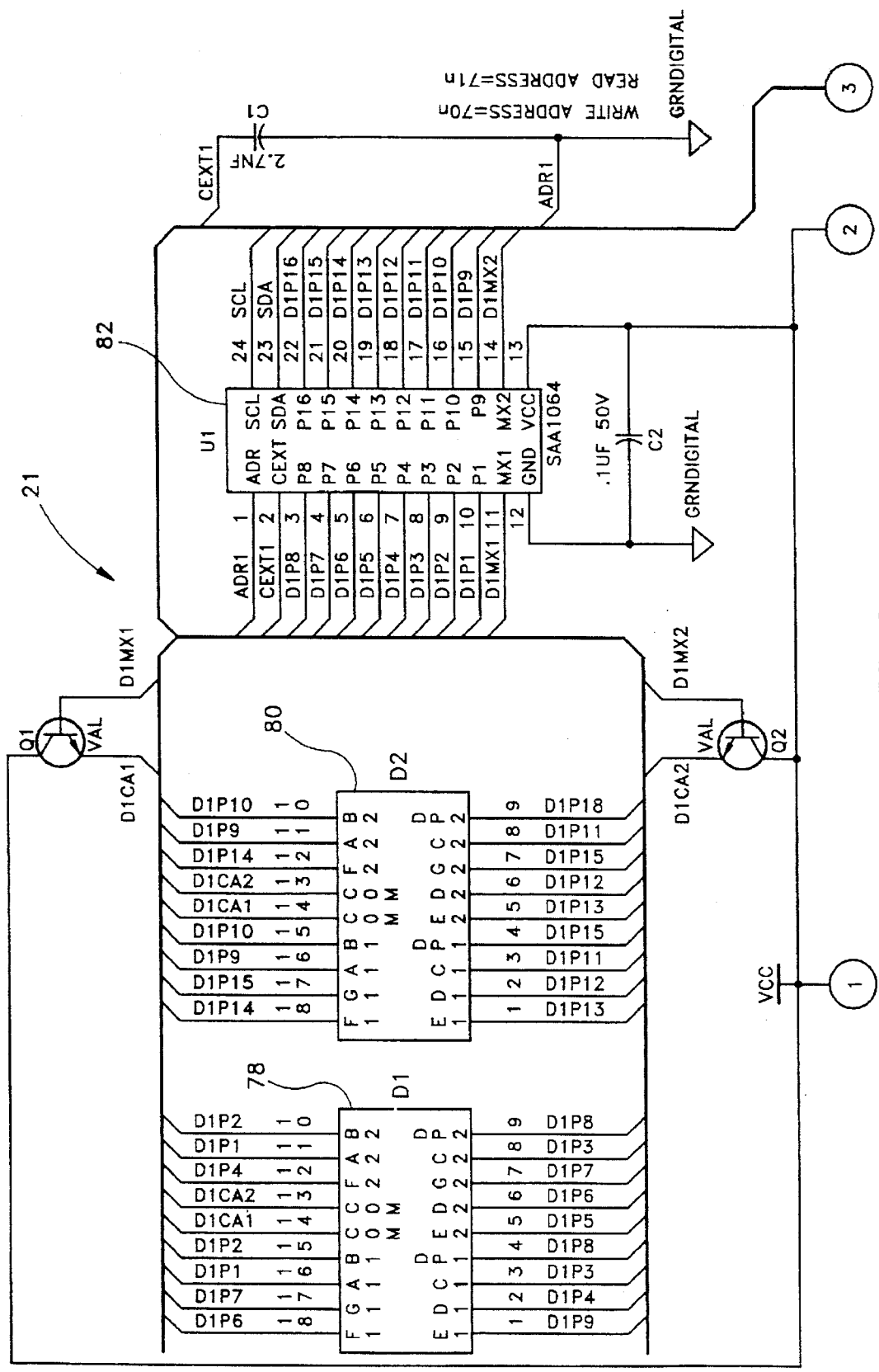
FIG. 3a, 3b, 3c, 3d, 3e, and 3f combined is a schematic diagram of primarily the keyboard and display aspects of the system.
Figure 3B:
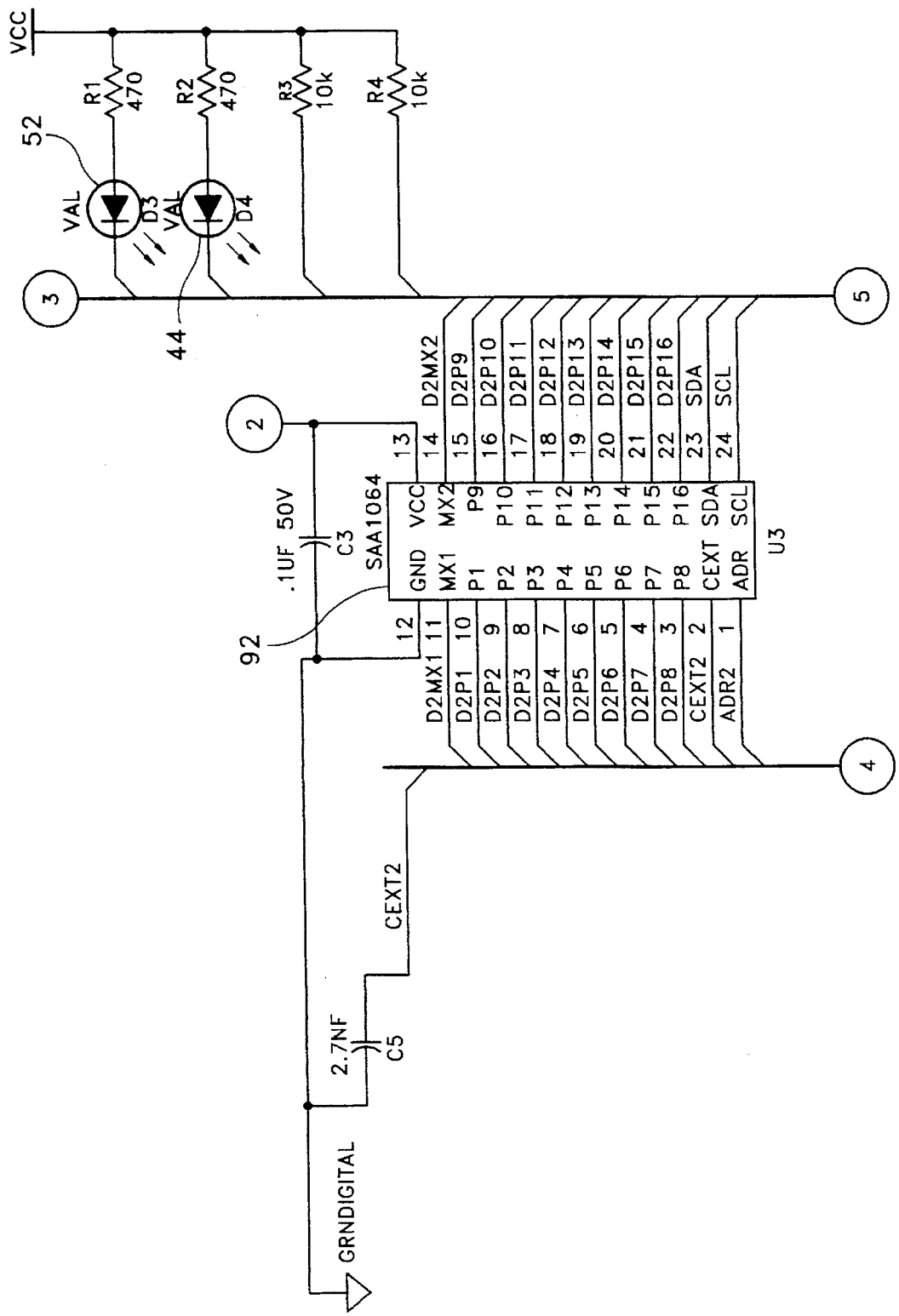
Figure 3C:
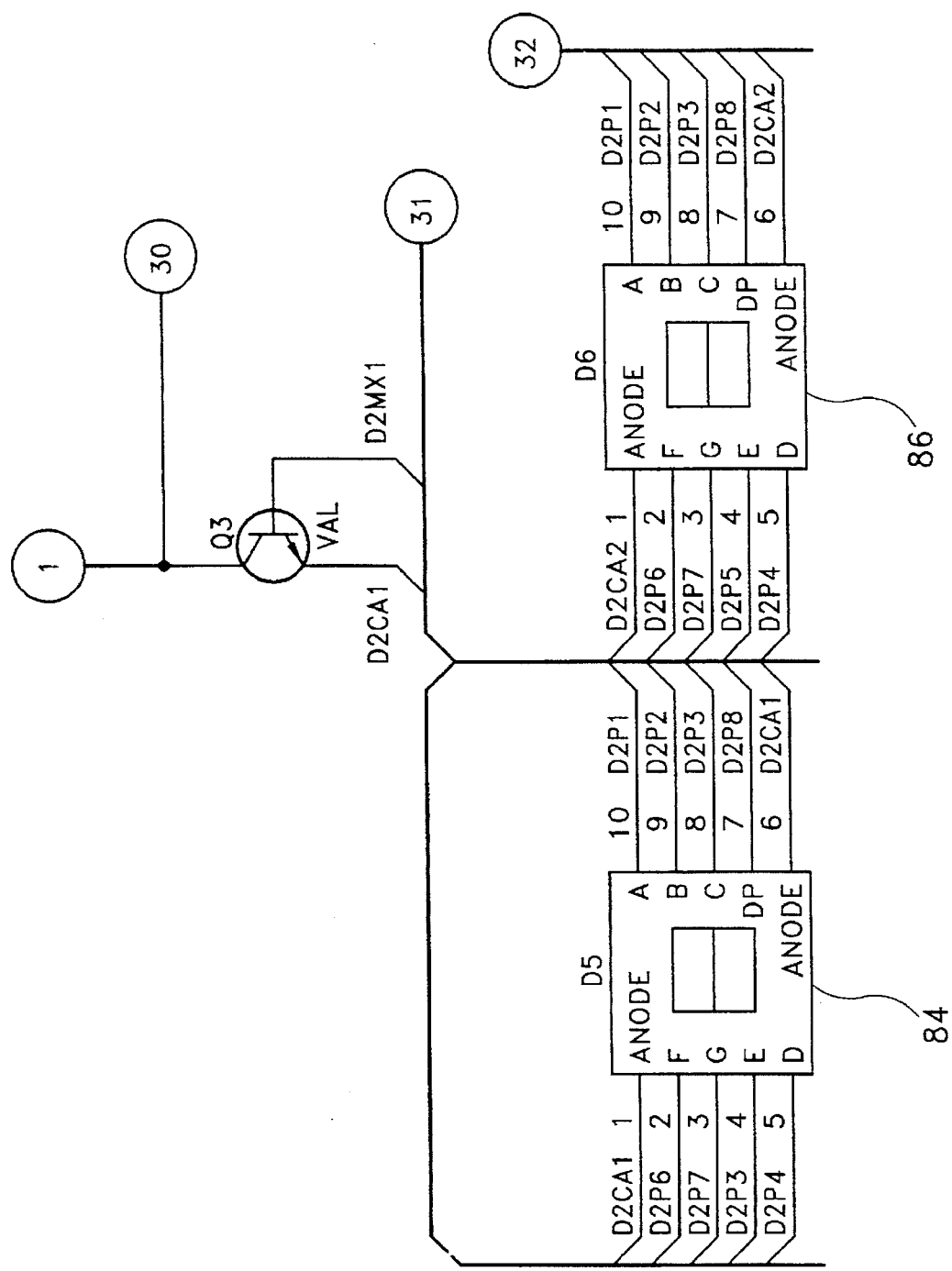
Figure 3D:
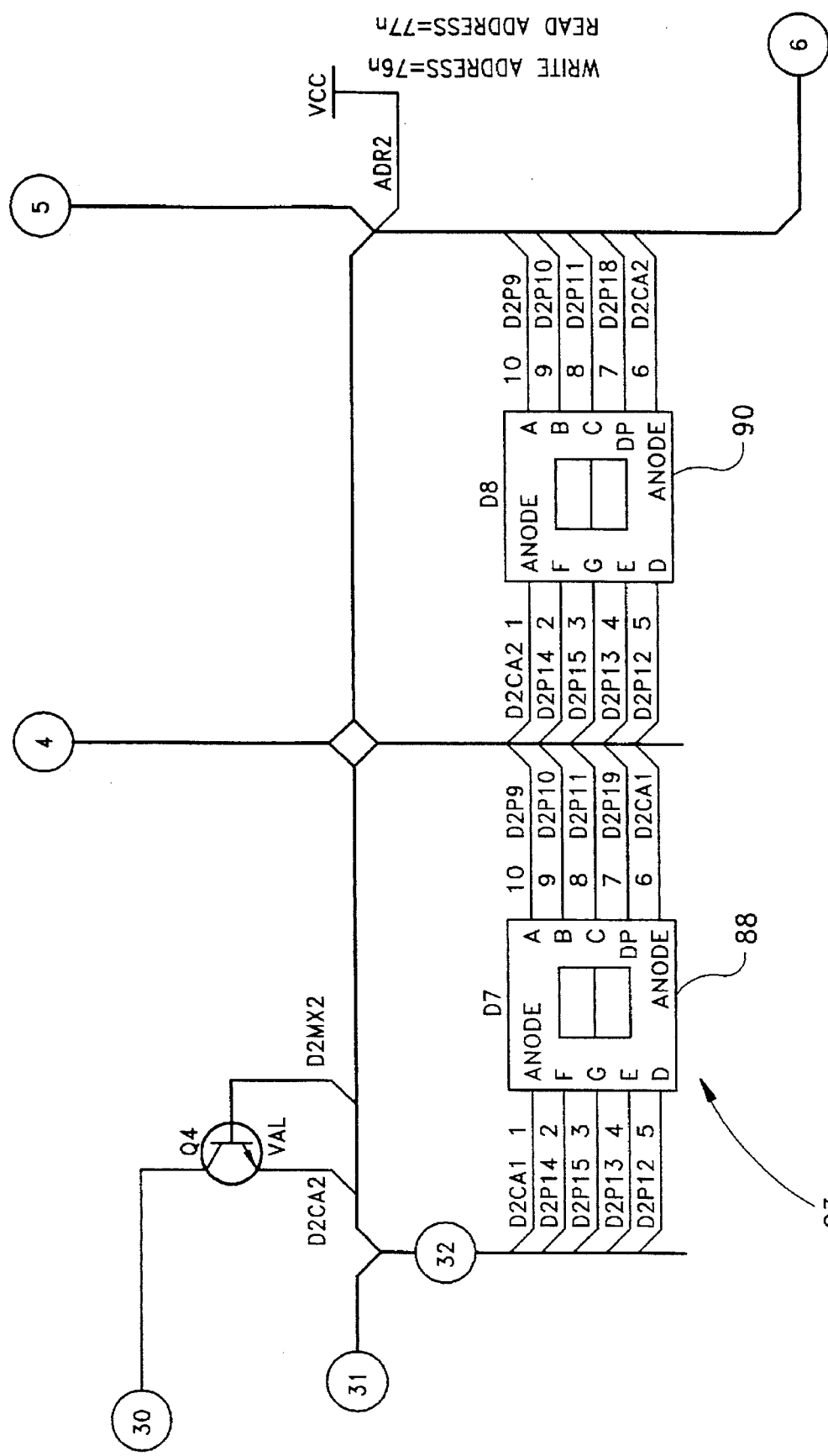
Figure 3E:
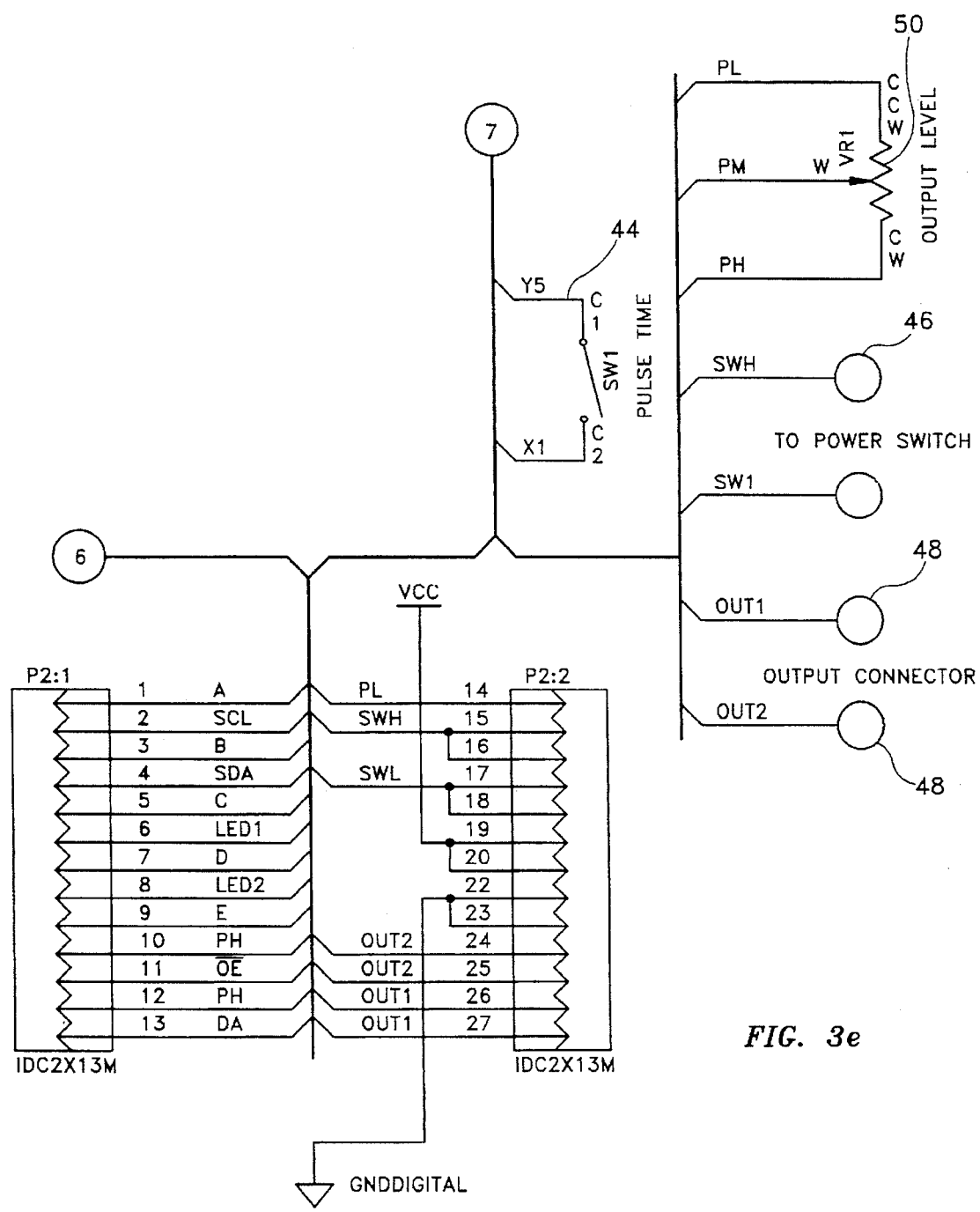
Figure 3F:
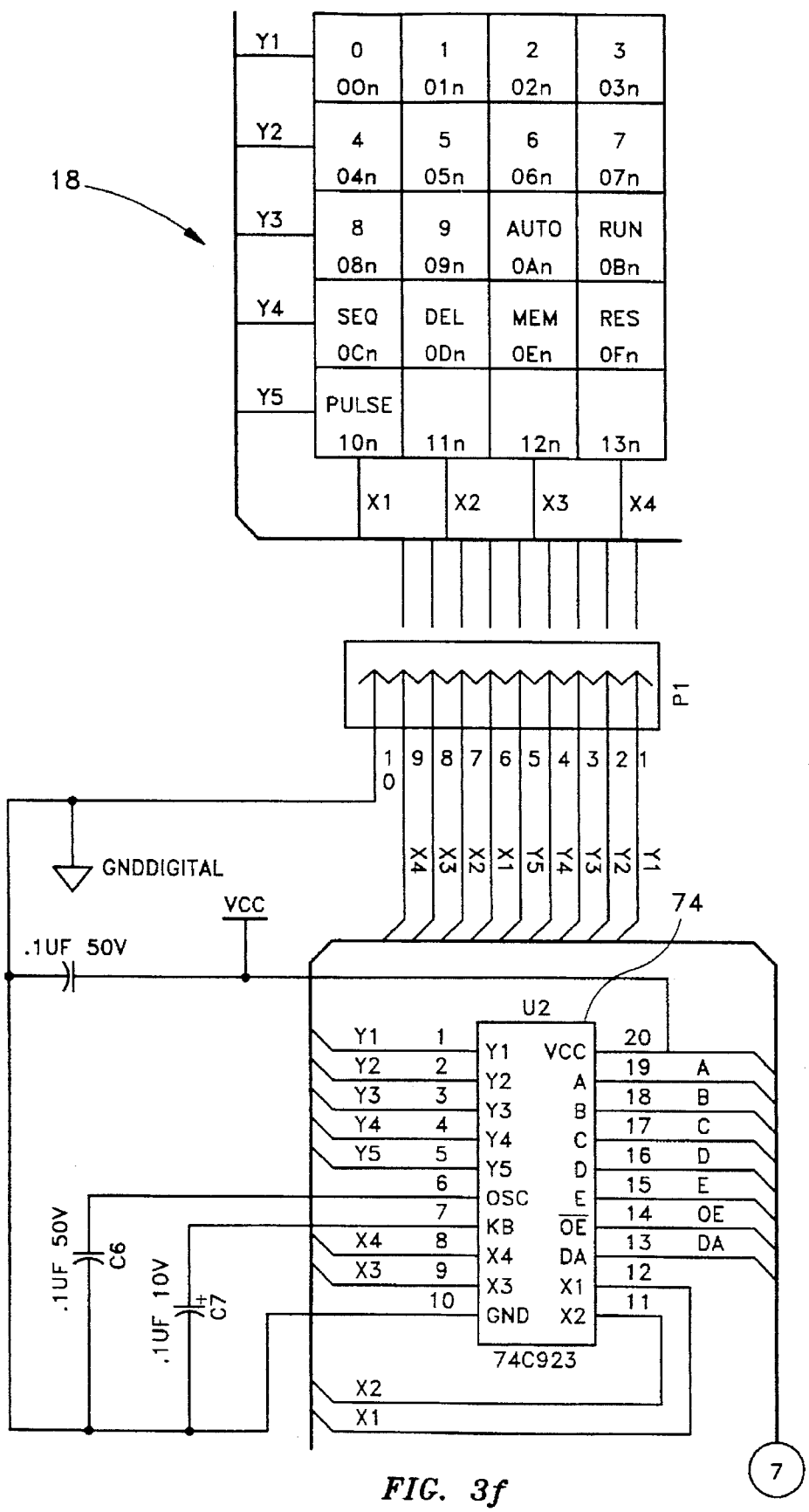
Figure 4A:
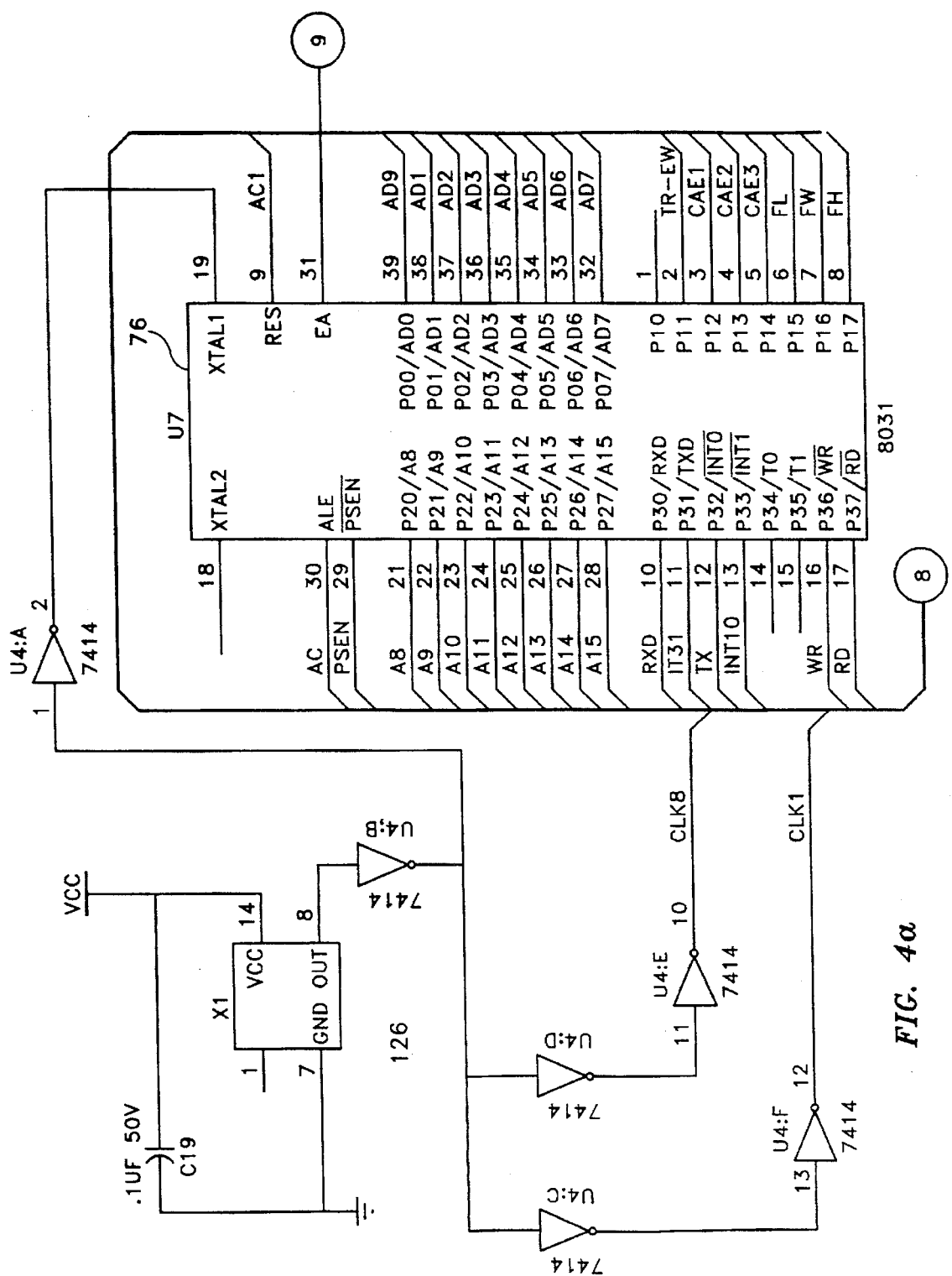
FIG. 4a, 4b, 4c, 4d, 4e, 4f, 4g, 4h and 4i combined is a schematic diagram of primarily the micro controller and programmable control portions of FIG. 1.
Figure 4B:
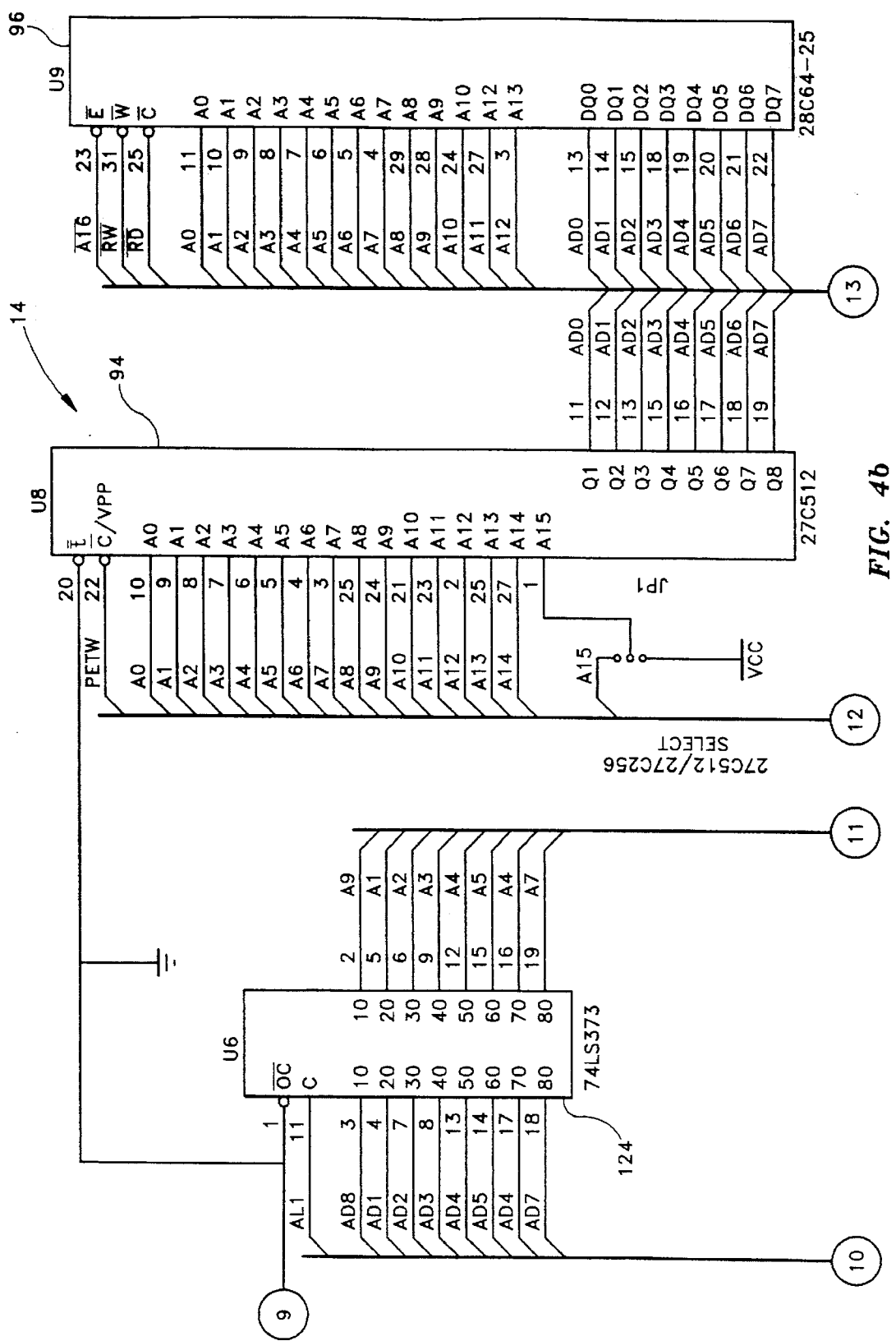
Figure 4C:
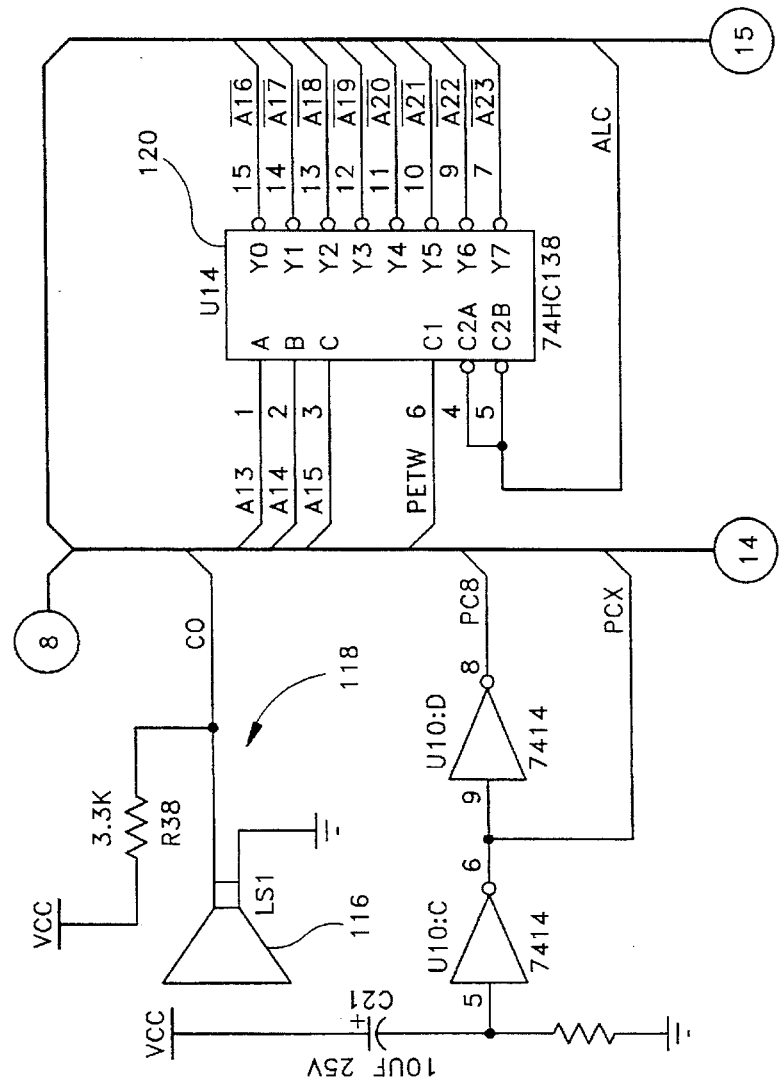
Figure 4D:
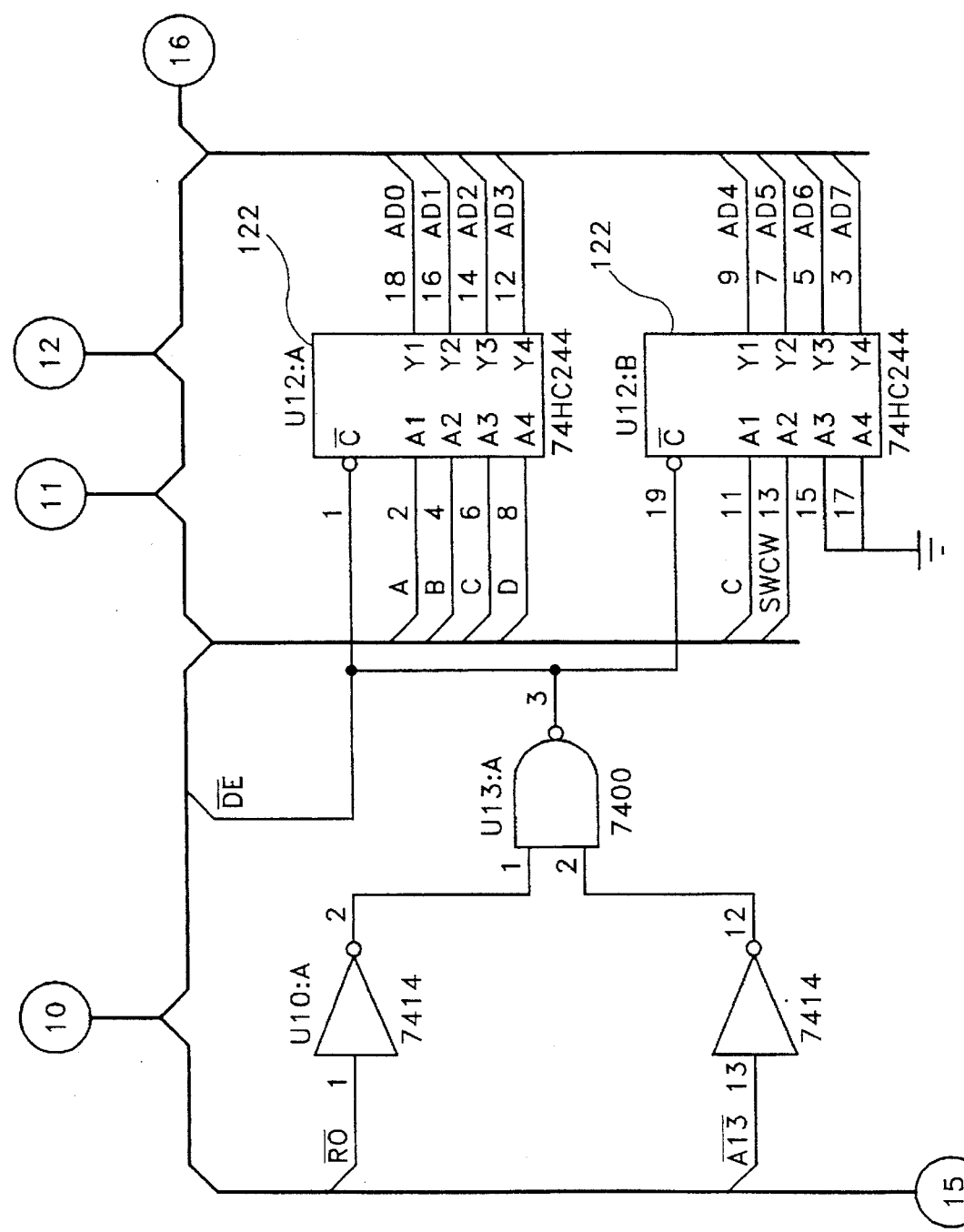
Figure 4E:
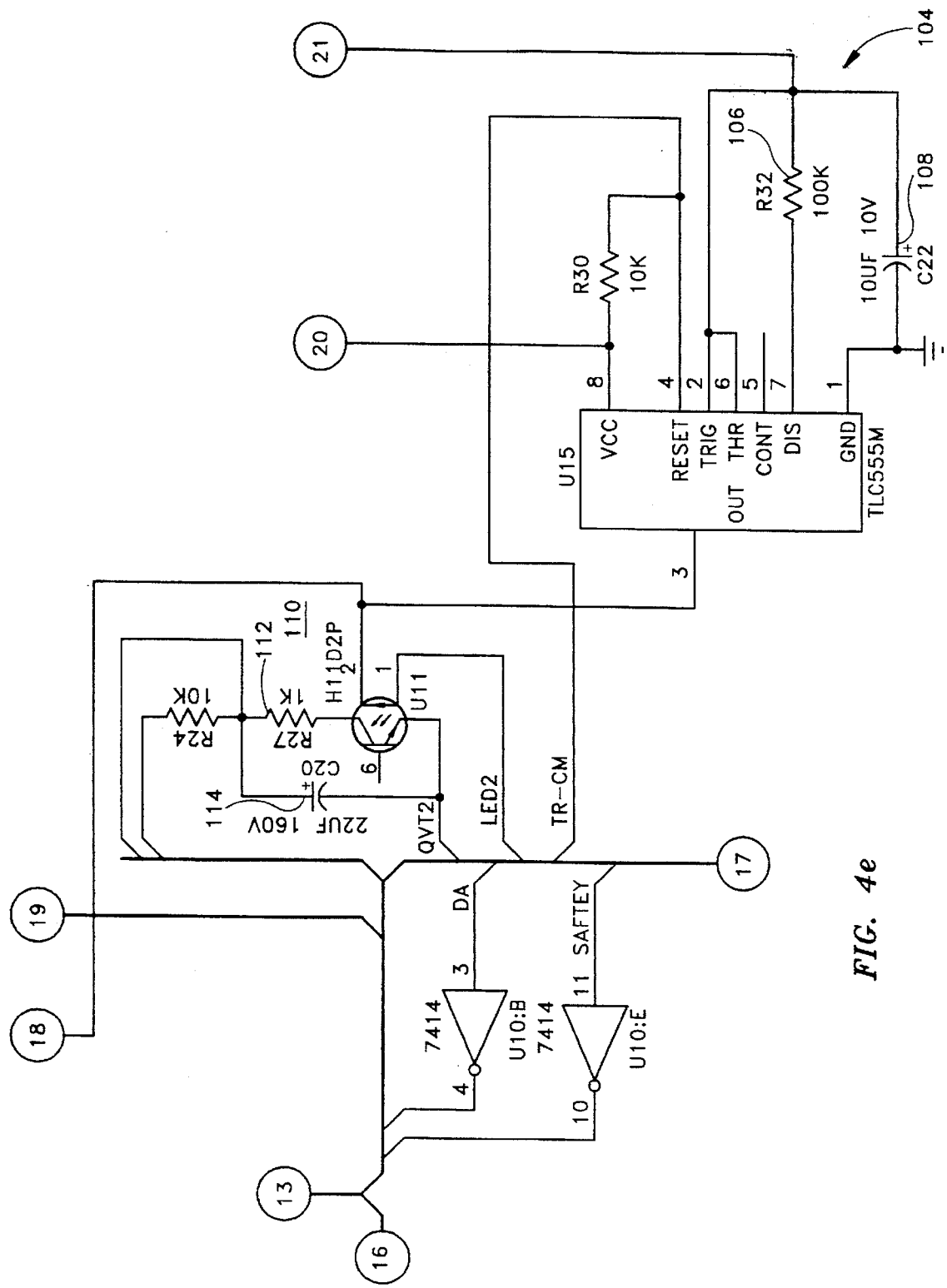
Figure 4F:
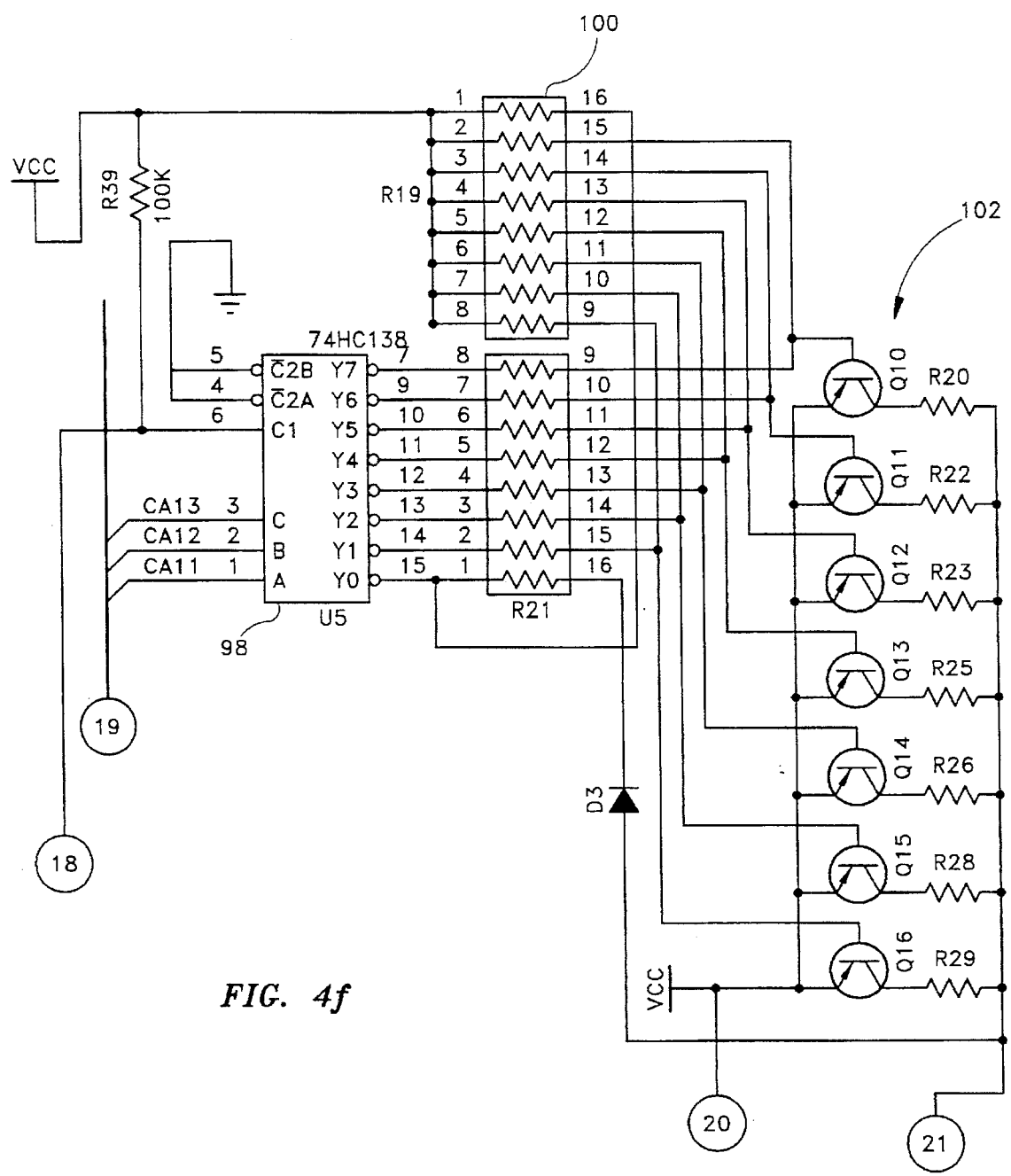
Figure 4G:
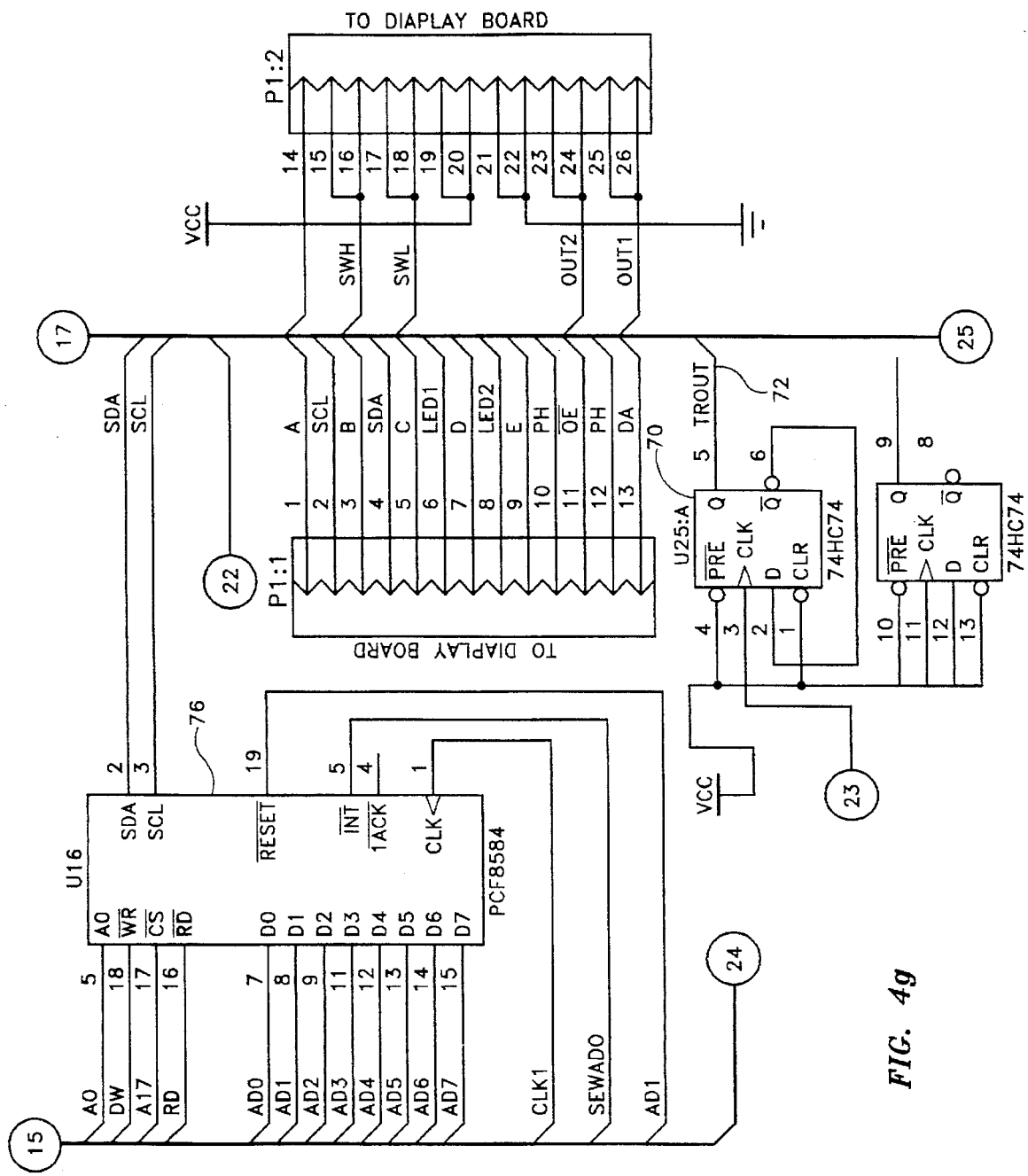
Figure 4H:
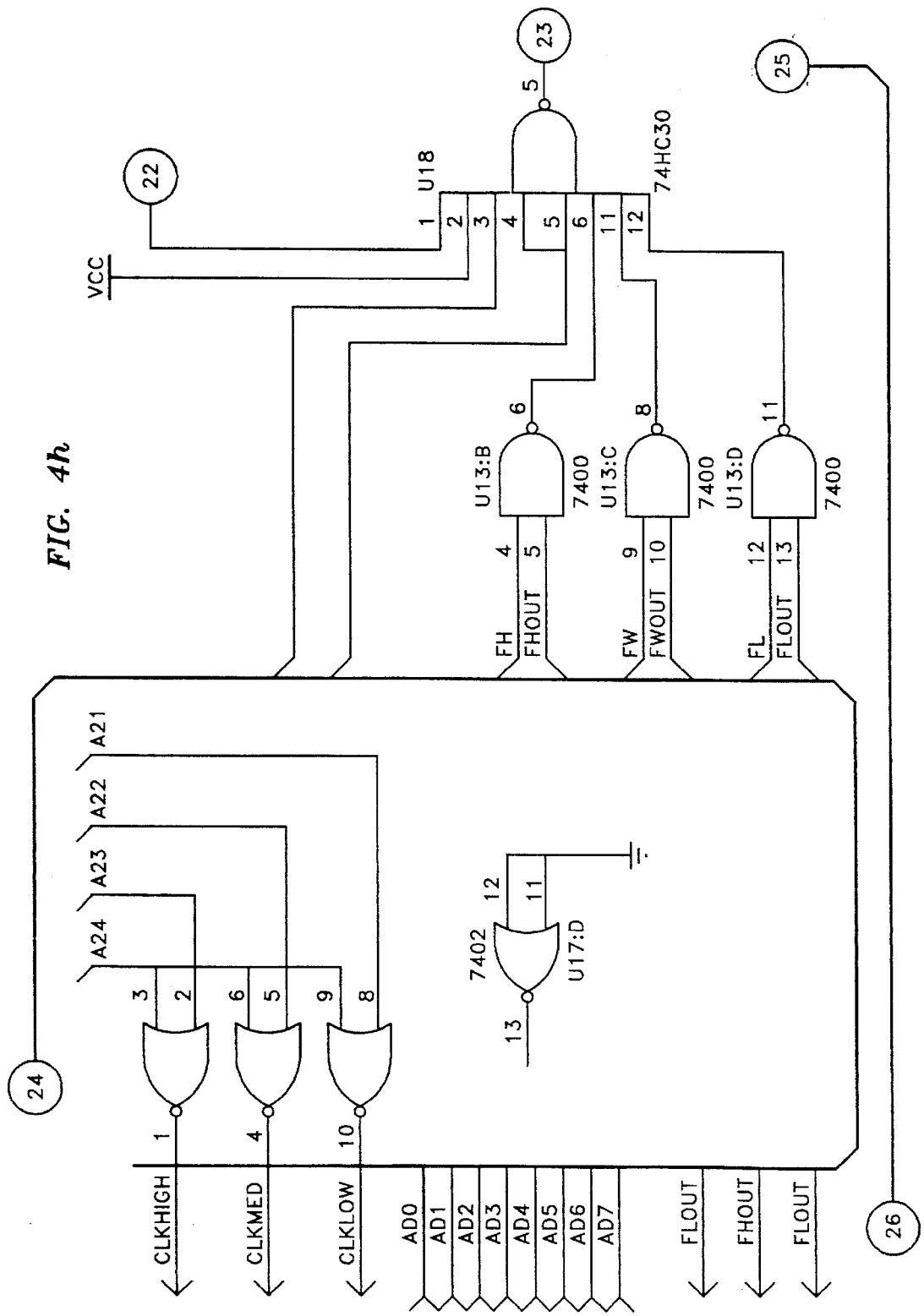
Figure 4I:
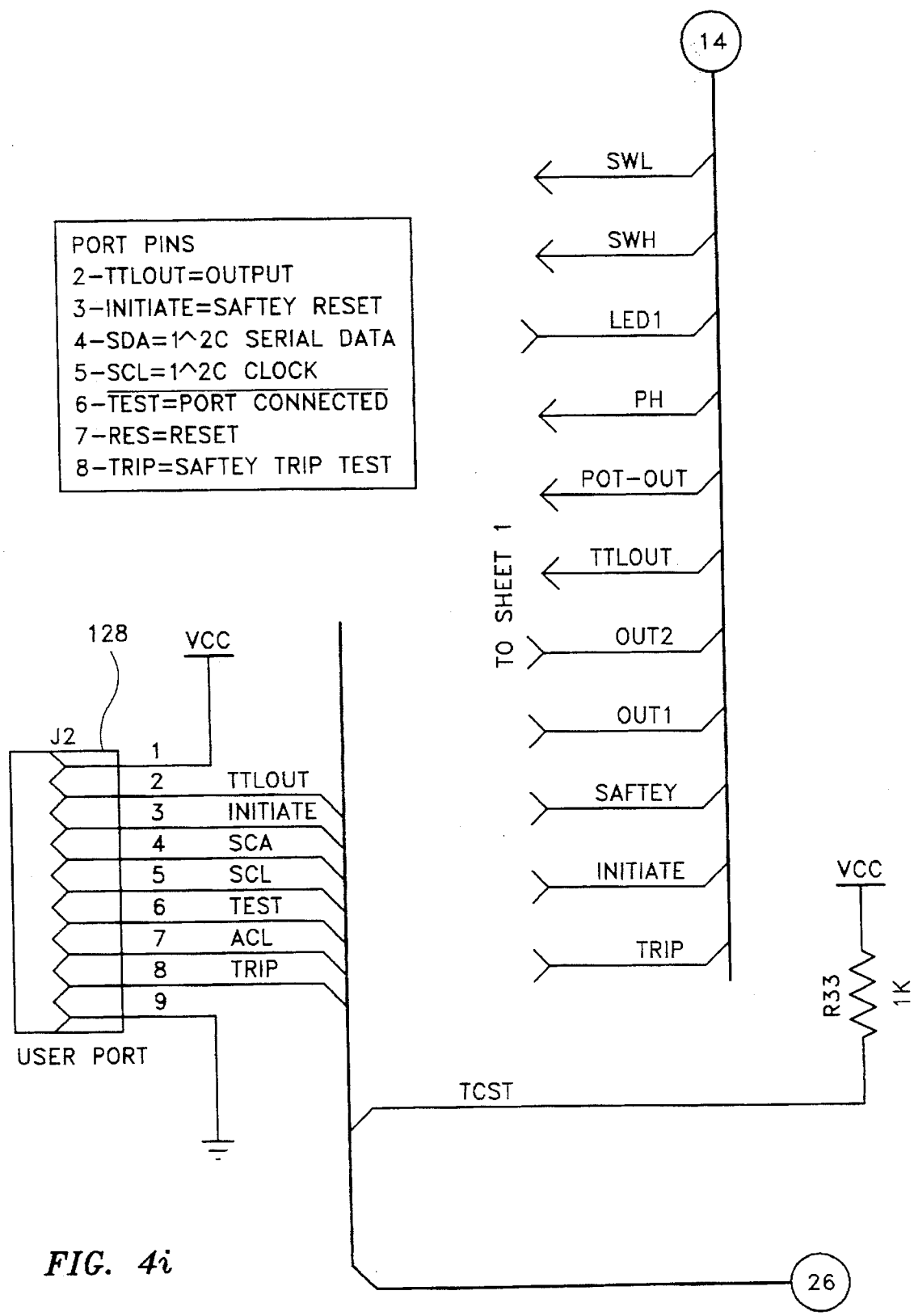

The keyboard means 18 is coupled to a suitable input/output display means 20 through the micro controller 16. The display means 20, as seen in FIG. 2, displays information representative of the specific frequency output signal or sequence of output signals and a number, if chosen, that is representative of a predetermined number of specific frequency output signals that are automatically selected by selection of one representative number by a user. In addition, the display means 20 displays information relating to the time selected for a particular specific frequency signal to run and to the time remaining for a particular specific frequency signal to be generated by the system 10, either singly or as part of a chosen sequence, during the running of the system 10. The system 10 also includes an automatic frequency or channel selector 21 which is coupled to the micro controller 16. The term channel may also be used at times herein to designate a precise frequency output signal. The automatic frequency selector 21 is arranged to be placed in contact with a subject for purposes of scanning such subject and selecting automatically a particular sequence of precise frequency output signals for application to such subject. Such selection is based on sensing the frequency pattern of a subject and then determining the appropriate sequence of precise frequency output signals to be generated automatically in response to the condition sensed.

The frequency synthesizer 12 is coupled to a suitable output circuit 22 for amplification to a desired value. The output circuit 22 is then connected to a suitable application means 24 for applying the amplified specific precise frequency output signal to a subject for a desired application, which may be health science, industrial, commercial or other as desired. As seen in FIGS. 9 and 10, the system 10, except for the application means 24, is contained within a suitable enclosure 26. The application means may take the form of electrically conductive electrodes 28 in the form of elongated stainless steel cylinders that are connected to the system by suitable leads 30. The conductive cylinders are adapted to held in the hands of a user of the system 10. The electrodes 28 may also take any suitable form such as the electrically conductive metal foil strips 32 shown in FIG. 10. Preferably, the foil strips 32 are covered in cloth coverings that are wet by a suitable electrically conductive fluid such as water to ensure that the amplified output signal properly flows through the electrode means. In such applications as may require the use of the metal foil strips as seen in FIG. 10, the strips 32 are placed in contact with the body or an extremity of a subject and are arranged in a directly opposing manner so as to position the afflicted extremity or afflicted portion of an extremity or the like directly between such electrode means. The term application means 24 should also be construed to include means to apply the specific frequency signals for such applications as industrial and commercial uses. In such instances a suitable transmitter of such frequency signals could be wire screens immersed in containers or vats of a conductive fluid, such as water, for the transmission of the frequency signals to a subject such as food which is to be sanitized or disinfected by these specific frequency signals.

The system 10 has additional affirmative features. Upon application of a control signal to the frequency synthesizer means 12 to generate a specific precise frequency output signal for application to the output circuit 22, a signal is directed to a circuit 34 which is termed a soft start circuit and which is coupled to the output circuit 22. As seen most clearly in FIG. 13, the soft start circuit 34 is operative at the initiation of a specific precise frequency signal to gradually increase the value of the amplified frequency output signal from the output circuit 22 at a predetermined rate from zero to a predetermined ultimate determinable output value. As shown in FIG. 13, this ramp up of the amplified output signal takes place in a predetermined time period which for present purposes has been chosen to be a time period around 0.25 sec. Such a ramp up or soft start of the amplified output signal permits the subject to become quickly acclimated to the application of such signal through the output means without undue surprise to the subject. The soft start application of the amplified output signal, as seen also in FIG. 14, is interposed at the start of each specific precise frequency signal, including all frequency signals which appear in a predetermined sequence.

Another feature of the system 10 is an audio warning circuit 36 which coupled to the micro controller 16 that directs the sound circuit 36 to sound an audible sound or alarm prior to the initiation of the application of a specific precise frequency output signal to the output means 22. The purpose of the audible signal or alarm by the circuit 36 is to alert a subject to which the application means 24 have been applied of the initiation of application of the amplified output signal. As seen in FIG. 14, a time period of around 5 to 10 seconds is interposed between specific frequency signals appearing in a sequence and at the commencement of a single specific precise frequency signal to permit the auditory signal to be sounded for a desired predetermined period of time to permit a subject to which the application means 24 is applied to anticipate the commencement of the amplified output signal without surprise.

A security circuit 36 is connected to the micro controller 16. The enclosure 26 for the system 10 is separable for access to the system as may be required. To ensure integrity of the system 10, the security circuit 38 is operative upon opening of the enclosure 10 to disable the system 10 from further operation until the circuit has been reset by a an authorized person.

A suitable power supply 40 for the system 10 is included to supply requisite electrical power to all components of the system. The power supply 40 preferably receives input electrical power at 8 to 20 V DC or AC and with a Hz of 50 to 400, with at least around 1 ampere.

Referring again to FIG. 10, the actuable portion of the keyboard means 18 and the visual display portion of the display means 20 will be seen on the upper portion of the enclosure 26. The visual portion, illustrated by four single digit numbers 21, of the display means 20 displays information representative of a specific bio-active precise frequency signal either being selected by a user of the system 10 prior to starting the system to generate bio-active frequency signals or is representative of a specific precise frequency signal then being generated by the system 10. The first two digits of the three digits 23 of the display 20 also display the time selected by a user by actuation of the keyboard means 18 for a particular frequency or channel to be run. The full three digits 23 of the display 20 also display the time remaining for a specific precise frequency output signal to be generated to suitably inform the user of the system.

As previously discussed with respect of FIG. 12, an OFF signal may be generated by the system 10 to provide a desired ON/OFF cycling of certain frequency output signals with the OFF period remaining constant at around 1 sec. and the ON period of the frequency output signal being variable between about 1 to 7 sec. according to the control of a user. The period for the frequency signal to be generated, as noted above, is determined by actuation of the keyboard means 18 and would generally be considered to be around three minutes in duration.

In the illustrated embodiment of the invention, the ON pulse period for a particular frequency signal is displayed by the single digit display 42 and such ON pulse period may be determined by a user by selective actuation of a switch 44 to increment the pulse period displayed to the desired period of time. In addition, a LED display 45 provides a visual indication to a user of the system 10 of the existence of an ON period for the precise frequency output signal.

The enclosure 26 is provided with a suitable ON/OFF switch 46 for the system 10. In the present instance, output receptacles 48 are provided for the electrode means 24 at the upper portion of the enclosure 26.

As was previously described, the amplitude of the amplified output signal is determinable by a user of the invention. A suitable amplitude control 50, such as for, example, a variable resistor, permits a user to adjust the amplitude of the amplified frequency output signal to a comfortable level commensurate with sufficient amplitude to accomplish the desired health science and/or commerical application. Generally, this amplitude is not expected to exceed a level of around 50 volts. Another LED 52 displays further information concerning the application of the amplified output signal to a subject and indicates if the electrode means 24 are not in proper contact with the subject by indicating that an open circuit condition has been sensed by the invention so that proper corrective action may be taken to ensure proper application of the electrode means 24 and correct flow of the output signal.

The illustrated portion of the keyboard means shows various keys AUTO, RUN, SEQ, DEL, SELECT, and RESET that may be actuated by a user of the invention to choose a specific frequency signal or a sequence of such signals or to choose a preprogrammed sequence of signals or to store for future access a predetermined sequence of frequency signals.

As an example of an exemplary application of the present invention, the following table sets forth a number of conditions that may be encountered in the health science field. The table also indicates a particular code or channel which is representative of a Specific frequency output signal that may be applied to advantage in alleviating such condition or inactivating a particular micro-organism which is responsible for such condition. As will be noted, in some instances a plurality of frequencies or sequences of frequencies may be used to advantage.

| CONDITIONS | REPRESENTATIVE FREQUENCY NUMBER |
| --- | --- |

Adynamia, geriatric (fatigue of age)--(applicators placed on solar plexus and behind animal's head)--49, 56
Abdominal inflammation--31, 82, 4, 5, 6, 9, 10, 12 + 16, 14, 15, 17, 18, 20, 28, 29 + 86, 88, 42, 45, 48, 58, 103, 104, 105, 106, 107, 112, 118, 119, 121, 125
Abdominal pain (applied to solar plexus and belly--78, 104, 45, 40, 57, 87, 88, 108, 109, 114, 1, 3.
Also for parasites+86, 42, 45, 48
Abscesses--4, 6, 14, 17, 20, 39, 101
Acidosis (urine too acid)--1, 14, 16, 17, 18, 20, 58, 88

-continued

| CONDITIONS | REPRESENTATIVE FREQUENCY NUMBER |
|---|---|

Acne--4, 6, 9, 10, 12, 14, 17, 20
Actinomycosis--28, 1, 17, 20, 58
Acupuncture disturbance field (scar focus)--59
Acute Pain--40, 57, 3, 45, 87, 88, 108, 109, 114, 1, 14, 17, 20 + 22 + 24
Adenoids--11 + 16, 14, 17, 18, 20, 29, 58, 105, 106, 107, 109, 110, 112, 116, 117, 121, 123, 4, 6
Adhesions--4, 6, 11 + 16, 14, 17, 18, 19, 20, 39
Adrenal stimulant--58
Allergy--1, 78 and 32, 87, 88, 108, 109, 114, 42, 45, 48, 58, 29 + 86
Alopecia (loss of hair)--1, 14, 17, 20, 28, 88
Amenorrhea (absence of menstruation)--29, 87, 88, 108, 109, 114, 42, 45, 48, 14, 1, 3, 17, 19, 20, 58
Anal itching (Pruritus)--28, 29, 42, 45, 48, 29 + 86, 58, 112, 87, 88, 108, 109, 114
(Secondary: 1, 14, 17, 19, 20)
Angina (quinsy--in throat)--17, 18, 20, 28, 105, 106, 107, 109, 110, 112, 117, 118, 119, 121
Ankylosing spondylitis--3, 45, 11 + 16, 14, 17, 18, 20, 25 + 26 + 27, 55, 82, 61, 54, 55, 69,
82, 43, 44, 49, 123, 105, 106, 109, 110, 112
Antiseptic effect--11 + 16, 14, 17, 19, 20, 28, 29, 103, 105, 106, 107, 108, 109, 110, 112, 118, 119
Apoplexy (stroke paralysis)--often caused by netzsitter geopathic zone 53, 58, 9, 25 + 26 + 27,
42, 45, 48, 58, 29 + 86, 87, 88, 108, 109, 114, 14, 17, 20
Appetite, lack of--28, 29 + 86, 42, 45, 48, 58, 1, 14, 17, 20
Arteriosclerosis (hardening of arteries: regeneration takes time but is accelerated by full-body sunbaths;
stopped before reddening)--1, 4, 6, 9, 10, 12, 14, 17, 18, 20, 58, 123
Arthritis (since many different organisms can cause arthritis, 20 many frequencies must be tested.
See other types of arthritis below---) 1, 11, 14, 16, 17, 20, 55, 58, 69, 78, 82
Arthritis, rheumatoid of the muscles and tendons--34, 82, 25 + 26 + 27, 17, 20, 123
Arthritis, arthrosis, and parathyroid disturbances affecting calcium metabolism--62
Arthritis, arthralgia due to gout--63
Arthritis: focal origin (gastrogenic, tonsillogenic, and syphilis or paresis)--63
Asthma--4, 6, 9, 10, 12, 14, 17, 20, 123
Astrocytoma--65, 67, 69, 6, 7, 14, 22, 24
Ataxia (incoordination of muscles--slow results in some cases)--4, 6, 9, 10, 12, 14, 17, 18, 20, 25, 26, 27,
29 + 86, 42, 45, 48, 58, 121, 125 spastic ataxia--65, 67, 69
Athlete's Foot--Try 28 first, then 11, 14, 16, 20, 58
Autoimmune Disorders--1, 11 + 16, 14, 17. 18. 20, 25, 26, 27, 28, 34, 55, 58, 62, 63 69, 78,
87, 88, 102
Autointoxication--85, 87, 88, 1, 14, 17, 20, 58, 108, 109, 114
Back pain--Best is 57 for 15 min. + 40, 3, 87, 88, 108, 109, 114.
Others: 1, 19, 11 + 16, 14, 17, 20
Bad Breath (halitosis)--11 + 16, 14, 17, 20, 58
Bedsores--14, 11 + 16, 17, 20, 28 and 58; then 82 and 47
Biliousness--11 + 16, 1, 14, 15, 17, 20, 28
Bladder and prostate complaints--14, 11 + 16, 17, 20, 28, 58, 63
Boils--14, 11 + 16, 17, 20, 28, 106, 107, 109
Bone trauma (cuts, fractures)--31, 11 + 16, 1, 14, 17, 20
Bone/periodontal disease (also osteomaiacia, etc., greatly aided by full-body sun exposure) 51, 9, 10,
25 + 26 + 27, 14, 17, 18, 20
Bone protuberance (spurs)--82 and 34
Brachial Neuralgia (electrodes placed on elbow and head)--85
Breast: fibroid cysts--14, 11 + 16, 17, 18, 20 + 22 + 24
Bright's Syndrome (Nephritis)--12, 14, 17, 20
Bronchial asthma--85, 87, 88, 42, 45, 48, 29 + 87, 58
Bronchitis--14, 20, 63, 64
Bronchial Pneumonia--11 + 16, 14, 17, 18, 20
Bubonic Plague--101, plus secondary infections: 14, 17, 20, 58
Burns--39, 1, 14, 17, 20, 28, 38
Bursitis (may be caused by many viruses; also experiment with arthritis frequencies)--14, 17, 20
Cancer: see Carcinoma, Leukemia, and Sarcoma
Candida--28
Carcinoma--7, 14, 17, 20 + 24 + 22, 107
Cardiac Edema (congestive heart failure)--65
Carpal Tunnel Syndrome--11 thru 28, 71, 41, 80, 20, 87, 88, 29
Cataract--1, 14, 17, 20
Catarrh--11 #16, 14, 17, 20, 29, 58
Cerebral Palsy--14, 17, 20, 87, 88
Chicken Pox (Varicella)--11 + 16
(and for secondary infections)--9, 10, 12, 14, 17, 20, 58
Cholera--14, 16, 103, 14, 17, 20
Chronic Fatigue Syndrome (generic disorder)--1, 4, 9, 14, 16, 17, 18, 20, 28, 29 + 86, 32 41, 42,
45, 47, 48, 54, 56, 58, 71, 74, 105, 106,
Circulatory stasis--53
Circulation disturbances/problems--53, 63
Concentration (to increase mental-)--68
Cold in head, chest (Common cold/Adenoviruses mutate constantly; there are too many new strains to
include a complete list for every cold)--1, 11, 14, 16, 17, 18, 20, 29, 58
Colic--11, 15, 16, 17, 20, 58
Colitis (irritation of colon)--11, 14, 15, 16, 104
Constipation--11, 14, 16, 17, 18, 20, 58
Convulsions--1, 14, 17, 20 (most commonly used)
Contusions--66 and 43 over the focus -continued

| CONDITIONS | REPRESENTATIVE FREQUENCY NUMBER |
|---|---|

Costalgia (rib pain)--40, 57, 3, 14, 17, 20, 1, 11 + 16
Cramps--1, 14, 17, 20, 57
Cystitis (of urinary bladder)--11, 14, 16, 17, 20, 28, 58
Deafness (partial to complete)--1, 11, 14, 16, 17, 20, 58
Dental foci (neglecting this can prevent recovery from ANY illness)--3, 45, 39, 51, 10, 11 t 16,
12, 14, 1 5, 17, 18, 19, 20, 24 + 25 + 27, 28, 4, 5, 9, 87, 88, 108, 109, 114
Depression, anxiety, trembling, weakness --77
Depression (due to exogenous circumstances--54 and 17
Depression (due to drugs or toxins)--83 and 47
Detoxification--71, 41, 80, 20, 87, 88, 29, 24, 105, 14, 17, 108, 109, 114
Diabetes--54 + 111 + 17, and 61 + 34, 25 + 26 + 27, 42, 45, 48 + 58 +
86, 87, 105 and 53 + 63 for circulation problems.
for secondary infections: 1, 4, 6, 9, 11, 14, 16, 20, 28, 58
Diabetic loading-54 and 21
Diarrhea/Dysentery--11, 14, 16, 17, 20, 28
Distorsion (Twisting of muscles, spine)--66 and 43
Dizziness--73
Dupuytren'S Contracture--82 and 34
Dysmenorrhea--For rapid, lasting relief of painful menstruation: after a pure water douche,
use #57 over and under uterus; leave running after pain disappears.
When cause is uterine infection: 74, 11 + 16, 14, 17, 20, 28
Dyspepsia (indigestion)--11, 14, 16, 17, 20
Ears--various maladies--discharges, vertigo, ringing, hearing loss--65, 14, 17, 20, 58
Eczema--65, 11, 16, 17, 20
Eczema in vascular and lung functional disturbances--63
Enuresis--1, 14, 17, 20, 28
Edema--87, 88, 71 and 41, 29, 104, 14, 17 20, 28
Epicondylitis (pain in elbow)--82 and 34, 3, 40, 57
Epididymitis (inflammation of testicle area/ducts)--12, 14, 17, 20, 58
Epilepsy --1, 14, 16, 17, 20, 21, 25, 27, 42, 58
Epstein-Barr--105, 106, 18, 28, 14, 17, 20
Erysipelas (skin inflammation) caused by strep pyogenes, etc.--106, 112, 1, 14, 17, 20, 28, 58
Erythema nosodum--63
Esophagus (congestion)--14, 17, 20
Eustachian tube inflammation--11, 14, 16, 17, 18, 20, 28
Eye inflammation (on left and right temples)--82 and 46
Eye Disorders (blurred, cataracts, crossed, diplopia, infected, etc.)-- 10, 1, 14, 17, 20, 58
Eyes (Glaucoma)--10, 14, 17, 20
Facial paralysis--1, 14, 17, 20, etc.
Fatigue--4, 9, 105, 106, 28, 42, 45, 48, 56, 58, 29 + 86
Fever (various causes)--14, 17, 20, 58
Fibroma.7, 8, 20, 22, 24 (secondary: 11, 16, 28)
Fibrosis of lung--56 and 37 and 30 on chest
Fistula, Ulcer--14, 15, 17, 20
Flashes, hot (complications)--1, 14, 17, 20
Flatulence (intestinal gas)--11, 14, 16, 17, 19, 20, 28
Flu--11, 14, 16, 17, 20, 58
Foot--blisters--1, 14, 17, 20, 28
Fractures--37 and 36, 1, 14, 17, 20
Frostbite--14, 17, 20
Frozen shoulder--1, 14, 16, 17, 20
Fungal infection--28, 11, 14, 16, 20, 58
Furunkulosis herpes, skin diseases--38 and 13, 11, 16, 112; secondary 17, 20
Gall bladder dystonia with osteitis--79, 3, 14, 17, 20, 58
Gallstones--79, 3, 14, 17, 20, 58
Gangrene--14, 17, 20, 58, 47
Gas (intestinal)--11, 14, 16, 17, 19, 20, 28
Gastritis and flatus--14, 15, 17, 20, 58
Gout--63, 3, 14, 17, 20, 58
Gravel in urine--79, 3, 14, 17, 20, 58
Gums (inflammation, gingivitis, pyorrhea)--11, 14, 16, 17, 20, 28, 58
Hair loss (alopecia)--1, 14, 17, 20, 28, 88
Hallucinations--1, 14, 17, 20, 58
Hangover--1, 87, 88
Hay Fever (only on some types)--14, 17, 20, 58
Headaches--Best freq. for very rapid relief of symptoms-#40 applied near hairline. Continue for
10 min. or until pain disappears; then massage scalp in CW direction. Nevertheless, if headaches persist
despite elimination of all possible causes, check the possibility of tumor. For headaches of unknown
cause or toxins--61, 71, 87, 88, 74, 3, 20, 41, 42, 45, 48, 58, 61, 73, 80, 29, 23, 14, 17, 25, 26, 27,
3, 105, 106, 108, 109, 114
For headaches caused by parasites--40, 42, 45, 47, 58, 20, 3
Headaches: urogenitaiiy caused--40, 63, 3, 108, 109, 114
Headaches caused by vertebral misalignment-(not a substitute
for chiropractic adjustment)--40, 62, 3
Head Injuries (seek immediate medical attention)--40, 62, 3, 14, 17, 20, 87, 48, 73, 74
Hearing problems--1, 11 + 16, 14, 17, 19, 20, 58
Heart (lab animals only) (see Pericarditis)--46, 40, 58, 47, 75, 1, 14, 17, 20, 28, 42, 45, 58
Heartburn--15, 4, 6, 7, 9, 10, 11 + 16, 12, 14, 17, 20, 23, 28, 29 + 86, 42, 45, 48, 58

-continued

| CONDITIONS | REPRESENTATIVE FREQUENCY NUMBER |
|---|---|

Hemorrhage (uncontrolled bleeding)--11, 16
Hemorrhoids--11, 14, 16, 20
Hepatitis (generic---placement is over and behind liver)--82 and 55, 11, 14, 16, 20
Hernia--1, 17, 20
Herpes (zoster)--4, 6, 9, 10, 12, 11, 16, 86 and (secondary) 14, 17, 20, 58
High blood pressure, hypertension--1, 14, 17, 20, 65
Hip Pain (as in coxarthritis)--3, 14, 17, 20, 40, 57
Hives (Urticaria)--9, 14, 17, 20, 87, 88, 74
Hoarseness--14, 19, 20
Hyperacidity of stomach--68 on solar plexus and 36 on stomach
Hydrocele (fluid in testicle, etc)--14, 17, 20
Hyperosmia (taste--morbid)--58, 1, 87, 88, 124
Hyperthyroid--78 and 85
Hypoacidity of stomach--111, 58 over & behind pancreas
Hypothyroid (Thyroid deficiency)--60 behind head, and 54 on thyroid
Hypertension--58, 45, 65, 72, 1, 14, 17, 20, Some other varieties of hypertension: (kidney-induced, red-high, diastolic high pressure)--65 and 72
Hypertension, spastic--45
Impotence (many causes)--63, 7, 8, 28, 14, 16, 17, 20 + 22 + 24, 42, 45, 47, 48, 58, 25 + 26 + 27
Indigestion--1, 14, 17, 20, 28, 29, 58, 42, 45, 48, 74
Infantile Paralysis--12, 14, 17, 20
Infections (many classes)--10, 11, 12, 14, 15, 16, 17, 18, 19, 20, 21, 22, 24, 25, 26, 27, 28, 29, 42, 45, 48, 58, 86, 101, 103, 104, 105, 106
Infertility--7, 8, 28, 14, 16, 17, 20 + 22 + 24, 25 + 26 + 27, 63
Inflammation--81
Influenza (flu viruses mutate frequently; these codes are only a partial list)--11, 16, 12, 14, 17, 20, 58
Insomnia--76, 78, 11, 12, 14 and 16
Intercostal neuralgia (pain in rib musculature)--3, 40, 57, 11, 14, 16, 17, 18, 20, 42, 58, 86, 29
Intermittent claudication (behind the head)--52 and 50
Itching (Pruritis)--14, 17, 20, 28, 29, 42, 45, 48, 58, 29 + 86, 112
Jaundice (liver)--10, 11, 12, 14, 16, 25, 26, 27, 29 + 86, 88, 34, 42, 45, 48, 58
Kidney insufficiency (many viruses and toxins cause this)--61 and 53, 104, 10, 11, 12, 14, 16, 17, 20, 25, 26, 27, 28, 47, 53, 61, 29 + 86, 87, 88, 34, 41, 42, 45, 48, 58, 108, 109, 114
Knee/Joint pain--3, 40, 57, 11, 14, 16, 17, 20, 55, 58, 69, 78, 82, 34, 82, 62, 63
Larynx--104, 28, 29, 11, 14, 16, 17, 20, 55, 69, 78, 82, 34, 82, 62, 63
Leprosy (more below)--27
for infection of lesions: 10, 11, 12, 14, 15, 16, 17, 18, 19, 20, 21, 22, 24, 25, 26, 27, 28, 29, 58, 101, 103, 104 to 106
Leukemia--7, 8, 14, 17, 20, 22, 24, 107
Leukodermia--14, 17, 20, 29, 58, 107, 112
Locomotor Dysfunction (slow results if nerve damage exists) incoordination--1, 14, 17, 18, 20, 25, 26, 27, 29 + 86, 42, 45, 48, 58
convulsions, spasticity--65, 67, 69
Low Blood Pressure, hypotension--14, 17, 20, 58
Lumbago--1, 14, 17, 20, 42, 45, 48, 29 + 86, 65, 67, 69
Lungs--11, 16, 14, 17, 18, 20, 42, 45, 48, 58, 29 + 86, 103, 107
Lupus Erythematosis--14, 17, 20, 18, 102
Luxation (dislocation of organs or joints)--66 and 43
Lymph stasis--71 and 41, 80, 20, 87, 88, 29, 105, 14, 17
Malaria--108
Measles (all)--109
Mental Disorders (toxins usually the cause)--29, 41, 58, 71, 80, 87 88, 1, 42, 45, 48, 74, 20, 105, 29, 11 to 28
Menieres Disease--11 + 16, 14, 17, 20, 28, 105, 107, 109
Meningitis--11 + 16, 14, 15, 17, 20, 25, 26, 27, 28, 29 + 86, 42, 45, 48, 58, 105, 106
Menstrual problems-- plain water douche first, then #57 applied above and behind uterus until pain disappears.
Other frequencies--3, 14, 17, 20, 28, 40, 58
Migraine--40 and 61, usually applied near hairline.
Motion Sickness--25, 26, 27, 28, 29 #86, 87, 88, 42, 45, 48, 58
Mouth--eruptions; white patches (precancerous, leukoplakia)--28, 7, 8, 20, 22, 24
herpes sores........5, 9, 28, 11, 12, 14, 17, 20, 102, 105
Mucous membrane inflammation--31
Multiple Sclerosis--use "Autoimmune" frequencies plus 14, 17, 20
Muscles, to relax (myospasms)--19 and 70
Muscular Dystrophy (suggested)--1, 11 + 16, 14, 17, 18, 20, 25, 26, 27, 28, 34, 55, 58, 62, 63 69, 78, 87, 88, 102, 87, 88, 108, 109, 114
Muscular pain (reported as applied to the focus of injury or pain for short periods, from 30 seconds to 3 minutes, depending on need)--3, 57, 40, 33, 34, 35, 46, 53, 61, 73, 80, 81, 82, 84, 85
Muscle pain from parasites--29 + 86, 42, 445, 48, 58
Mumps--1, 20, 4, 5, 7, 8, 110, 105, 14, 17, 20, 58
Nausea--14, 15, 17, 20, 58, 74
Nephritis\nephrosis--14, 17, 20, 61, 53, 47 and 28
Nervousness, from geopathic netzgitter zones, drugs, Prozac agitation (akathsia)............78
Nerve disorder--1, 4, 5, 6, 9, 10, 11 + 16, 14, 17, 41, 71, 80, 87 88, 20, 25, 26, 27, 42, 45, 48, 58, 105, 106, 109
Neuralgia--75, 108, 109, 114. Sometimes frequencies for nerves above .
Neurosis--55

-continued

| CONDITIONS | REPRESENTATIVE FREQUENCY NUMBER |
|---|---|

Nose--infection, congestion--11 + 16, 14, 17, 18, 20, 29, 104, 28, 58 Numbness--1, 4, 5, 6, 9, 10, 11 + 16, 14, 17, 20, 25, 26, 27, 104, 106, 109
Oral Lesions--4, 5, 8, 9, 10, 11 + 16, 14, 17, 18, 19, 20, 28, 29, 87, 88, 108, 109, 114
Orchitis (Inflammation of testes due to TB, mumps, gonorrhea, cancer, etc.)--4, 5, 6, 7, 8, 9, 10, 11 + 16, 12, 14, 15, 17, 18, 20 + 22 + 24, 25, 26, 27, 42, 45, 48, 58, and 110
Osteomyelitis (bone infection)--79, 4, 5, 6, 7, 8, 9, 10, 11 + 16, 12, 14, 15, 17, 18, 20 + 22 + 24
Osteomalacia--full body sunbathing (stop before skin reddens)
Otosclerosis (type of deafness)--65
Ovarian disorders--25 + 26 + 27, 28, 29, 57, 4, 5, 6, 7, 8, 9, 10, 11 + 16, 12, 14, 15, 17, 18, 20 + 22 + 24, 58
Pain (look under appropriate affliction for more)--3, 45, 40, 57
Pain of infection--3, 40, 57, 45, 14, 11 + 16, 17, 18, 20, 74
Pain of cancer--3, 40, 57, 45, 7, 8, 20 + 22 + 24
Pancreatic insufficiency--111, 61 over pancreas and 34 under (behind?) pancreas, --(secondary)--25 + 26 + 27, 28, 29, 57, 4, 5, 6, 7, 8, 9, 10, 11 + 16, 12, 14, 15, 17, 18, 20 + 22 + 24, 58
Paralysis, spastic (slow results in some cases)--1, 14, 17, 18, 20, 25, 26, 27, 29 + 86, 42, 45, 48, 58, 69
Paralysis, nonspastic (langorous) (slow results in some cases)--1, 14, 17, 18, 20, 25, 26, 27, 29 #86, 42, 45, 48, 58, 65, 67
Parasites--42, 45, 48, 58, 29 + 86
Pelvic Inflammatory Disease (PID)--4, 5, 6, 7, 8, 9, 10, 11 + 16, 17, 18, 20 + 22 + 24, 25, 26, 27, 28, 29 + 87, 45, 48, 103, 105, 110, 107, 118
Pericarditis--4, 6, 10, 14, 11 + 16, 17, 19, 20, 26, 28, 40, 42, 47, 57, 58, 75, 45, 46, 47, 48, 29 + 86
Pharyngitis--104, 107, 31, 10, 11 + 16, 18, 17, 14, 20, 58, 87 88,
Pleurisy--11, 16, 14, 17, 18, 20, 42, 45, 48, 58, 29 + 86, 103, 107
Pneumonia--11, 16, 14, 17, 18, 20, 58, 103, 107
Poliomyelitis--121,
secondary complications--11 + 16, 105, 12, 14, 17, 20
Polyps--4, 5, 6, 7, 8, 9, 10, 20 + 22 + 24, 25 + 26 + 27, 28, 29, 58, 87, 88
Pre-op and post-operation--prevention and control of nosocomial (hospital-acquired) and idiopathic infection--6, 9, 10, 11 + 16, 12, 14, 15, 16, 17, 18, 20, 28, 29, 87, 88, 105, 107, 109
Prostatitis, benign prostate tumor--44 and 30, 87, 88, 4, 5, 6, 7, 8, 11 + 16, 17, 18, 20 + 22 + 24, 28, 42, 45, 48, 58, 29 + 87
Prostate complaints--63, 7, 8, 20, 22, 24, 28, 14, 16, 17, 20, 42, 45, 47, 48, 58
Proritis (itching)--14, 17, 20, 28, 29, 42, 45, 48, 58, 29 + 86, 112
Prostate tumor (malignant) one electrode against navel, other against rectum--7, 8, 20 + 22 + 24
Psychosomatic pain (viral, energetic meridian blocks, toxicity, nutritional)--20, 40, 57, 41, 44 + 32, 87, 88, 108, 109, 114
Pyorrhea (periodontal disease: jawbone infection; receding gums)--4, 5, 8, 9, 10, 11 + 16, 14, 17, 18, 20, 28, 29, 87, 88
The electrodes are placed so the infection lies on a straight line between them.
Rabies--122
Raynaud's Disease (cold hands & feet)--20, 58
Rheumatoid arthritis of the muscles and tendons--82 and 34, 62, 63, 25 + 26 + 27, 1, 11 + 16, 14, 17, 20, 55, 58, 69, 78, 82
Rhinitis or Runny nose--1, 11 + 16, 12, 14, 17, 18, 20, 29, 58, 87, 88, 28
Sarcoma--7, 8, 14, 17, 20, 22, 24, 107
Scars--59 + 11 to 28
Scarlet Fever--14, 17, 20, 22 + 24
Sciatica or Ischia (severe cases require direct application of electrodes over and behind the afflicted area at a high intensity)--11 + 16, 14, 17, 20, 22, 24, 61
Sedative Effect (reported use on bleeding, bruises, insomnia, sinusitis (also reported use on lymph stasis/edema, auricular treatment)--80
Sexual Dysfunction--63, 7, 8, 28, 14, 16, 17, 20 + 22 + 24, 42, 45, 47, 48, 58, 25 + 26 + 27
Shingles #Herpes Zoster--11 + 16, 9, 86 (secondary) 14, 17, 20, 57
Sinusitis--11 + 16, 14, 17, 20, 42, 48, 87
Sleeping Sickness--124
Slipped discs (includes spasms from microbial toxins)--57 (BEST), 42, 14, 17, 109, 17, 20, 45, 48, 87, 88, 108, 109, 114
Smallpox--125 plus 11, 16, and (secondary) 14, 17, 20
Sneezing--14, 17, 20, 28, 88
Sore Throat (pharyngitis) (consider also food allergies)--4, 5, 9, 10, 11 + 16, 14, 17, 18, 20, 28, 107, 123
Spasms, muscle--70
Spastic paresis--25, 26, 95 and 50
Spleen, enlarged--54 and 17
plus secondary--1, 4, 6, 9, 11, 14, 16, 20, 28, 58
Spondylitis, acute--82 and 61, or 69 and 55 on the focus
Staphylococci infection--20
Stiff neck--74.
Spastic stiff neck--65 and 72
Stiff muscles in general--33, 34, 35, 40, 42, 46, 53, 58, 61, 73, 80, 81, 82, 84, 85, 9, 11 + 16, 14, 17, 18, 20
Stomach disorders--7, 8, 14, 17, 20, 20 + 22 + 24, 42, 45, 48, 58, 75, 103, 118, 119
Stones--77
Streptococci infection--14
Streptothrix infection--17
Sty--1, 14, 17, 20, 58
Subluxation induced disorders--62
Sun Allergy (consider also that prescription drugs, such as Psoralen, often produce a "sun allergy"

-continued

| CONDITIONS | REPRESENTATIVE FREQUENCY NUMBER |
|---|---| due to phototoxic effects on the liver)--78 and 32
Sunstroke--29, 105, 39, 3, 45, 87, 88, 14, 58
Surgery--Prevention and control of nosocomial (hospital-acquired) and idiopathic infection--6, 9, 10, 11 + 16, 12, 14, 15, 16, 17, 18, 20, 28, 29, 87, 88, 105, 107, 109 surgical pain, post-op recovery--3, 45, 40, 57, 44 + 32
Swelling (Edema)--87, 88, 71 and 41, 29, 105, 14, 17, 20
Swollen glands--14, 17, 20, 58, etc.
Syphilis--25 + 26 + 27
Tachycardia (also used for pain of arthritis, headache, Tui-na, and facial toning)--82
Teeth (pain) Also see Pyorrhea.
This can prevent recovery from other illnesses: 3, 45, 39, 51, 10, 11 + 16, 12, 14, 1, 5, 17, 18, 19, 20, 24 + 25 + 27, 28, 4, 5, 9
Tendomyopathy (applied to the focus of injury or pain for short periods, from 12 seconds to 3 minutes, depending on need)--3, 33, 34, 40, 46, 53, 57, 58, 61, 73, 80, 81, 82, 84, 85, 87, 88
Tetanus--125, 27
(for secondary complications)--14, 17, 20
Thrush (aphtha, sprue, stomatitis)--28
Tonsillitis--82 and 47, 11 + 16, 12, 14, 15, 17, 18, 20, 25 + 26 + 27, 28, 123, 107
Toothache (hidden dental and jaw infection or foci will prevent recovery from ANY illness)--3, 45, 39, 51, 4, 5, 9, 10, 11 + 16, 12, 14, 15, 17, 18, 20, 24, 25, 27, 28, 87, 88, 108, 109, 114
Tooth extraction, afterward--3, 45, 51, 68
Toxins--29, 41, 87, 88, 108, 109, 114. 1, 14, 17, 20, 42, 45, 48, 58
Trauma--3, 45, 39, 19, 14, 17, 20, 28
Trench Mouth--25 + 26 + 27
secondary complications--14, 17, 18, 20, 25, 26, 28
Trigeminal neuralgia--4, 5, 6, 9, 10, 11 + 16, 14, 15, 17, 18, 19, 20, 25, 88, 68, 56, 105 to 107, 109, 114, 116, 112, 121, 122, 125, 124
Tuberculosis--11 + 16, 20 + 22 + 24
secondary complications--18, 7, 8, 28, 107
Typhoid--118, 119, 11 + 16, 22, 9
Ulcers--5, 6, 7, 9, 10, 14, 15, 16, 17, 18, 20, then 82 and 47
Urethritis--4, 6, 7, 9, 10, 11 + 16, 12, 14, 15, 17, 18, 20, 25 + 26 + 27, 28, 29 + 86, 42, 45, 48, 82
Urticaria (Hives)--(often due to parasite toxins: condition becomes worse until all toxins are excreted)--9, 29, 42, 45, 48, 87, 88, 17, 20, 71
Vegetative Dystonia (involuntary muscle dysfunction)--53
Vein thrombosis (blood clot)--23
Vertigo, giddiness of unknown cause--49 and 73
Warts--4, 5, 6, 7, 8, 9, 10, 12, 20 + 22 + 24
Worms (see note under parasites)--42, 45, 48, 58, 29 + 86
Wound healing--14, 17, 20, 37, 39, 58
Wound healing, Delayed--53 (plus those above)
Yeast infection (Candida albicans, etc.)--28
Yellow Fever--114

MISCELLANEOUS NUMBERS

Requiring special training (acupuncture, aesthetology, biophysics, etc.) SCHUMANN FREQUENCY, used for entraining the brain in psychic healing experiments, and to scan brain for troubled areas--68For RELAXATION, MEDITATION AND DEEPER SLEEP--74To stimulate MENTAL CLARITY--60Facial toning--62Kidney meridian (balancing/correction)--65German and Russian studies have discovered a very high statistical correlation between the personalities of individuals and the position of planets at the time of their birth.

Dr. Sieger believes this is due to the effect of gravitational interference fields. Two frequency patterns which correlate with the fields in that time frame are:

Saggitarius—close to #17, and 38

Capricorn and Aquarius—37

As noted above, the table sets forth certain codes or channels that are representative of precise frequency signals. The precise frequency signals represented by such channels are set forth in the table below which also sets forth the minimum time in seconds that the precise frequency signal is gated ON between one second periods that the frequency signal is gated OFF.

| CODE | FREQUENCY | GATE |
|---|---|---|
| Auto 1 |  | 0 |
| 1 | 10,000 | 0 |
| 2 | 1050 | 0 |
| 3 | 3040 | 0 |
| 4 | 2720 | 0 |
| 5 | 2489 | 0 |
| 6 | 2170 | 0 |
| 7 | 2127 | 0 |
| 8 | 2008 | 0 |
| 9 | 1800 | 0 |
| 10 | 1600 | 0 |
| 11 | 1550 | 0 |
| 12 | 1500 | 0 |
| 13 | 1000 | 0 |
| 14 | 880 | 0 |
| 15 | 832 | 0 |
| 16 | 802 | 0 |
| 17 | 787 | 0 |
| 18 | 776 | 0 |
| 19 | 760 | 0 |
| 20 | 727 | 0 |
| 21 | 700 | 0 |
| 22 | 690 | 0 |
| 23 | 685 | 0 |
| 24 | 666 | 0 |
| 25 | 650 | 0 |
| 26 | 625 | 0 |

-continued

| CODE | FREQUENCY | GATE |
|---|---|---|
| 27 | 600 | 0 |
| 28 | 465 | 0 |
| 29 | 444 | 0 |
| 30 | 410 | 3 |
| 31 | 380 | 3 |
| 32 | 330 | 3 |
| 33 | 320 | 3 |
| 34 | 250 | 3 |
| 35 | 240 | 3 |
| 36 | 230 | 3 |
| 37 | 220 | 3 |
| 38 | 200 | 3 |
| 39 | 190 | 3 |
| 40 | 160 | 3 |
| 41 | 148 | 3 |
| 42 | 125 | 3 |
| 43 | 110 | 3 |
| 44 | 100 | 3 |
| 45 | 95 | 3 |
| 46 | 80 | 3 |
| 47 | 73 | 3 |
| 48 | 72 | 3 |
| 49 | 60 | 3 |
| 50 | 48 | 3 |
| 51 | 47.5 | 3 |
| 52 | 45 | 3 |
| 53 | 40 | 3 |
| 54 | 35 | 3 |
| 55 | 28 | 3 |
| 56 | 27.5 | 3 |
| 57 | 26 | 3 |
| 58 | 20 | 3 |
| 59 | 18 | 3 |
| 60 | 12 | 3 |
| 61 | 10 | 3 |
| 62 | 9.6 | 3 |
| 63 | 9.4 | 3 |
| 64 | 9.35 | 3 |
| 65 | 9.2 | 3 |
| 66 | 9.1 | 3 |
| 67 | 8.25 | 3 |
| 68 | 7.83 | 3 |
| 69 | 7.7 | 3 |
| 70 | 6.8 | 3 |
| 71 | 6.3 | 3 |
| 72 | 6.0 | 3 |
| 73 | 5.8 | 3 |
| 74 | 4.9 | 3 |
| 75 | 3.9 | 3 |
| 76 | 3.6 | 3 |
| 77 | 3.5 | 3 |
| 78 | 3.0 | 3 |
| 79 | 2.65 | 3 |
| 80 | 2.5 | 3 |
| 81 | 1.5 | 3 |
| 82 | 1.2 | 3 |
| 83 | 1.1 | 3 |
| 84 | 1.0 | 3 |
| 85 | .5 | 3 |
| 86 | 1865 | 0 |
| 87 | 522 | 3 |
| 88 | 146 | 3 |
| 89 | 610 | 3 |
| 90 | 2005 | 0 |
| 91 | 2025 | 0 |
| 92 | .6 | 0 |
| 93 | .75 | 3 |
| 94 | .4 | 3 |
| 95 | 30.87 | 3 |
| 96 | 32.7 | 3 |
| 97 | 36.71 | 3 |
| 98 | 41.2 | 3 |
| 99 | 43.65 | 3 |
| 100 | 49 | 3 |
| 101 | 500 | 0 |
| 102 | 1850 | 0 |
| 103 | 450 | 0 |
| 104 | 440 | 0 |

-continued

| CODE | FREQUENCY | GATE |
|---|---|---|
| 105 | 428 | 0 |
| 106 | 660 | 0 |
| 107 | 589 | 0 |
| 108 | 555 | 0 |
| 109 | 333 | 0 |
| 110 | 14 | 0 |
| 111 | 15 | 3 |
| 112 | 2000 | 0 |
| 114 | 999 | 0 |
| 115 | .67 | 0 |
| 116 | 770+wobble | 0 |
| 117 | 780+wobble | 0 |
| 118 | 1570 | 0 |
| 119 | 1770 | 0 |
| Auto 2 | 804.1 | 3 |
| 120 | 804.1 | |
| 121 | 805.6 | 3 |
| 122 | 807.23 | 3 |
| 123 | 808.79 | 3 |
| 124 | 810.35 | 3 |
| 125 | 811.91 | 3 |
| 126 | 813.48 | 3 |
| 126 | 815.04 | 3 |
| 127 | 816.60 | 3 |
| 128 | 818.16 | 3 |
| 129 | 819.73 | 3 |
| 130 | 821.288 | 3 |
| Auto 3 | 822.75 | |
| 131 | 822.75 | |
| 132 | 824.22 | |
| 133 | 825.69 | |
| 134 | 827.16 | |
| 135 | 828.63 | |
| 136 | 830.10 | |
| 137 | 831.57 | |
| 138 | 833.04 | |
| 139 | 834.51 | |
| 140 | 835.98 | |
| 141 | 837.463 | |
| Auto 4 | 838.85 | |
| 142 | 838.85 | |
| 143 | 840.24 | |
| 144 | 841.63 | |
| 145 | 843.02 | |
| 146 | 844.41 | |
| 147 | 845.80 | |
| 148 | 847.19 | |
| 149 | 848.58 | |
| 150 | 849.96 | |
| 151 | 851.35 | |
| 152 | 852.749 | |
| 153 | 854.07 | |
| 154 | 855.38 | |
| 155 | 856.71 | |
| 156 | 858.02 | |
| 157 | 859.34 | |
| 158 | 860.66 | |
| 159 | 861.98 | |
| 160 | 863.30 | |
| 161 | 864.62 | |
| 162 | 865.94 | |
| 163 | 867.254 | |
| Auto 6 | 868.51 | |
| 164 | 868.51 | |
| 165 | 869.77 | |
| 166 | 871.02 | |
| 167 | 872.28 | |
| 168 | 873.53 | |
| 169 | 874.79 | |
| 170 | 876.04 | |
| 171 | 877.30 | |
| 172 | 878.55 | |
| 173 | 879.81 | |
| 174 | 881.07 | |
| Auto 7 | 882.265 | |
| 175 | 882.265 | |
| 176 | 883.465 | |
| 177 | 884.664 | |

-continued

| CODE | FREQUENCY | GATE |
|---|---|---|
| 178 | 885.863 | |
| 179 | 887.063 | |
| 180 | 888.262 | |
| 181 | 889.461 | |
| 182 | 890.661 | |
| 183 | 891.860 | |
| 184 | 893.060 | |
| 185 | 894.259 | |
| Auto 8 | 895.407 | |
| 186 | 895.407 | |
| 187 | 896.555 | |
| 188 | 897.703 | |
| 189 | 898.851 | |
| 190 | 899.999 | |
| 191 | 901.147 | |
| 192 | 902.295 | |
| 193 | 903.443 | |
| 194 | 904.591 | |
| 195 | 905.739 | |
| 196 | 906.887 | |
| Auto 9 | 907.989 | |
| 197 | 907.898 | |
| 198 | 909.091 | |
| 199 | 910.193 | |
| 200 | 911.295 | |
| 201 | 912.397 | |
| 202 | 913.499 | |
| 203 | 914.602 | |
| 204 | 915.704 | |
| 205 | 916.806 | |
| 206 | 917.908 | |
| 207 | 919.010 | |
| Auto 10 | 920.071 | |
| 208 | 920.071 | |
| 209 | 921.132 | |
| 210 | 922.192 | |
| 211 | 923.253 | |
| 212 | 924.314 | |
| 213 | 925.374 | |
| 214 | 926.435 | |
| 215 | 927.496 | |
| 216 | 928.556 | |
| 217 | 929.617 | |
| 218 | 930.677 | |
| Auto 11 | 960.211 | |
| 219 | 960.211 | |
| 220 | 989.744 | |
| 221 | 1019.27 | |
| 222 | 1048.81 | |
| 223 | 1078.34 | |
| 224 | 1107.88 | |
| 225 | 1137.41 | |
| 226 | 1166.94 | |
| 227 | 1196.48 | |
| 228 | 1226.01 | |
| 229 | 1255.54 | |
| 230 | 1285.08 | |
| 231 | 1314.61 | |
| 232 | 1344.14 | |
| 233 | 1373.68 | |
| 234 | 1403.21 | |
| 235 | 1432.74 | |
| 236 | 1462.28 | |
| 237 | 1491.81 | |
| 238 | 1521.34 | |
| 239 | 1550.88 | |
| 240 | 1580.41 | |
| 241 | 1609.94 | |
| 242 | 1639.48 | |
| 243 | 1669.01 | |
| 244 | 1698.54 | |
| 245 | 1728.08 | |
| 246 | 1757.61 | |
| 247 | 1787.14 | |
| 248 | 1816.68 | |
| Auto 12 | 646711 | |
| 249 | 646711 | |
| 250 | 647640 | |

-continued

| CODE | FREQUENCY | GATE |
|---|---|---|
| 251 | 648569 | |
| 252 | 649498 | |
| 253 | 650427 | |
| 254 | 651356 | |
| 255 | 652285 | |
| 256 | 653214 | |
| 257 | 654143 | |
| 258 | 655072 | |
| 259 | 656002 | |
| 260 | 656931 | |
| 261 | 657859 | |
| 262 | 658789 | |
| 263 | 659718 | |
| 264 | 660647 | |
| 265 | 661576 | |
| 266 | 662505 | |
| 267 | 663434 | |
| 268 | 664363 | |
| 269 | 665292 | |
| 270 | 666221 | |
| 271 | 667150 | |
| 272 | 668079 | |
| 273 | 669009 | |
| 274 | 669938 | |
| 275 | 670887 | |
| 276 | 671796 | |
| 277 | 672725 | |
| 278 | 673653 | |
| 279 | 674583 | |
| Auto 13 | 674583 | |
| 280 | 674583 | |
| 281 | 675477 | |
| 282 | 676371 | |
| 283 | 677265 | |
| 284 | 678159 | |
| 285 | 679053 | |
| 286 | 679947 | |
| 287 | 680841 | |
| 288 | 681735 | |
| 289 | 682629 | |
| 290 | 683523 | |
| 291 | 684417 | |
| 292 | 685311 | |
| 293 | 686206 | |
| 294 | 687100 | |
| 295 | 687994 | |
| 296 | 688888 | |
| 297 | 689782 | |
| 298 | 690676 | |
| 299 | 691570 | |
| 300 | 692464 | |
| 301 | 693358 | |
| 302 | 694252 | |
| 303 | 695146 | |
| 304 | 696040 | |
| 305 | 696934 | |
| 306 | 697828 | |
| 307 | 698722 | |
| 308 | 699616 | |
| 309 | 700510 | |
| 310 | 701404 | |
| Auto 14 | 702265 | |
| 311 | 702265 | |
| 312 | 703126 | |
| 313 | 703987 | |
| 314 | 704848 | |
| 315 | 705709 | |
| 316 | 706570 | |
| 317 | 704432 | |
| 318 | 708292 | |
| 319 | 709153 | |
| 320 | 710015 | |
| 321 | 710876 | |
| 322 | 711737 | |
| 323 | 712598 | |
| 324 | 713459 | |
| 325 | 714320 | |
| 326 | 715181 | |

| CODE | FREQUENCY | GATE |
|---|---|---|
| 327 | 716042 | |
| 328 | 716903 | |
| 329 | 717764 | |
| 330 | 718625 | |
| 331 | 719486 | |
| 332 | 720347 | |
| 333 | 721209 | |
| 334 | 722070 | |
| 335 | 722931 | |
| 336 | 723792 | |
| 337 | 724653 | |
| 338 | 725514 | |
| 339 | 726375 | |
| 340 | 727236 | |
| Auto 15 | 728067 | |
| 341 | 728067 | |
| 342 | 728898 | |
| 343 | 729730 | |
| 344 | 730562 | |
| 345 | 731393 | |
| 346 | 732225 | |
| 347 | 733056 | |
| 348 | 733888 | |
| 349 | 734719 | |
| 350 | 735551 | |
| 351 | 736382 | |
| 352 | 737214 | |
| 353 | 738045 | |
| 354 | 738876 | |
| 355 | 739708 | |
| 356 | 740539 | |
| 357 | 741371 | |
| 358 | 742202 | |
| 359 | 743034 | |
| 360 | 743865 | |
| 361 | 744697 | |
| 362 | 745528 | |
| 363 | 746360 | |
| 364 | 747191 | |
| 365 | 748022 | |
| 366 | 748854 | |
| 367 | 749686 | |
| 368 | 750517 | |
| 369 | 751349 | |
| 370 | 752180 | |
| Auto 16 | 752985 | |
| 371 | 752985 | |
| 372 | 753790 | |
| 373 | 754594 | |
| 374 | 755399 | |
| 375 | 756203 | |
| 376 | 757009 | |
| 377 | 757813 | |
| 378 | 758618 | |
| 379 | 759423 | |
| 380 | 760227 | |
| 381 | 761032 | |
| 382 | 761836 | |
| 383 | 762641 | |
| 384 | 763446 | |
| 385 | 764251 | |
| 386 | 765055 | |
| 387 | 765860 | |
| 388 | 766665 | |
| 389 | 767470 | |
| 390 | 768275 | |
| 391 | 769079 | |
| 392 | 769884 | |
| 393 | 770688 | |
| 394 | 771494 | |
| 395 | 772298 | |
| 396 | 773103 | |
| 397 | 773907 | |
| 398 | 774712 | |
| 399 | 775517 | |
| 400 | 776322 | |
| Auto 17 | 777103 | |
| 401 | 777103 | |
| 402 | 777883 | |
| 403 | 778663 | |
| 404 | 779444 | |
| 405 | 780224 | |
| 406 | 781005 | |
| 407 | 781785 | |
| 408 | 782565 | |
| 409 | 783346 | |
| 410 | 784126 | |
| 411 | 784906 | |
| 412 | 785687 | |
| 413 | 786468 | |
| 414 | 787248 | |
| 415 | 788028 | |
| 416 | 788809 | |
| 417 | 789590 | |
| 418 | 790370 | |
| 419 | 791151 | |
| 420 | 791931 | |
| 421 | 792711 | |
| 422 | 793492 | |
| 423 | 794272 | |
| 424 | 795053 | |
| 425 | 795833 | |
| 426 | 796613 | |
| 427 | 797394 | |
| 428 | 798175 | |
| 429 | 798955 | |
| 430 | 799735 | |
| Auto 18 | 800493 | |
| 431 | 600493 | |
| 432 | 801251 | |
| 433 | 802010 | |
| 434 | 802768 | |
| 435 | 803526 | |
| 436 | 804284 | |
| 437 | 805042 | |
| 438 | 805801 | |
| 439 | 806559 | |
| 440 | 807317 | |
| 441 | 808075 | |
| 442 | 808833 | |
| 443 | 809592 | |
| 444 | 810350 | |
| 445 | 811108 | |
| 446 | 811866 | |
| 447 | 812624 | |
| 448 | 813383 | |
| 449 | 814141 | |
| 450 | 814899 | |
| 451 | 815657 | |
| 452 | 816415 | |
| 453 | 817174 | |
| 454 | 817932 | |
| 455 | 818690 | |
| 456 | 819448 | |
| 457 | 820207 | |
| 458 | 820965 | |
| 459 | 821723 | |
| 460 | 822481 | |
| Auto 19 | 823217 | |
| 461 | 823217 | |
| 462 | 823953 | |
| 463 | 824688 | |
| 464 | 825424 | |
| 465 | 826160 | |
| 466 | 826896 | |
| 467 | 827632 | |
| 468 | 828367 | |
| 469 | 829103 | |
| 470 | 829839 | |
| 471 | 830575 | |
| 472 | 831310 | |
| 473 | 832046 | |
| 474 | 832782 | |
| 475 | 833518 | |
| 476 | 834254 | |
| 477 | 834989 | |

-continued

| CODE | FREQUENCY | GATE |
|---|---|---|
| 478 | 835725 | |
| 479 | 836461 | |
| 480 | 837197 | |
| 481 | 837932 | |
| 482 | 838668 | |
| 483 | 839404 | |
| 484 | 840140 | |
| 485 | 840876 | |
| 486 | 841611 | |
| 487 | 842347 | |
| 488 | 843083 | |
| 489 | 843819 | |
| 490 | 844554 | |
| Auto 20 | 845276 | |
| 491 | 845276 | |
| 492 | 845997 | |
| 493 | 846718 | |
| 494 | 847439 | |
| 495 | 848160 | |
| 496 | 848881 | |
| 497 | 849603 | |
| 498 | 850324 | |
| 499 | 851045 | |
| 500 | 851776 | |
| 501 | 852487 | |
| 502 | 853208 | |
| 503 | 853929 | |
| 504 | 854651 | |
| 505 | 855372 | |
| 506 | 856093 | |
| 507 | 856814 | |
| 508 | 857535 | |
| 509 | 858256 | |
| 510 | 858978 | |
| 511 | 859699 | |
| 512 | 860420 | |
| 513 | 861141 | |
| 514 | 861862 | |
| 515 | 862583 | |
| 516 | 863304 | |
| 517 | 864026 | |
| 518 | 864747 | |
| 519 | 865468 | |
| 520 | 866189 | |
| 521 | | |
| 522 | | |
| 523 | | |

Figure 5A:
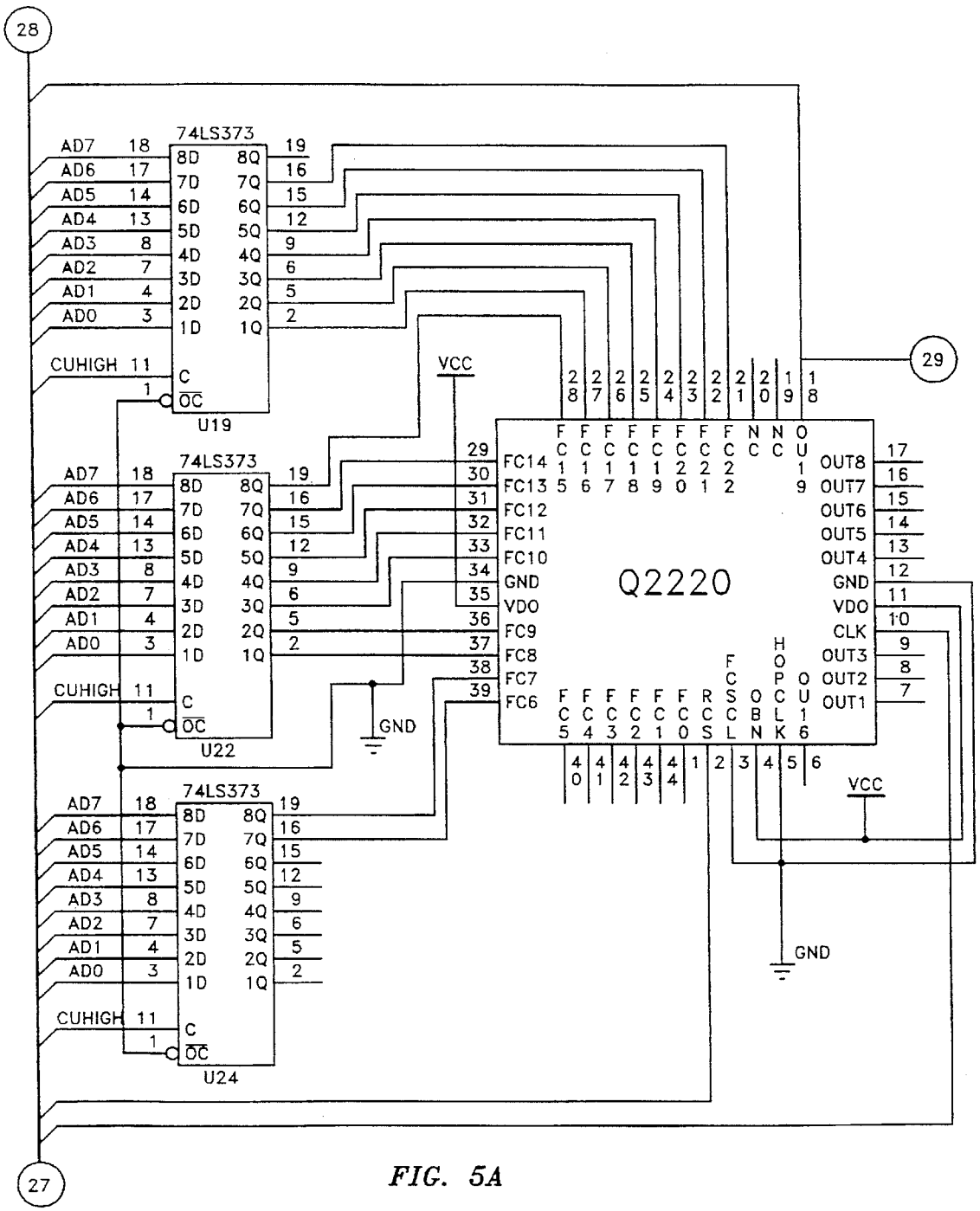
FIG. 5a and b combined is a schematic diagram of primarily the frequency synthesizer of FIG. 1.
Figure 5B:
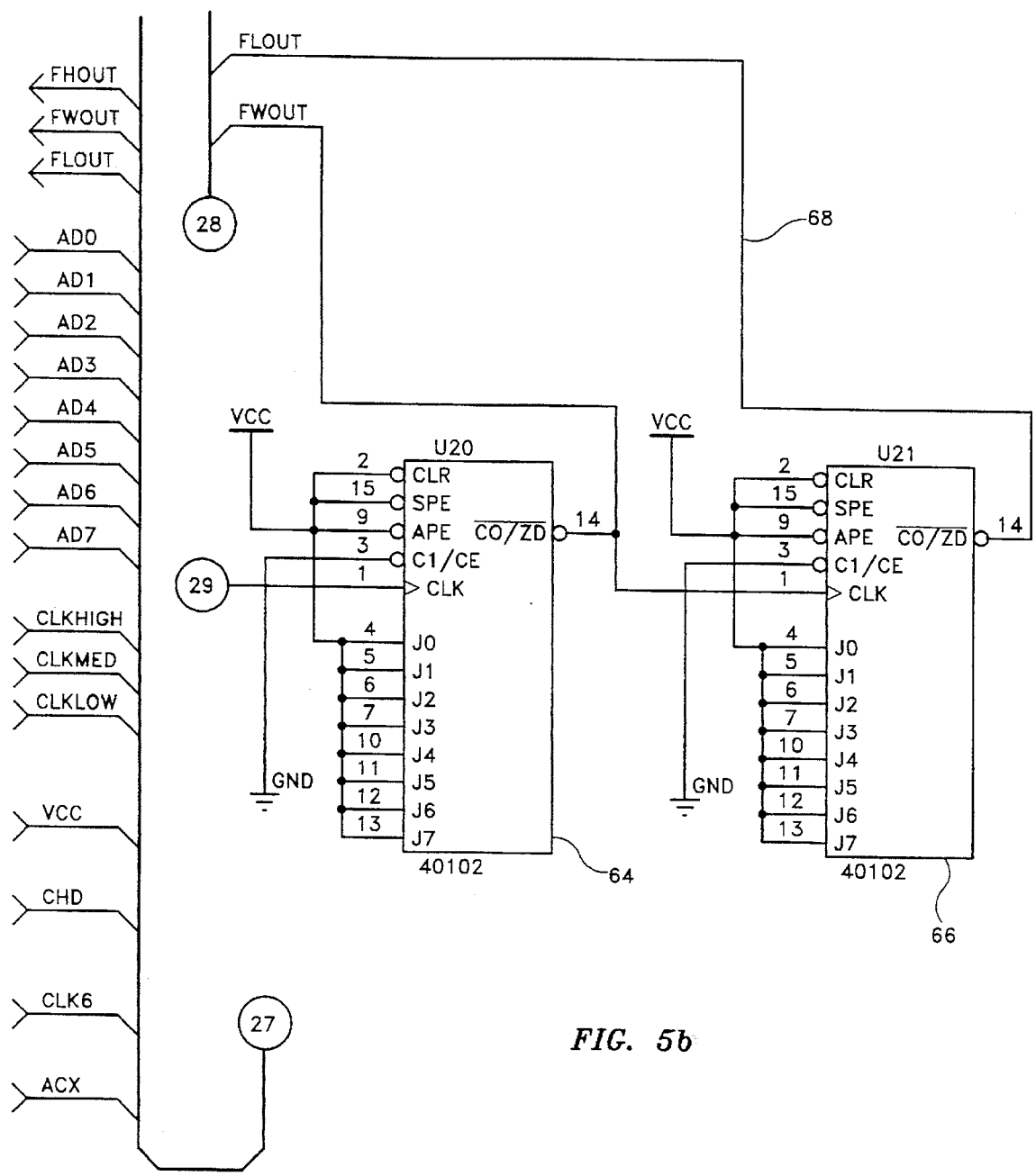

Referring now to FIG. 5A and 5B, it will be seen that the frequency synthesizer means 12 generally includes an integrated circuit 54 provided by a Q220 DDS IC made by Qualcomm. The input data for the control word for the frequency synthesizer circuit 54 is input by means of three eight bit latches 56, 58 and 60. The 23 bit frequency control word provided by the latches 56,58, and 60 instructs the frequency synthesizer circuit to generate a specific frequency having a frequency resolution of 0.715 Hz. on output 62. Resolution of the frequency signal thus generated is increased further by dividing it by a first Divide by 100 counter 64, a 28C64-15/L counter made by Phillips, and then by a second similar Divide by 100 counter 66. The output 68 of counter 66 is then input to a Divide by 2 flip-flop 70 in FIG. 4a–4i to ensure a 50% duty cycle for the resultant precise frequency output signal on output 72. The precise frequency output signal thus has a range, in the illustrated embodiment, of around 0.00004 Hz to 3 Mhz.

Referring now to FIG. 3a–3e it will be seen that actuation of a key of the keyboard set 18 provides a particular interrupt control signal to the controller 74 where it is stored. The controller is an integrated circuit Model 74C923 made by National Semiconductor Co. The control signal stored in controller 74 is then read by the microcontroller in FIG. 4a–4i. The microcontroller 16 is an Intel P80C31BH IC controller. The microcontroller 16 operates through a bus controller 76, a Phillips PCF8584 controller, which has the ability to operate in both master and slave modes to communicate with the 4 digit display 21 in FIG. 3a–3e to display information representative of the particular frequency output signal that has been chosen by a user of the system 10 or which is presently running on the system. The microcontroller 76 also communicates similarly with the 4 digit display 23 in FIG. 3a–3c to display the time remaining for a specific frequency signal to continue to be generated and the particular pulse ON period for that specific frequency signal. The 4 digit display 23 is provided by display circuits 78 and 80 under the control of a suitable display controller 82, a Phillips SAA1064 controller. The display circuits are HDSP-A011 units made by Hewlett Packard.

The display 23 is provided by Hewlett Packard HDSP-A011 units 84,86,88, and 90 under the control of a display controller 92, a Phillips SAA1064 controller. The LED 52 and the LED 44 are activated under the control of the microcontroller 16, as seen in FIG. 3. Also, in FIG. 3a–3f it will be seen that the pulse time switch 44 of the keyboard means and the voltage control 50 of the keyboard communicate with the microcontroller 16 in FIG. 4a–4i.

Referring again to FIG. 4a–4i, the programmable memory 14 of the system 10 is provided by a first programmable memory 94, an EPROM model NM27C512Q-150 made by National Semiconductor, and a second programmable memory 96, an EEPROM model 28C64A-15/L made by Microchip. The first programmable memory 94 stores the control signals for the preprogrammed sequences of frequency signals that may be accessed by a user actuating a particular control number or channel number that is representative of a particular sequence of frequencies. The programmable memory 96 contains control signals that may be accessed by a user when selecting a particular specific precise frequency signal or when creating a particular customized sequence of specific frequency signals for application.

A first decoder 98 and a second decoder 100 communicate with the programmable control means 14 and cooperate with a suitable digital to analog converter circuit 102 to provide analog signals to the R-C circuit 104 formed by resistance 106 and capacitor 108 to provide the one second delay between ON periods in certain specific frequency signals as heretofore described.

The circuit 110 includes the resistor 112 and the capacitor 114 and provides the soft start circuit 34 that upon commencement of a specific precise frequency signal gradually ramps up the output signal from zero to a predetermined value at a constant predetermined rate.

A speaker 116 is included in the audio circuit 118 to provide an auditory signal to a user of the system 10 upon the initiation of each specific precise frequency signal whether singly or part of a sequence. The decoder 120 provides address DEMUX and the integrated circuit 122 acts as a receiver to clean up signals received from the keyboard to preclude erroneous signals from key bounce for example. Reference character 124 refers to an integrated circuit that provides multiplexing of the data bus for the particular integrated circuits chosen for implementation of the system 10. The circuit generally designated by 126 controls the slew rate of the pulses. A suitable user port 128 is provided for further applications of the amplified output signal beyond the particular spaced electrode means illustrated in the previously described Figures.

Figure 7:
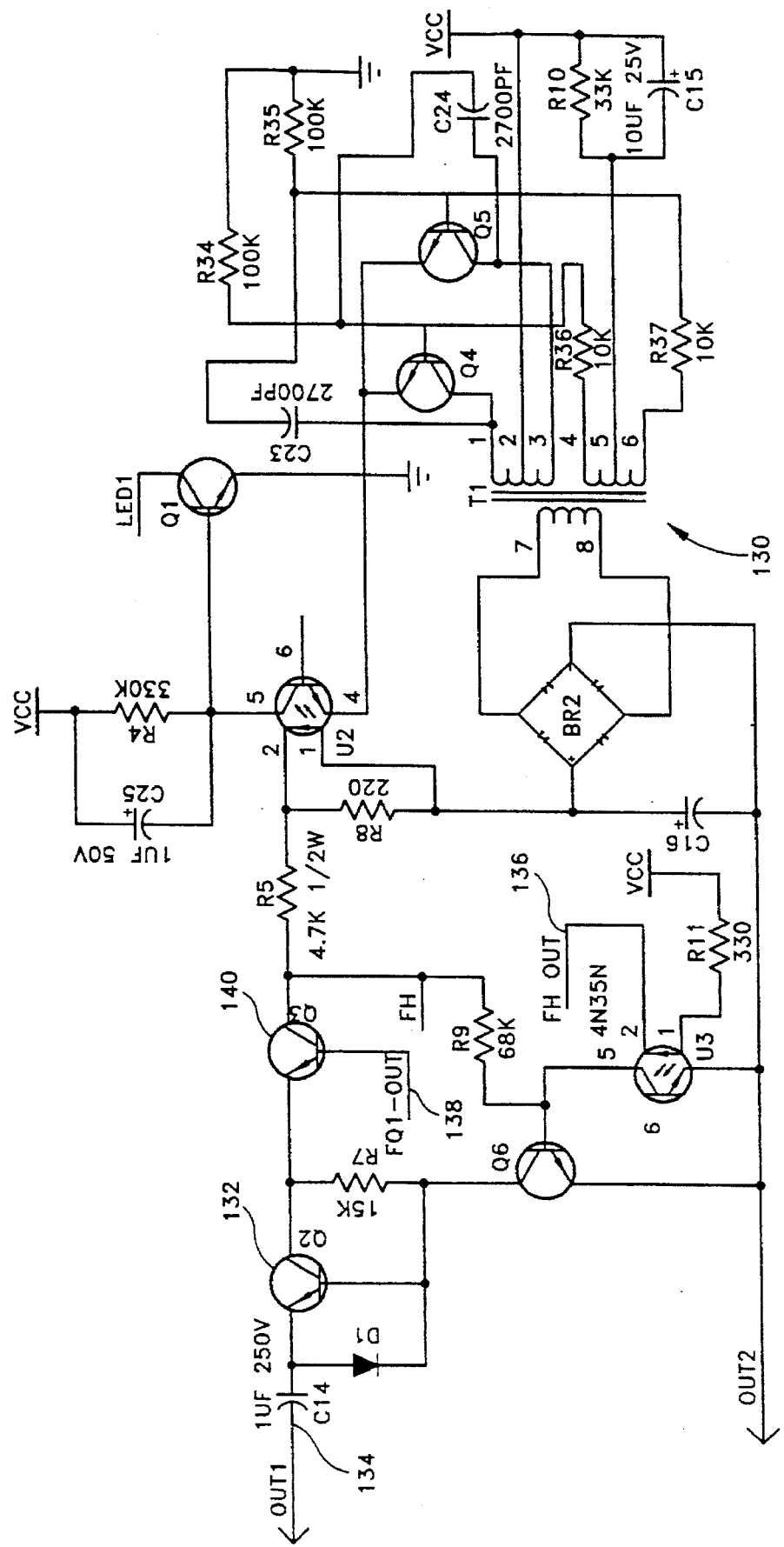
FIG. 7 is a schematic diagram of primarily the output circuit of the system.

Referring now to FIG. 7, the output circuit 22 is illustrated. A transformer coupled inverter 130 generates around 100 V DC. Isolation of the output is accomplished by means of the transformer 17 and optically coupling signals to the output circuit which includes the emitter follower 132 and the output capacitor 134. The specific precise frequency signal including such OFF intervals as may be interposed appears on lead 136 and is optically coupled to the emitter follower 132 for control thereof. The output level of the amplified frequency signal is determined by the control signal 138 established by the intensity control 50 and for present purposes may be considered not to exceed a level of around 50 volts. The control signal 138 controls a series pass transistor 140.

Figure 8:
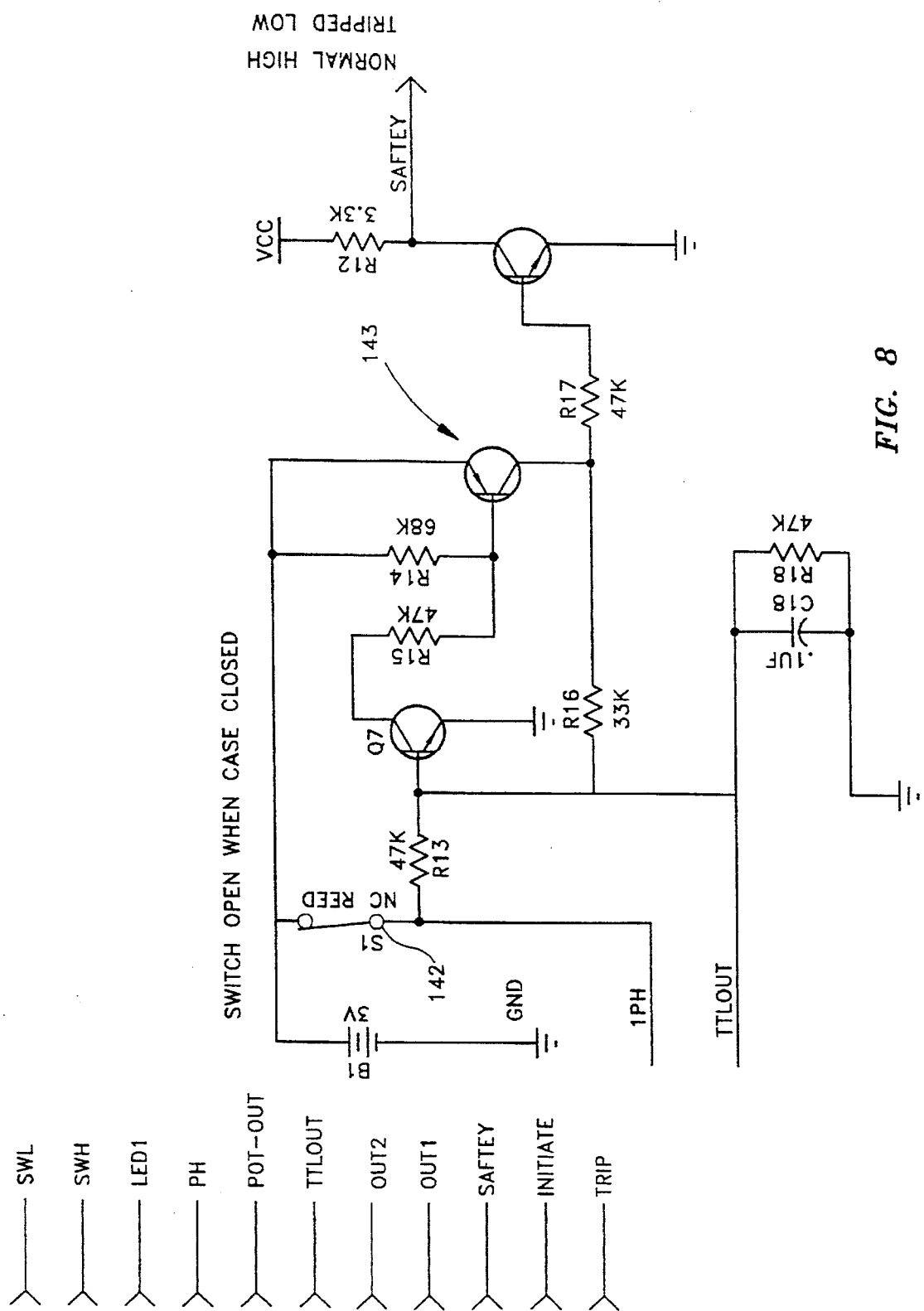
FIG. 8 is a schematic diagram of primarily the security circuit of the system.

FIG. 8 illustrates the security circuit 22 and includes a normally open reed relay 142 that is configured in such a manner so as to detect any opening of the enclosure 26. Any momentary contact of the relay 142 causes a flip-flop 143 to be set to Low when tripped. A Low signal for the flip-flop 144 is directed to the microcontroller 16 to disable the system 10 until the system is reset by an authorized party.

Figure 6A:
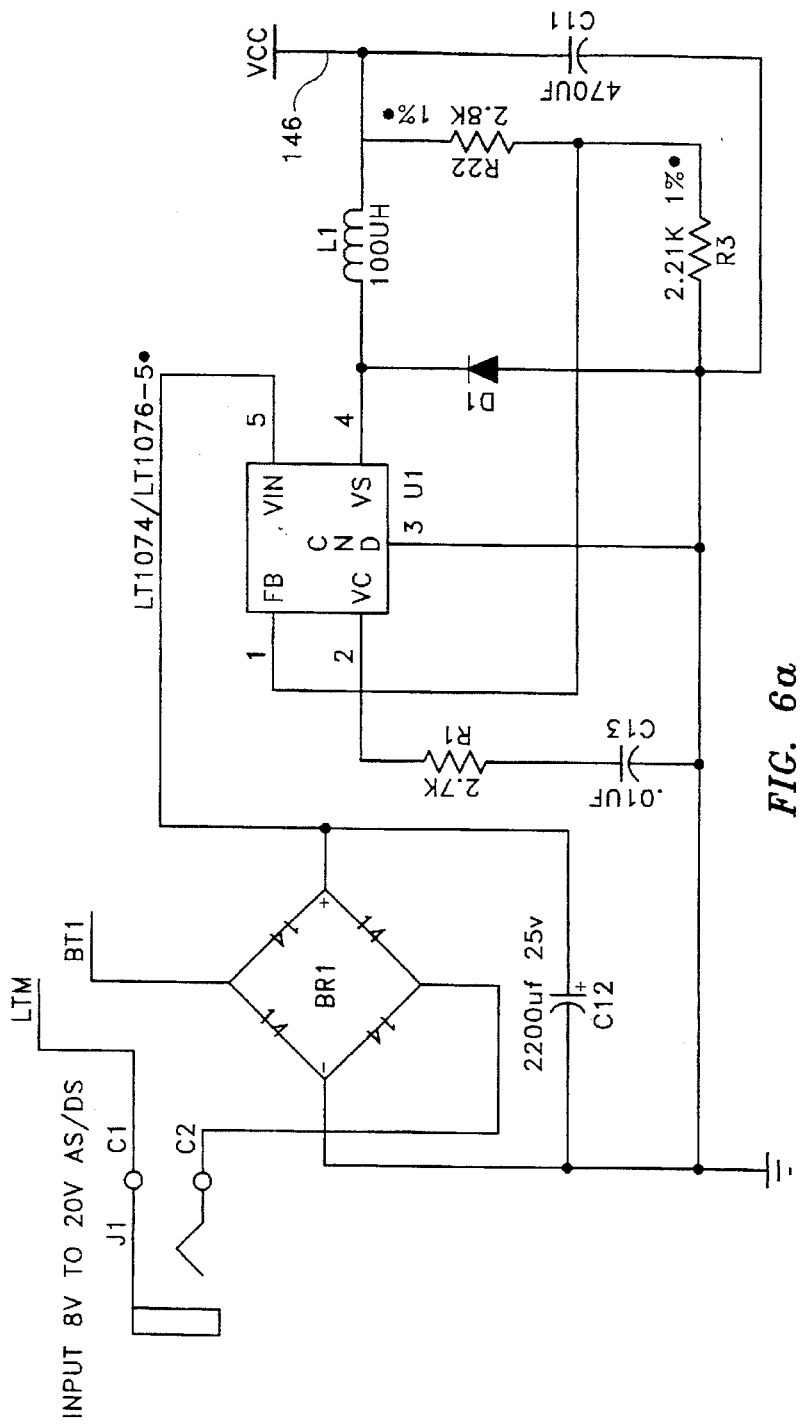
FIG. 6a is a schematic diagram of primarily the input power supply of the system.
Figure 6B:
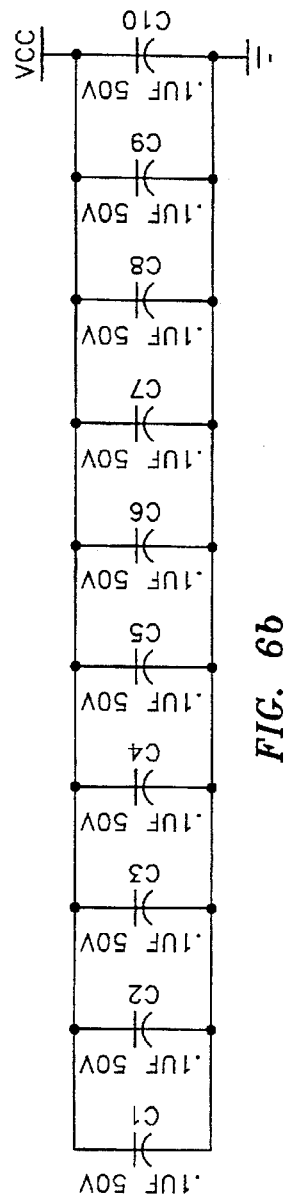
FIG. 6b is a schematic diagram of another aspect of the power supply shown in FIG. 1.

FIG. 6a and 6b illustrate the power supply 40 which supplies power to all components of the system 10. The power supply is a conventional buck converter capable of operation from 7 to 20 V DC or AC. The voltage VCC appears on lead 146 and is +5 V. FIG. 6b is a further depiction of charging capacitors to maintain VCC during usage.

From the foregoing, it is apparent that the present invention provides a novel system and method for generating a plurality of specific precise bio-active frequencies and sequences of such frequencies for appropriate applications such as health science, industrial and other commercial uses. The term "health science applications" should be considered broadly and not limiting as the bio-active frequency generator of the present invention may also be used for such applications as destroying micro-organisms such as are found in water supplies and in various oil supplies.

Changes may be made in the combination and arrangement of parts or elements as heretofore set forth in the specification and shown in the drawings, it being understood that changes may be made in the precise embodiment disclosed without departing from the spirit and scope of the invention as defined in the following claims.

What is claimed is:

1. A system to generate an output signal having a predetermined precise frequency and particularly adapted for use in applications including health science and industrial uses, comprising:

frequency generation means responsive to a control signal to generate an output signal having a predetermined precise frequency within a frequency range from at least 0.00004 Hz to 3 Mhz;

said frequency generation means includes a frequency synthesizer means, and a programmable memory means coupled to the keyboard means whereby actuation of the keyboard means to generate a signal representative of a predetermined frequency selected from the memory means for application to the frequency synthesizer means to cause such frequency synthesizer means to generate the selected predetermined precise frequency, keyboard means coupled to the frequency generation means and actuable to generate a control signal representative of a predetermined frequency; said keyboard means is actuable to store within the memory means instructions representative of a sequence of predetermined precise frequencies whereby n number of frequencies can be generated serially upon command, display means coupled to the keyboard means for displaying information representative of actuation of the keyboard means and the output signal;

gating means coupled to the frequency generation means and responsive to the specific precise frequency being generated to permit selective control of the generated frequency signal;

output means coupled to the frequency generation means to amplify the voltage of the generated frequency signal to a predetermined level, and application means coupled to the output means for application of the output signal for applications including health science and industrial uses the shape of said output signal is a square wave having a 50% duty cycle.

2. The system as defined in claim 1 wherein the frequency of the output signal has an accuracy of at least 0.001 Hz.

3. The system as defined in claim 1 wherein a plurality of sets of instructions that are representative of a predetermined series of predetermined frequency output signals are stored within the programmable memory means whereby actuation of the keyboard means selects a particular set of instructions for application to the frequency synthesizer means for generation of a selected output signal having a series of predetermined frequencies.

4. The system as defined in claim 1 wherein said frequency of said generated signal comprises a selected frequency in cycles per second from the group of specific frequencies for inactivating microorganisms and viruses which may be present and enhancing specific tissue regeneration in a mammal, said group of frequencies and the purpose therefor consisting of Adynamia, geriatric 60, 27.5; Abdominal inflammation 380, 1.2, 2727, 2489, 2170, 1800, 1600, 2302, 880, 832, 787, 776, 727, 465, 444, 1865, 146, 125, 95, 72, 20, 450, 440, 428, 660, 589, 2000, 1570, 1770, 805.6, 811.91; Abdominal pain 3.0, 440, 95, 160, 26, 522, 146, 555, 333, 999, 10000, 3040, 1865, 125, 95, 72; Abscesses 2720, 2170, 880, 787, 727, 190, 500; Acidosis 10000, 880, 802, 787, 776, 727, 20, 146; Acne 2720, 2170, 1800, 1600, 1500, 880, 787, 727; Actinomycosis 465, 10000, 787, 727, 20; Acupuncture disturbance field 18; Acute Pain 160, 26, 3040, 95, 522, 146, 555, 333, 999, 10000, 880, 787, 727, 690, 666; Adenoids 1550, 802, 880, 787, 776, 727, 444, 20, 428, 660, 589, 333, 14, 2000, 770, 780, 805.6, 808.79, 2720, 2170; Adhesions 2720, 2170, 1550, 802, 880, 787, 776, 760, 727, 190; Adrenal stimulant 20; Allergy 10000, 3.0 and 330, 522, 146, 555, 333, 999, 125, 95, 72, 20, 444, 1865; Alopecia 10000, 880, 787, 727, 465, 146; Amenorrhea 444, 522, 146, 555, 333, 999, 125, 95, 72, 880, 10000, 3040, 787, 760, 727, 20; Anal itching 465, 444, 125, 95, 72, 444, 186, 20, 2000, 522, 146, 555, 333, 999, 10000, 880, 787, 760, 727; Angina 787, 776, 727, 465, 428, 660, 589, 333, 14, 2000, 780, 1570, 1770, 805.6; Ankylosing spondylitis 3040, 95, 3352, 880, 787, 776, 727, 1875, 28, 1.2, 10, 35, 28, 7.7, 1.2, 110, 100, 60, 808.79, 428, 660, 333, 14, 2000; Antiseptic effect 2352, 880, 787, 760, 727, 465, 444, 450, 428, 660, 589, 555, 333, 14, 2000, 1570, 1770; Apoplexy 40, 20, 1800, 1875, 125, 95, 72, 20, 2309, 522, 146, 555, 333, 999, 880, 787, 727; Appetite, lack of 465, 2309, 125, 95, 72, 20, 10000, 880, 787, 727; Arteriosclerosis 10000, 2720, 2170, 1800, 1600, 1500, 880, 787, 776, 727, 20, 808.79; Arthritis, 10000, 1550, 880, 802, 787, 727, 28, 20, 7.7, 3.0, 1.2; Arthritis, rheumatoid of the muscles and tendons 250, 1.2, 1875, 787, 727, 808.79; Arthritis, arthrosis and parathyroid disturbances affecting calcium metabolism, 9.6; Arthritis, arthralgia due to gout, 9.4; Arthritis focal origin 9.4; Asthma, 2720, 2170, 1800, 1600, 1500, 880, 787, 727, 808.79; Astrocytoma 9.2, 8.25, 7.7, 2170, 2127, 880, 690, 666; Ataxia 2720, 2170, 1800, 1600, 1500, 880, 787, 776, 727, 650, 625, 600, 2309, 125, 95, 72, 20, 805.6, 811.91, spastic ataxia, 9.2, 8.25, 7.7; Athlete's Foot 465, 1550, 880, 802, 727, 20, Autoimmune Disorders 10000, 3352, 880, 787, 776, 727, 650, 625, 600, 465, 250, 28, 20, 9.6, 9.4, 7.7, 3.0, 522, 146, 1850; Auto-intoxication 0.5, 522, 146, 10000, 880, 787, 727, 20, 555, 333, 999; Back pain 26, 186, 3040, 522, 146, 555, 333, 999, 10000, 760, 2352, 880, 787, 727; Bad Breath 2352, 880, 787, 727, 20; Bedsores 880, 2352, 787, 727, 485 followed by 1.2 and 73; Biliousness 2352, 10000, 880, 832, 787, 727, 465; Bladder and prostate complaints 880, 2352, 787, 727, 465, 20, 9.4 Boils 880, 2352, 787, 727, 465, 660, 589, 333; Bone trauma 380, 2352, 10000, 880, 787, 727; Bone/periodontal disease 47.5, 1800, 1600, 1875, 880, 787, 776, 727; Bone protuberance 1.2 and 250; Brachial Neuralgia 0.5; Breast 880, 2352, 787, 776, 3083; Bright's Syndrome 1500, 880, 787, 727; Bronchial asthma 0.5, 522, 146, 125, 95, 72, 966, 20; Bronchitis 880, 727, 9.4, 9.35; Bronchial Pneumonia 2352, 880, 787, 776, 727; Bubonic Plague 500, plus secondary infections: 880, 787, 727, 20; Burns 190, 10000, 880, 787, 727, 465, 200; Bursitis 880, 787, 727; Cancer 465, 2127, 880, 787, 3083, 589; Cardiac Edema 9.2; Carpal Tunnel Syndrome 1550 thru 465, 6.3, 148, 2.5, 727, 522, 146, 444; Cataract 10000, 880, 787, 727; Catarrh 1550, 802, 880, 787, 727, 444, 20; Cerebral Palsy 880, 787, 727, 522, 146; Chicken Pox 2352, 1800, 1600, 1500, 880, 787, 727, 20; Cholera 880, 802, 450, 880, 787, 727; Chronic Fatigue Syndrome 10000, 2720, 1800, 880, 802, 787, 776, 727, 465, 966, 330, 148, 125, 95, 73, 72, 35, 27.5, 20, 6.3, 4.9, 428, 660; Circulatory stasis 40; Circulation disturbance problems 40, 9.4; Concentration 7.83; Cold in head, chest 10,000, 1550, 880, 802, 787, 776, 727, 444, 20; Colic 1550, 832, 802, 787, 727, 20; Colitis 1550, 880, 832, 802, 440; Constipation 1550, 880, 802, 787, 776, 727, 20; Convulsions 10,000, 880, 787, 727; Contusions 9.1, 110; Costalgia 160, 26, 3040, 880, 787, 727, 10,000, 2353; Cramps 10,000, 880, 787, 727, 26; Cystitis (of urinary bladder) 1550, 880, 802, 787, 727, 465, 20; Deafness 10,000, 1550, 880, 802, 787, 727, 20; Dental foci 3040, 95, 190, 47.5, 1600, 1550, 2353, 1500, 880, 832, 787, 776, 760, 727, 1316, 1916, 465, 2720, 2489, 1800, 522, 146, 555, 333, 999; Depression, anxiety, trembling, weakness 3.5; Depression 35, 220, 1.1, 73; Detoxification 6.3, 148, 2.5, 727, 522, 146, 444, 666, 428, 880, 787, 555, 333, 999; Diabetes 837, 260, 1885, 125, 95, 1957, 522, 428, 49.4 for secondary diabetes infections 10,000, 2720, 2170, 1880, 1550, 880, 802, 727, 465, 20; Diabetic loading 35, 700; Diarrhea/Dysentery 1550, 880, 802, 787, 727, 465; Distorsion 9.1, 110; Dizziness 5.8; Dupuytren's Contracture 1.2, 250; Dysmenorrhea 26, 4.9, 2352, 880, 787, 727, 465; Dyspepsia 1550, 880, 802, 787, 727; Ears 9.2, 880, 787, 727, 20; Eczema 9.2, 1550, 802, 787, 727; Eczema 9.4; Enuresis 10,000, 880, 787, 727, 465; Edema 522, 146, 154.3, 444, 440, 880, 787, 727, 465; Epicondylitis 251.2, 3040, 160, 26; Epididymitis 1500, 880, 787, 7827, 20; Epilepsy 10,000, 880, 802, 787, 727, 700, 650, 600, 125, 20; Epstein-Bart 428, 660, 776, 465, 880, 787, 727; Erysipelas 660, 2000, 10,000, 880, 787, 727, 465, 20; Erythema nosodum 9.4; Esophagus 880, 787, 727; Eustachian tube inflammation 1550, 880, 802, 787, 776, 727, 465; Eye inflammation 1.2, 80; Eye Disorders 1600, 10,000, 880, 787, 727, 20; Eyes 1600, 880, 787, 727; Facial paralysis 10,000, 880, 787, 727; Fatigue 2720, 1800, 428, 660, 465, 125, 95, 72, 27.5, 20, 2309; Fever 880, 787, 727, 20; Fibroma 2127, 2008, 727, 690, 666, 1550, 802, 465; Fibrosis of lung 457.5; Fistulal ulcer 880, 832, 787, 727; Flashes, hot (complications) 10,000, 880, 787, 727; Flatulence 1550, 880, 802, 787, 760, 727, 465; Flu 1550, 880, 802, 787, 727, 20; Foot (blisters) 10,000, 880, 787, 727, 600; Fractures 450, 10,000, 880, 787, 727; Frostbite 880, 787, 727; Frozen shoulder 10,000, 880, 802, 787, 727; Fungal infection 465, 1550, 880, 802, 727, 20; Furunkulosis herpes, skin diseases 1200, 1550, 802, 2000, 787, 727; Gall bladder dystonia with osteitis 2.6, 3040, 880, 787, 727, 29; Gallstones 2.65, 3040, 880, 787, 727, 20; Gangrene 880, 787, 727, 20, 73; Gas (intestinal) 1550, 880, 802, 787, 760, 727, 465; Gastritis and flatus 880, 832, 787, 727, 20; Gout 9.4, 3040, 880, 787, 727, 20; Gravel in urine 2.6, 3040, 880, 787, 727, 20; Gums (inflammation, gingivitis, pyorrhea) 1550, 880, 802, 787, 727, 465, 20; Hair loss 10,000, 880, 787, 727, 465, 146; Hallucinations 10,000, 880, 787, 727, 20; Hangover 10,000, 146, 610; Hay Fever 880, 787, 727, 20; Headaches 160, 10, 6.3, 522, 146, 4.9, 3040, 727, 148, 125, 95, 72, 20, 10, 5.8, 2.5, 444, 685, 880, 787, 650, 625, 600, 3040, 428, 660, 555, 333, 999; For headaches caused by parasites 160, 125, 95, 73, 20, 727, 3040; Headaches (urogenitaiiy caused) 160, 9.4, 3040, 555, 333, 999, 160, 9.6, 3040; Head Injuries 160, 9.6, 3040, 880, 787, 727, 522, 72, 5.8, 4.9; Hearing problems 10,000, 2158, 880, 787, 760, 727, 20; Heart (lab animals only) 80, 160, 20, 73, 3.9, 10,000, 880, 787, 727, 465, 4125 95, 20; Heartburn 832, 2720, 2170, 2127, 1800, 1600, 2352, 1500, 880, 787, 727, 685, 465, 2309, 125, 95, 72, 20; Hemorrhage 1550, 802; Hemorrhoids 1550, 880, 802, 727; Hepatitis (generic)29.2, 1550, 880, 802, 727; Hernia 10,000, 787, 727; Herpes (zoster) 2720, 2170, 1800, 1600, 1500, 1550, 802, 1865,880, 787, 727, 20; High blood pressure 10,000, 880, 787, 727, 9.2; Hip Pain (as in coxarthritis) 3040, 880, 787, 727, 160, 26; Hives 1800, 880, 787, 727, 522, 146, 4.9; Hoarseness 880, 760, 727; Hyperacidity of stomach 7.83 on solar plexus and 230 on stomach; Hydrocele 880, 787, 727; Hyperosmia 20, 10,000, 522, 1865, 810.35; Hyperthyroid 3.0, 0.5; Hypoacidity of stomach 15, 20; Hypothyroid 12, 35; Hypertension 20, 95, 9.2, 6.0, 10,000, 880, 787, 727; Hypertension, spastic 95; Impotence 9.4, 2127, 2008, 465, 880, 802, 787, 2083, 125, 95, 73, 72, 20, 1875; Indigestion 10,000, 880, 787, 727, 465, 444, 20, 125, 95, 72, 4.9; Infantile Paralysis 1500, 880, 787, 727; Infections 1600, 1550, 1500, 880, 832, 802, 787, 776, 760, 727, 700, 690, 666, 650, 625, 600, 465, 444, 125, 95, 72, 20, 1865, 500, 450, 440, 428, 660; Infertility 2127, 2008, 465, 880, 802, 787, 2083, 1875, 9.4; Inflammation 1.5; influenza 1550, 802, 1500, 880, 787, 727, 20; Insomnia 3.6, 3.0, 1550, 1500, 880, 802; Intercostal neuralgia 3040, 160, 26, 1550, 880, 802, 787, 776, 727, 125, 20, 1865, 444; Intermittent claudication 45, 48; Itching 880, 787, 727, 465, 444, 125, 95, 72, 7.83, 2309, 2000; Jaundice 1600, 1550, 1500, 880, 802, 650, 625, 600, 2309, 146, 250, 125, 95, 72, 20; Kidney insufficiency 50, 440, 1600, 1550, 1500, 880, 802, 787, 727, 650, 625, 600, 465, 73, 40, 10, 2309, 522, 146, 250, 148, 125, 95, 72, 20, 555, 333, 999; Knee/Joint pain 3040, 160, 26, 1550, 880, 802, 787, 727, 28, 20, 7.7, 3.0, 1.2, 250, 1.2, 9.6, 9.4; Larynx 440, 465, 444, 1550, 880, 802, 787, 727, 28, 7.7, 3.0, 1.2, 250, 1.2, 9.6, 9.4; Leprosy 600, 1600, 1550, 1500, 880, 832, 802, 787, 776, 760, 727, 700, 690, 666, 650, 625, 600, 465, 444, 20, 500, 450, 440, 428, 660; Leukemia 2127, 2008, 880, 787, 727, 690, 666, 589; Leukoderma 880, 787, 727, 444, 20, 589, 2000; Locomotor Dysfunction 10,000, 880, 787, 776, 727, 650, 625, 600, 2309, 125, 95, 72, 20; convulsions, spasticity 28, 8.25, 7.7; Low Blood Pressure 880, 787, 727, 20; Lumbago 880, 787, 727, 125, 95, 72, 2309, 9.2, 8.25, 7.7; Lungs 1550, 802, 880, 787, 776, 727, 125, 95, 72, 20, 2309, 450, 589; Lupus Erythematosus 880, 787, 727, 776, 1850; Luxation 119.1; Lymph stasis 154.3, 2.5, 727, 522, 146, 444, 428, 880, 787; Malaria 555; Measles 333; Mental Disorders 444, 148, 20, 6.3, 2.5, 522, 146, 10,000, 125, 95, 72, 4.9, 727, 428, 444, 465 to 1550; Menieres Disease 2352, 880, 787, 727, 465, 428, 589, 333; Meningitis 2352, 880, 832, 787, 727, 650, 625, 600, 465, 2309, 125, 95, 72, 20, 428, 660; Menstrual problems 26, 3040, 880, 787, 727, 465, 160, 20; Migraine 170; Motion Sickness 650, 625, 600, 465, 444, 1865, 522, 146, 125, 95, 72, 20; Mouth eruptions 465, 2127, 2008, 727, 690, 666; Herpes sores 2489, 1800, 465, 1550, 1500, 880, 787, 727, 1850, 428; Mucous membrane inflammation 380; Multiple Sclerosis use auto immune frequencies plus 880, 787, 727; Muscles, to relax 760, 6.8; Muscular Dystrophy 10,000, 2352, 880, 787, 776, 727, 650, 625, 600, 465, 250, 28, 20, 9.6, 9.4, 7.7, 3.0, 522, 610, 1850, 146, 555, 333, 999; Muscular pain 3040, 26, 160, 320, 250, 240, 80, 40, 10, 5.8, 2.5, 1.5, 1.2, 1.0, 0.5; Muscle pain from parasites 2309, 125, 811, 108, 72, 20; Mumps 10,000, 727, 2720, 2489, 2127, 2008, 14, 428, 880, 787, 727, 20; Nausea 880, 832, 787, 727, 20, 4.9; Nephritis\nephrosis 880, 787, 727, 10, 40, 73, 465; Nervousness 3.0; Nerve disorders 10,000, 2720, 2489, 2170, 1800, 1600, 2352, 880, 787, 148, 6.3, 2.5, 522, 610, 727, 650, 625, 600, 125, 95, 72, 20, 428, 660, 333; Neuralgia 3.9, 555, 333, 999; Neurosis 28; Nose infection, congestion 2352, 880, 787, 776, 727, 444, 440, 465, 20; Numbness 10,000, 2720, 2489, 2170, 1800, 1600, 2352, 880, 787, 727, 650, 625, 600, 440, 660, 333; Oral Lesions 2720, 2489, 2008, 1800, 1600, 2352, 880, 787, 776, 760, 727, 465, 444, 522, 146, 555, 333, 999; Orchitis 2720, 2489, 1800, 2127, 2008, 1800, 1600, 2352, 1500, 880, 832, 787, 776, 2083, 650, 625, 600, 125, 95, 72, 20, 14; Osteomyelitis 2.6, 2720, 2489, 2170, 2127, 2008, 1800, 1600, 2352, 1500, 880, 832, 787, 776, 2083; Otosclerosis 9.2; Ovarian disorders 1875, 465, 444, 26, 2720, 2489, 2170, 2127, 2008, 1800, 1600, 2352, 1500, 880, 832, 787, 776, 2083, 20; Pain 3040, 95, 160, 26; Pain of infection 3040, 160, 26, 95, 880, 2352, 787, 776, 727, 4.9; Pain of cancer 3040, 160, 26, 95, 2127, 2008, 2083; Pancreatic insufficiency 15, 10, 250, 1875, 465, 444, 26, 2720, 2489, 2170, 2127, 2008, 1800, 1600, 2352, 1500, 880, 832, 787, 776, 2083, 20; Paralysis, spastic 10,000, 880, 787, 776, 727, 650, 625, 600, 2309, 125, 95, 72, 20, 7.7; Paralysis, nonspastic 10,000, 880, 787, 776, 727, 650, 625, 600, 444, 1865, 125, 95, 72, 20, 9.2, 8.25; Parasites 125, 95, 72, 20, 2309; Pelvic Inflammatory Disease 2720, 2489, 2170, 2127, 2008, 1800, 1600, 2352, 787, 776, 2083, 650, 625, 600, 465, 966, 95, 72, 450, 428, 14, 589, 1570; Pericarditis 2720, 2170, 1600, 880, 2352, 787, 760, 727, 625, 465, 160, 125, 73, 26, 20, 3.9, 95, 80, 73, 72, 2309; Pharyngitis 440, 589, 380, 1600, 2352, 776, 787, 880, 727, 20, 522, 146; Pleurisy 1550, 802, 880, 787, 776, 727, 125, 95, 72, 20, 2309, 450, 589; Pneumonia 1550, 802, 880, 787, 776, 727, 20, 450, 589; Poliomyelitis 805.6 secondary complications 2158, 428, 1500, 880, 787, 727; Polyps 2720, 2489, 2170, 2127, 2008, 1800, 1600, 2083, 1875, 465, 444, 20, 522, 146; Pre-op and post-operation prevention and control of nosocomial and idiopathic infection 2170, 1800, 1600, 2352, 1500, 880, 832, 802, 787, 776, 727, 465, 444, 522, 146, 428, 589, 333; Prostatitis 510, 522, 146, 2720, 2489, 2170, 2127, 2008, 2352, 787, 776, 2083, 465, 125, 95, 72, 20, 1249; Prostate complaints 9.4, 2127, 2008, 727, 690, 666, 465, 880, 802, 787, 727, 125, 95, 73, 72, 20; Proritis 880, 787, 727, 465, 444, 125, 95, 72, 20, 2309, 2000; Prostate tumor (malignant) 2127, 2008, 2083; Psychosomatic pain 727, 160, 26, 148, 455, 511, 146, 555, 333, 999; Pyorrhea 2720, 2489, 2008, 1800, 1600, 2352, 880, 787, 776, 727, 465, 444, 522, 146; Rabies 807.23; Raynaud's Disease 727, 20; Rheumatoid arthritis of the muscles and tendons 251.2, 9.6, 9.4, 1875, 10,000, 2352, 880, 787, 727, 465, 20, 7.7, 3.0, 1.2; Rhinitis 10,000, 2352, 1500, 880, 787, 776, 727, 444, 7.83, 522, 146, 465; Sarcoma 2127, 2008, 880, 787, 727, 690, 666, 589; Scars 465 to 1568; Scarlet Fever 880, 787, 727, 1356; Sciatica or Ischia 2352, 880, 787, 727, 690, 666, 10; Sedative Effect 2.5; Sexual Dysfunction 9.4, 2127 2008, 465, 880, 802, 787, 2083, 125, 95, 73, 72, 20, 1875; Shingles 2352, 802, 1800, 1865, 1880, 787, 727, 26; Sinusitis 2352, 880, 787, 727, 125, 72, 522; Sleeping Sickness 124; Slipped discs 26, 125, 880, 787, 333, 787, 727, 95, 72, 522, 146, 555, 333, 999; Smallpox 811.91, 1550, 802, 880, 787, 727; Sneezing 880, 787, 727, 465, 146; Sore Throat 2720, 2489, 1800, 1600, 2352, 880, 787, 776, 727, 465, 589, 808.79; Spasms, muscle 6.8; Spastic paresis 650, 625, 30.87,48; Spleen, enlarged 35, 787, 10,000, 2720, 2170, 1800, 1550, 880, 802, 727, 465, 20; Spondylitis, acute 1.2, 10, 7.7, 28; Staphylococci infection 727; Stiff neck 4.9; Spastic stiff neck 9.2, 6.0; Stiff muscles in general 320, 250, 240, 160, 125, 80, 40, 20, 10, 5.8, 2.5, 1.5, 1.2, 1.0, 0.5, 1890, 2352, 880, 787, 776, 727; Stomach disorders 2127, 2008, 880, 787, 727, 2083, 125, 95, 72, 20, 3.9, 450, 1570, 1770; Stones 3.5; Streptococci infection 880; Streptothrix infection 787; Sty 10,000, 880, 787, 727, 20; Subluxation induced disorders 9.6; Sun Allergy 3.0, 330; Sunstroke 444, 428, 190, 3040, 95, 522, 146, 880, 20; Surgery—Prevention and control of nosocomial and idiopathic infection 2170, 1800 1600, 2352, 1500, 880, 832, 802, 787, 776, 727, 465, 444, 522, 146, 428, 589, 333, 3040, 95, 160, 26, 544; Swelling 522, 146, 6.3, 148, 444, 428, 880, 787, 727; Swollen glands 880, 787, 727, 20; Syphilis 1875; Tachycardia (also used for pain of arthritis, headache, Tut-na, and facial toning) 1.2; Teeth 3040, 95, 190, 47.5, 1600, 2352, 1500, 880, 10,000, 2489, 787, 776, 760, 727, 1875, 465, 2720, 2489, 1800; Tendo myopathy 3040, 320, 250, 160, 80, 40, 26, 20, 10, 5.8, 2.5, 1.5, 1.2, 1.0, 0.5, 522, 146; Tetanus 811.91, 600, 880, 787, 727; Thrush 465; Tonsillitis 74.2, 73, 2352, 1500, 880, 832, 787, 776, 727, 1875, 465, 808.79, 589; Toothache 3040, 95, 190, 47.5, 2720, 2489, 1800, 1600, 2352, 1500, 880, 832, 787, 776, 727, 666, 650, 600, 465, 522, 146, 555, 333, 999; Tooth extraction, afterward 3040, 95, 47.5, 7.83; Toxins 444, 160, 522, 146, 555, 333, 999, 10,000, 880, 787, 727, 125, 95, 72, 20; Trauma 3040, 95, 190, 760, 880, 787, 727, 465; Trench Mouth 1875, 880, 787, 776,727,650, 625, 465; Trigeminal neuralgia 2720, 2489, 2170, 1890, 1600, 2352, 880, 832, 787, 776, 760, 727, 650, 146, 7.83, 27.5, 428, 660, 589, 333, 999, 770, 2000, 805.6, 807.23, 811.91, 810.35; Tuberculosis 2352, 1875, 776, 2127, 2008, 465, 589; Typhoid 1570, 1770, 2352, 690, 1800; Ulcers 2489, 2170, 2127, 1800, 1600, 880, 832, 802, 787, 776, 727, 1.2 through 5.8, 1.2, 73; Urethritis 2720, 2170, 2127, 1800, 1600, 2352, 1500, 880, 832, 787, 776, 727, 1875, 455, 2309, 125, 95, 72, 1.2; Urticaria 1800, 444, 125, 95, 72, 522, 146, 787, 727, 6.3; Varicoses 1.2, 28; Vegetative Dystonia 40; Vein thrombosis 685; Vertigo 60, 5.8; Warts 3040, 5, 2170, 2127, 2008, 1800, 1600, 1500, 2083; Worms 125, 95, 6.0, 20, 2309; Wound healing 880, 787, 727, 220, 190, 20, 40; Yeast infection 465; Yellow Fever 999; Scan brain for troubled areas 7.83; For relaxation 4.9; To stimulate mental clarity 12; Facial toning 9.6; Kidney meridian 9.2.

5. The system as defined in claim 1 wherein at least one set of instructions that is representative of a predetermined series of predetermined frequency output signals is stored within the programmable memory means whereby actuation of the keyboard means selects that set of instructions for application to the frequency synthesizer means for generation of an output signal having a series of predetermined frequencies.

6. The system as defined in claim 5 wherein the system further includes an audio means that is responsive to the termination of a frequency signal in an output signal to create an audible signal prior to initiation of an immediately succeeding frequency signal in the output signal.

7. The system as defined in claim 1 wherein the output means further includes circuit means that is responsive to receipt of the output signal to increase the amplitude of the output signal from zero to its ultimate amplitude at a predetermined rate.

8. The system as defined in claim 7 wherein the keyboard means is actuable to provide a control signal to the output means to control the amplitude of the voltage of the output signal.

9. The system as defined in claim 1 wherein the system further includes spaced electrode means connected to the output means for applications including health science and industrial uses.

10. The system as defined in claim 9 wherein the spaced electrode means includes a pair of electrically conductive elements adapted to be held in the hands of a user of the system.

11. The system as defined in claim 1 wherein the gating means that gates the generated precise frequency signal ON and OFF for predetermined periods of time comprising means controllable by manual actuation of the keyboard means by a user of the system.

12. The system as defined in claim 11 wherein the gating means is variable to vary the gated periods of time.

13. The system as defined in claim 12 wherein the gating means is variable to gate the generated precise frequency signal OFF for a period of at least one second and to gate such frequency signal ON for a period exceeding one second.

14. The system as defined in claim 12 wherein the gating means is variable to gate the generated precise frequency signal OFF for a predetermined time period and to gate such frequency signal ON for a period from about one to seven seconds.

15. The system as defined in claim 14 wherein the information displayed by the display means includes a representation of the particular precise frequency signal then being generated by the frequency generation means and the specific ON period then being interposed between OFF periods for such signal by the variable gating means.

16. The system as defined in claim 15 wherein the information being displayed by the display means further includes a representation of the time remaining of a preprogrammed time period for a specific precise frequency signal to be generated by the frequency signal generating means.

17. A system to generate an output signal a predetermined precise frequency and particularly adapted for use in applications including health science and industrial by a user, comprising:

means responsive to a control signal to generate an output signal having a precise frequency, said output signal is an alternating square wave and comprises a signal selectable from a range of signal frequencies from at least 0.00004 Hz to 100 Hz;

control means coupled to the precise frequency generating means and operative to generate a determinable control signal selected by a user;

means responsive to the specific frequency signal generated to determine whether to selectively pulse the generated frequency signal ON and OFF in a predetermined sequence;

variable output means coupled to the precise frequency signal generating means to amplify the voltage of the generated signal to a determinable predetermined level, and application means coupled to the output means for application of the amplified output signal for uses including health science by a user.

18. The system as defined by claim 17 wherein the precise frequency output signal is an alternating square wave having a 50% duty cycle and is selectable from a range of 100 Hz. to 3 Mhz.

19. The system as defined by claim 17 wherein the elements of the system, other than the coupled application means, are enclosed within a separable enclosure, and the system further includes a security means that upon separation of such enclosure disables the system from further operation.

20. The system as defined in claim 20 wherein the frequency of said generated signal comprises a selected frequency in cycles per second from a group of specific frequencies for inactivating microorganisms and viruses which may be present and enhancing specific tissue regeneration in a mammal, said group of frequencies and the purpose therefore consisting of Adynamia, geriatric 60, 27.5; Abdominal inflammation 380, 1.2, 2727, 2489, 2170, 1800, 1600, 2302, 880, 832, 787, 776, 727, 465, 444, 1865, 146, 125, 95, 72, 20, 450, 440, 428, 660, 589, 2000, 1570, 1770, 805.6, 811.91; Abdominal pain 3.0, 440, 95, 160, 26, 522, 146, 555, 333, 999, 10000, 3040, 1865, 125, 95, 72; Abscesses 2720, 2170, 880, 787, 727, 190, 500; Acidosis 10000, 880, 802, 787, 776, 727, 20, 146; Acne 2720, 2170, 1800, 1600, 1500, 880, 787, 727; Actinomycosis 465, 10000, 787, 727, 20; Acupuncture disturbance field 18; Acute Pain 160, 26, 3040, 95, 522, 146, 555, 333, 999, 10000, 880, 787, 727, 690, 666; Adenoids 1550, 802, 880, 787, 776, 727, 444, 20, 428, 660, 589, 333, 14, 2000, 770, 780, 805.6, 808.79, 2720, 2170; Adhesions 2720, 2170, 1550, 802, 880, 787, 776, 760, 727, 190; Adrenal stimulant 20; Allergy 10000, 3.0 and 330, 522, 146, 555, 333, 999, 125, 95, 72, 20, 444, 1865; Alopecia 10000, 880, 787, 727, 465, 146; Amenorrhea 444, 522, 146, 555, 333, 999, 125, 95, 72, 880, 10000, 3040, 787, 760, 727, 20; Anal itching 465, 444, 125, 95, 72, 444, 186, 20, 2000, 522, 146, 555, 333, 999, 10000, 880, 787, 760, 727; Angina 787, 776, 727, 465, 428, 660, 589, 333, 14, 2000, 780, 1570, 1770, 805.6; Ankylosing spondylitis 3040, 95, 3352, 880, 787, 776, 727, 1875, 28, 1.2, 10, 35, 28, 7.7, 1.2, 110, 100, 60, 808.79, 428, 660, 333, 14, 2000; Antiseptic effect 2352, 880, 787, 760, 727, 465, 444, 450, 428, 660, 589, 555, 333, 14, 2000, 1570, 1770; Apoplexy 40, 20, 1800, 1875, 125, 95, 72, 20, 2309, 522, 146, 555, 333, 999, 880, 787, 727; Appetite, lack of 465, 2309, 125, 95, 72, 20, 10000, 880, 787, 727; Arteriosclerosis 10000, 2720, 2170, 1800, 1600, 1500, 880, 787, 776, 727, 20, 808.79; Arthritis, 10000, 1550, 880, 802, 787, 727, 28, 20, 7.7, 3.0, 1.2; Arthritis, rheumatoid of the muscles and tendons 250, 1.2, 1875, 787, 727, 808.79; Arthritis, arthrosis and parathyroid disturbances affecting calcium metabolism, 9.6; Arthritis, arthralgia due to gout, 9.4; Arthritis focal origin 9.4; Asthma, 2720, 2170, 1800, 1600, 1500, 880, 787, 727, 808.79; Astrocytoma 9.2, 8.25, 7.7, 2170, 2127, 880, 690, 666; Ataxia 2720, 2170, 1800, 1600, 1500, 880, 787, 776, 727, 650, 625, 600, 2309, 125, 95, 72, 20, 805.6, 811.91, spastic ataxia, 9.2, 8.25, 7.7; Athlete's Foot 465, 1550, 880, 802, 727, 20, Autoimmune Disorders 10000, 3352, 880, 787, 776, 727, 650, 625, 600, 465, 250, 28, 20, 9.6, 9.4, 7.7, 3.0, 522, 146, 1850; Autointoxication 0.5, 522, 146, 10000, 880, 787, 727, 20, 555, 333, 999; Back pain 26, 186, 3040, 522, 146, 555, 333, 999, 10000, 760, 2352, 880, 787, 727; Bad Breath 2352, 880, 787, 727, 20; Bedsores 880, 2352, 787, 727, 485 followed by 1.2 and 73; Biliousness 2352, 10000, 880, 832, 787, 727, 465; Bladder and prostate complaints 880, 2352, 787, 727, 465, 20, 9.4 Boils 880, 2352, 787, 727, 465, 660, 589, 333; Bone trauma 380, 2352, 10000, 880, 787, 727; Bone/periodontal disease 47.5, 1800, 1600, 1875, 880, 787, 776, 727; Bone protuberance 1.2 and 250; Brachial Neuralgia 0.5; Breast 880, 2352, 787, 776, 3083; Bright's Syndrome 1500, 880, 787, 727; Bronchial asthma 0.5, 522, 146, 125, 95, 72, 966, 20; Bronchitis 880, 727, 9.4, 9.35; Bronchial Pneumonia 2352, 880, 787, 776, 727; Bubonic Plague 500, plus secondary infections: 880, 787, 727, 20; Burns 190, 10000, 880, 787, 727, 465, 200; Bursitis 880, 787, 727; Cancer 465, 2127, 880, 787, 3083, 589; Cardiac Edema 9.2; Carpal Tunnel Syndrome 1550 thru 465, 6.3, 148, 2.5, 727, 522, 146, 444; Cataract 10000, 880, 787, 727; Catarrh 1550, 802, 880, 787, 727, 444, 20; Cerebral Palsy 880, 787, 727, 522, 146; Chicken Pox 2352, 1800, 1600, 1500, 880, 787, 727, 20; Cholera 880, 802, 450, 880, 787, 727; Chronic Fatigue Syndrome 10000, 2720, 1800, 880, 802, 787, 776, 727, 465, 966, 330, 148, 125, 95, 73, 72, 35, 27.5, 20, 6.3, 4.9, 428, 660; Circulatory stasis 40; Circulation disturbance problems 40,9.4; Concentration 7.83; Cold in head, chest 10,000, 1550, 880, 802, 787, 776, 727, 444, 20; colic 1550, 832, 802, 787, 727, 20; Colitis 1550, 880, 832, 802, 440; Constipation 1550, 880, 802, 787, 776, 727, 20; Convulsions 10,000, 880, 787, 727; Contusions 9.1, 110; Costalgia 160, 26, 3040, 880, 787, 727, 10,000, 2353; Cramps 10,000, 880, 787, 727, 26; Cystiris (of urinary bladder) 1550, 880, 802, 787, 727, 465, 20; Deafness 10,000, 1550, 880, 802, 787, 727, 20; Dental foci 3040, 95, 190, 47.5, 1600, 1550, 2353, 1500, 880, 832, 787, 776, 760, 727, 1316, 1916, 465, 2720, 2489, 1800, 522, 146, 555, 333, 999; Depression, anxiety, trembling, weakness 3.5; Depression 35, 220, 1.1, 73; Detoxification 6.3, 148, 2.5, 727, 522, 146, 444, 666, 428, 880, 787, 555, 333, 999; Diabetes 837, 260, 1885, 125, 95, 1957, 522, 428, 49.4 for secondary diabetes infections 10,000, 2720, 2170, 1800, 1550, 880, 802, 727, 465, 20; Diabetic loading 35, 700; Diarrhea/Dysentery 1550, 880, 802, 787, 727, 465; Distortion 9.1, 110; Dizziness 5.8; Dupuytren's Contracture 1.2, 250; Dysmenorrhea 26, 4.9, 2352, 880, 787, 727, 465; Dyspepsia 1550, 880, 802, 787, 727; Ears 9.2, 880, 787, 727, 20; Eczema 9.2, 1550, 802, 787, 727; Eczema 9.4; Enuresis 10,000, 880, 787, 727, 465; Edema 522, 146, 154.3, 444, 440, 880, 787, 727, 465; Epicondylitis 251.2, 3040, 160, 26; Epididymitis 1500, 880, 787; 7827, 20; Epilepsy 10,000, 880, 802, 787, 727, 700, 650, 600, 125, 20; Epstein-Bart 428, 660, 776, 465, 880, 787, 727; Erysipelas 660, 2000, 10,000, 880, 787, 727, 465, 20; Erythema nosodum 9.4; Esophagus 880, 787, 727; Eustachian tube inflammation 1550, 880, 802, 787, 776, 727, 465; Eye inflammation 1.2, 80; Eye Disorders 1600, 10,000, 880, 787, 727, 20; Eyes 1600, 880, 787, 727; Facial Paralysis 10,000, 880, 787, 727; Fatigue 2720, 1800, 428, 660, 465, 125, 95, 72, 27.5, 20, 2309; Fever 880, 787, 727, 20; Fibroma 2127, 2008, 727, 690, 666, 1550, 802, 465; Fibrosis of lung 457.5; Fistulal Ulcer 880, 832, 787, 727; Flashes, hot (complications) 10,000, 880, 787, 727; Flatulence 1550, 880, 802, 787, 760, 727, 465; Flu 1550, 880, 802, 787, 727, 20; Foot (blisters) 10,000, 880, 787, 727, 600; Fractures 450, 10,000, 880, 787, 727; Frostbite 880, 787, 727; Frozen shoulder 10,000, 880, 802, 787, 727; Fungal infection 465, 1550, 880, 802, 727, 20; Furunkulosis herpes, skin diseases 1200, 1550, 802, 2000, 787, 727; Gall bladder dystonia with osteitis 2.6, 3040, 880, 787, 727, 20; Gallstones 2.65, 3040, 880, 787, 727, 20; Gangrene 880, 787, 727, 20, 73; Gas (intestinal) 1550, 880, 802, 787, 760, 727, 465; Gastritis and flatus 880, 832, 787, 727, 20; Gout 9.4, 3040, 880, 787, 727, 20; Gravel in urine 2.6, 3040, 880, 787, 727, 20; Gums (inflammation, gingivitis, pyorrhea) 1550, 880, 802, 787, 727, 465, 20; Hair loss 10,000, 880, 787, 727, 465, 146; Hallucinations 10,000, 880, 787, 727, 20; Hangover 10,000, 146, 610; Hay Fever 880, 787, 727, 20; Headaches 160, 10, 6.3, 522, 146, 4.9, 3040, 727, 148, 125, 95, 72, 20, 10, 5.8, 2.5, 444, 685, 880, 787, 650, 625, 600, 3040, 428, 660, 555, 333, 999; For headaches caused by parasites 160, 125, 95, 73, 20, 727, 3040; Headaches (urogenitaiiy caused) 160,' 9.4, 3040, 555, 333, 999, 160, 9.6, 3040; Head Injuries 160, 9.6, 3040, 880, 787, 727, 522, 72, 5.8, 4.9; Hearing problems 10,000, 2158, 880, 787, 760, 727, 20; Heart (lab animals only) 80, 160, 20, 73, 3.9, 10,000, 880, 787, 727, 465, 4125 95, 20; Heartburn 832, 2720, 2170, 2127, 1800, 1600, 2352, 1500, 880, 787, 727, 685, 465, 2309, 125, 95, 72, 20; Hemorrhage 1550, 802; Hemorrhoids 1550, 880, 802, 727; Hepatitis (generic)29.2, 1550, 880, 802, 727; Hernia 10,000, 787, 727; Herpes (zoster) 2720, 2170, 1800, 1600, 1500, 1550, 802, 1865,880, 787, 727, 20; High blood pressure 10,000, 880, 787, 727, 9.2; Hip Pain (as in coxarthritis) 3040, 880, 787, 727, 160, 26; Hives 1800, 880, 787, 727, 522, 146, 4.9; Hoarseness 880, 760, 727; Hyperacidity of stomach 7.83 on solar plexus and 230 on stomach; Hydrocele 880, 787, 727; Hyperosmia 20, 10,000, 522, 1865, 810.35; Hyperthyroid 3.0, 0.5; Hypoacidity of stomach 15, 20; Hypothyroid 12, 35; Hypertension 20, 95, 9.2, 6.0, 10,000, 880, 787, 727; Hypertension, spastic 95; Impotence 9.4, 2127, 2008, 465, 880, 802, 787, 2083, 125, 95, 73, 72, 20, 1875; Indigestion 10,000, 880, 787, 727, 465, 444, 20, 125, 95, 72, 4.9; Infantile Paralysis 1500, 880, 787, 727; Infections 1600, 1550, 1500, 880, 832, 802, 787, 776, 760, 727, 700, 690, 666, 650, 625, 600, 465, 444, 125, 95, 72, 20, 1865, 500, 450, 440, 428, 660; Infertility 2127, 2008, 465, 880, 802, 787, 2083, 1875, 9.4; Inflammation 1.5; Influenza 1550, 802, 1500, 880, 787, 727, 20; Insomnia 3.6, 3.0, 1550, 1500, 880, 802; Intercostal neuralgia 3040, 160, 26, 1550, 880, 802, 787, 776, 727, 125, 20, 1865, 444; Intermittent claudication 45, 48; Itching 880, 787, 727, 465, 444, 125, 95, 72, 7.83, 2309, 2000; Jaundice 1600, 1550, 1500, 880, 802, 650, 625, 600, 2309, 146, 250, 125, 95, 72, 20; Kidney insufficiency 50, 440, 1600, 1550, 1500, 880, 802, 787, 727, 650, 625, 600, 465, 73, 40, 10, 2309, 522, 146, 250, 148, 125, 95, 72, 20, 555, 333, 999; Knee/Joint pain 3040, 160, 26, 1550, 880, 802, 787, 727, 28, 20, 7.7, 3.0, 1.2, 250, 1.2, 9.6, 9.4; Larynx 440, 465, 444, 1550, 880, 802, 787, 727, 28, 7.7, 3.0, 1.2, 250, 1.2, 9.6, 9.4; Leprosy 600, 1600, 1550, 1500, 880, 832, 802, 787, 776, 760, 727, 700, 690, 666, 650, 625, 600, 465, 444, 20, 500, 450, 440, 428, 660; Leukemia 2127, 200.8, 880, 787, 727, 690, 666, 589; Leukoderma 880, 787, 727, 444, 20, 589, 2000; Locomotor Dysfunction 10,000, 880, 787, 776, 727, 650, 625, 600, 2309, 125, 95, 72, 20; convulsions, spasticity 28, 8.25, 7.7; Low Blood Pressure 880, 787, 727, 20; Lumbago 10,000, 880, 787, 727, 125, 95, 72, 2309, 9.2, 8.25, 7.7; Lungs 1550, 802, 880, 787, 776, 727, 125, 95, 72, 20, 2309, 450, 589; Lupus Erythematosus 880, 787, 727, 776, 1850; Luxation 119.1; Lymph stasis 154.3, 2.5, 727, 522, 146, 444, 428, 880, 787; Malaria 555; Measles 333; Mental Disorders 444, 148, 20, 6.3, 2.5, 522, 146, 10,000, 125, 95, 72, 4.9, 727, 428, 444, 465 to 1550; Menieres Disease 2352, 880, 787, 727, 465, 428, 589, 333; Meningitis 2352, 880, 832, 787, 727, 650, 625, 600, 465, 2309, 125, 95, 72, 20, 428, 660; Menstrual problems 26, 3040, 880, 787, 727, 465, 160, 20; Migraine 170; Motion Sickness 650, 625, 600, 465, 444, 1865, 522, 146, 125, 95, 72, 20; Mouth eruptions 465, 2127, 2008, 727, 690, 666; Herpes sores 2489, 1800, 465, 1550, 1500, 880, 787, 727, 1850, 428; Mucous membrane inflammation 380; Multiple Sclerosis use auto immune frequencies plus 880, 787, 727; Muscles, to relax 760, 6.8; Muscular Dystrophy 10,000, 2352, 880, 787, 776, 727, 650, 625, 600, 465, 250, 28, 20, 9.4, 7.7, 3.0, 522, 610, 1850, 146, 555, 333, 999; Muscular pain 3040, 26, 160, 320, 250, 240, 80, 40, 10, 5.8, 2.5, 1.5, 1.2, 1.0, 0.5; Muscle pain from parasites 2309, 125, 811, 108, 72, 20; Mumps 10,000, 727, 2720, 2489, 2127, 2008, 14, 428, 880, 787, 727, 20; Nausea 880, 832, 787, 727, 20, 4.9; Nephritis\nephrosis 880, 787, 727, 10, 40, 73, 465; Nervousness 3.0; Nerve disorders 10,000, 2720, 2489, 2170, 1800, 1600, 2352, 880, 787, 148, 6.3, 2.5, 522, 610, 727, 650, 625, 600, 125, 95, 72, 20, 428, 660, 333; Neuralgia 3.9, 555, 333, 999; Neurosis 28; Nose infection, congestion 2352, 880, 787, 776, 727, 444, 440, 465, 20, Numbness 10,000, 2720, 2489, 2170, 1800, 1600, 2352, 880, 787, 727, 650, 625, 600, 440, 660, 333; Oral Lesions 2720, 2489, 2008, 1800, 1600, 2352, 880, 787, 776, 760, 727, 465, 444, 522, 146, 555, 333, 999; Orchitis 2720, 2489, 2170, 2127, 2008, 1800, 1600, 2352, 1500, 880, 832, 787, 776, 2083, 650, 625, 600, 125, 95, 72, 20, 14; Osteomyelitis 2.6, 2720, 2489, 2170, 2127, 2008, 1800, 1600, 2352, 1500, 880, 832, 787, 776, 2083; Otosclerosis 9.2; Ovarian disorders 1875, 465, 444, 26, 2720, 2489, 2170, 2127, 2008, 1800, 1600, 2352, 1500, 880, 832, 787, 776, 2083, 20; Pain 3040, 95, 160, 26; Pain of infection 3040, 160, 26, 95, 880, 2352, 787, 776, 727, 4.9; Pain of cancer 3040, 160, 26, 95, 2127, 2008, 2083; Pancreatic insufficiency 15, 10, 250, 1875, 465, 444, 26, 2720, 2489, 2170, 2127, 2008, 1800, 1600, 2352, 1500, 880, 832, 787, 776, 2083, 20; Paralysis, spastic 10,000, 880, 787, 776, 727, 650, 625, 600, 2309, 125, 95, 72, 20, 7.7; Paralysis, nonspastic 10,000, 880, 787, 776, 727, 650, 625, 600, 444, 1865, 125, 95, 72, 20, 9.2, 8.25; Parasites 125, 95, 72, 20, 2309; Pelvic Inflammatory Disease 2720, 2489, 2170, 2127, 2008, 1800, 1600, 2352, 787, 776, 2083, 650, 625, 600, 465, 966, 95, 72, 450, 428, 14, 589, 1570; Pericarditis 2720, 2170, 1600, 880, 2352, 787, 760, 727, 625, 465, 160, 125, 73, 26, 20, 3.9, 95, 80, 73, 72, 2309; Pharyngitis 440, 589, 380, 1600, 2352, 776, 787, 880, 727, 20, 522, 146; Pleurisy 1550, 802, 880, 787, 776, 727, 125, 95, 72, 20, 2309, 450, 589; Pneumonia 1550, 802, 880, 787, 776, 727, 20, 450, 589; Poliomyelitis 805.6 secondary complications 2158, 428, 1500, 880, 787, 727; Polyps 2720, 2489, 2170, 2127, 2008, 1800, 1600, 2083, 1875, 465, 444, 20, 522, 146; Pre-op and post-operation prevention and control of nosocomial and idiopathic infection 2170, 1800, 1600, 2352, 1500, 880, 832, 802, 787, 776, 727, 465, 444, 522, 146, 428, 589, 333; Prostatitis 510, 522, 146, 2720, 2489, 2170, 2127, 2008, 2352, 787, 776, 2083, 465, 125, 95, 72, 20, 1249; Prostate complaints 9.4, 2127, 2008, 727, 690, 666, 465, 880, 802, 787, 727, 125, 95, 73, 72, 20; Proritis 880, 787, 727, 465, 444, 125, 95, 72, 20, 2309, 2000; Prostate tumor (malignant) 2127, 2008, 2083; Psychosomatic pain 727, 160, 26, 148, 455, 511, 146, 555, 333, 999; Pyorrhea *2720, 2489, 2008, 1800, 1600, 2352, 880, 787, 776, 727, 465, 444, 522, 146;* Rabies 807.23; Raynaud's Disease 727, 20; Rheumatoid arthritis of the muscles and tendons 251.2, 9.6, 9.4, 1875, 10,000, 2352, 880, 787, 727, 465, 20, 7.7, 3.0, 1.2; Rhinitis 10,000, 2352, 1500, 880, 787, 776, 727, 444, 7.83, 522, 146, 465; Sarcoma 2127, 2008, 880, 787, 727, 690, 666, 589; Scars 465 to 1568; Scarlet Fever 880, 787, 727, 1356; Sciatica or Ischia 2352, 880, 787, 727, 690, 666, 10; Sedative Effect 2.5; Sexual Dysfunction 9.4, 2127 2008, 465, 880, 802, 787, 2083, 125, 95, 73, 72, 20, 1875; Shingles 2352, 802, 1800, 1865, 1880, 787, 727, 26; Sinusitis 2352, 880, 787, 727, 125, 72, 522; Sleeping Sickness 124; Slipped discs 26, 125, 880, 787, 333, 787, 727, 95, 72, 522, 146, 555, 333, 999; Smallpox 811.91, 1550, 802, 880, 787, 727; Sneezing 880, 787, 727, 465, 146; Sore Throat 2720, 2489, 1800, 1600, 2352, 880, 787, 776, 727, 465, 589, 808.79; Spasms, muscle 6.8; Spastic paresis 650, 625, 30.87,48; Spleen, enlarged 35, 787, 10,000, 2720, 2170, 1800, 1550, 880, 802, 727, 465, 20; Spondylitis, acute 1.2, 10, 7.7, 28; Staphylococci infection 727; Stiff neck 4.9; Spastic stiff neck 9.2, 6.0; Stiff muscles in general 320, 250, 240, 160, 125, 80, 40, 20, 10, 5.8, 2.5, 1.5, 1.2, 1.0, 0.5, 1800, 2352, 880, 787, 776, 727; Stomach disorders 2127, 2008, 880, 787, 727, 2083, 125, 95, 72, 20, 3.9, 450, 1570, 1770; Stones 3.5; Streptococci infection 880; Streptothrix infection 787; Sty 10,000, 880, 787, 727, 20; Subluxation induced disorders 9.6; Sun Allergy 3.0, 330; Sunstroke 444, 428, 190, 3040, 95, 522, 146, 880, 20; Surgery-Prevention and control of nosocomial and idiopathic infection 2170, 1800 1600, 2352, 1500, 880, 832, 802, 787, 776, 727, 465, 444, 522, 146, 428, 589, 333, 3040, 95, 160, 26, 544; Swelling 522, 146, 6.3, 148, 444, 428, 880, 787, 727; Swollen glands 880, 787, 727, 2.0; Syphilis 1875; Tachycardia (also used for pain of arthritis, headache, Tui-na, and facial toning) 1.2; Teeth 3040, 95, 190, 47.5, 1600, 2352, 1500, 880, 10,000, 2489, 787, 776, 760, 727, 1875, 465, 2720, 2489, 1800; Tendo myopathy 3040, 320, 250, 160, 80, 40, 26, 20, 10, 5.8, 2.5, 1.5, 1.2, 1.0, 0.5; 522, 146; Tetanus 811.91, 600, 880, 787, 727; Thrush 465; Tonsillitis 74.2; 73, 2352, 1500, 880, 832, 787, 776, 727, 1875, 465, 808.79, 589; Toothache 3040, 95, 190, 47.5, 2720, 2489, 1800, 1600, 2352, 1500, 880, 832, 787, 776, 727, 666, 650, 600, 465, 522, 146, 555, 333, 999; Tooth extraction, afterward 3040, 95, 47.5, 7.83; Toxins 444, 160, 522, 146, 555, 333, 999, 10,000, 880, 787, 727, 125, 95, 72, 20; Trauma 3040, 95, 190, 760, 880, 787, 727, 465; Trench Mouth 1875, 880, 787, 776, 727, 650, 625, 465; Trigeminal neuralgia 2720, 2489, 2170, 1800, 1600, 2352, 880, 832, 787, 776, 760, 727, 650, 146, 7.83, 27.5, 428, 660, 589, 333, 999, 770, 2000, 805.6, 807.23, 811.91, 810.35; Tuberculosis 2352, 1875, 776, 2127, 2008, 465, 589; Typhoid 1570, 1770, 2352, 690, 1800; Ulcers 2489, 2170, 2127, 1800, 1600, 880, 832, 802, 787, 776, 727, 1.2 through 5.8, 1.2, 73; Urethritis 2720, 2170, 2127, 1800, 1600, 2352, 1500, 880, 832, 787, 776, 727, 1875, 455, 2309, 125, 95,.72, 1.2; Urticaria 1800, 444, 125, 95, 72, 522, 146, 787, 727, 6.3; Varicoses 1.2, 28; Vegetative Dystonia 40; Vein thrombosis 685; Vertigo 60, 5.8; Warts 3040, 5, 2720, 2127, 2008, 1800, 1600, 1500, 2083; Worms 125, 95, 6.0, 20, 2309; Wound healing 880, 787, 727, 220, 190, 20, 40; Yeast infection 465; Yellow Fever 999; Scan brain for troubled areas 7.83; For relaxation 4.9; To stimulate mental clarity 12; Facial toning 9.6; Kidney meridian 9.2.

21. The system as defined by claim 17 wherein the frequency responsive means further includes a gating means having ON/OFF functions, the ON function permitting the precise frequency signal to pass for a predetermined period of time and the OFF function gating the precise frequency output signal OFF for a determinable predetermined period of time.

22. The system as defined by claim 21 wherein the gating means gates the output signal OFF for a time period of around one second and gates such output signal ON for a user determinable period of around one to seven seconds.

23. The system as defined by claim 17 wherein the control means also stores a plurality of control signals, each control signal being operative to direct the signal generating means to generate a sequence of specific precise frequency output signals.

24. The system as defined by claim 23 wherein the system also includes audio means coupled to the output means and being operable upon termination of a first precise frequency signal and prior to commencement of a succeeding precise frequency output signal in a sequence to provide an auditory signal to a user of the system that a succeeding frequency signal is commencing.

25. The system as defined by claim 17 wherein the variable output means further includes circuitry which at the start of an output signal increases the amplitude of the output signal at a predetermined rate from zero to a determinable maximum value.

26. The system as defined by claim 25 wherein the control means is also variable by a user of the system to determine the level of the output signal.

27. The system as defined by claim 25 wherein the application means includes spaced electrode means which are intended to be placed in operative contact with a subject for direct application thereto of the output signal, and the system further includes visual display means which is operative to indicate to a user of the system whether the electrode means are in proper operative contact with the subject.

28. A method of inactivating micro-organisms and viruses which my be present in a mammal and enhancing tissue regeneration in a mammal, which method comprises:

generating a precise frequency electrical output signal that has a square wave shape and a 50% duty cycle, said frequency being selectable in a range from about 0.00004 Hz. to 3 Mhz. and having an output level for mammals does not exceed a value of about 50 volts, after the step of generating a precise frequent electrical output signal, the step of gating a precise frequency output signal selected for enhancing tissue enhancing regeneration ON and OFF repeatedly to provide an OFF interval having a time period of at least one second and a selectable ON interval of about one to seven seconds, and applying the output signal directly to a mammal in a manner to provide the most direct electrical signal through opposing surfaces of the area of the body of the mammal afflicted with such micro-organism or virus or requiring tissue regeneration for a predetermined period of time.

29. The method of claim 28 which further includes the step of, upon initiation of application of the output signal to a mammal, gradually increasing the amplitude level of the output signal from zero to a determinable maximum value at a gradual predetermined rate.

30. The method of claim 28 which further includes the steps of storing information representative of each of a plurality of specific precise frequencies and sequences of succeeding precise frequency output signals, selecting such information, and directing the generation of such precise frequencies in accordance with such information.

31. The method of claim 28 which further includes the step of testing the application of the output signal and providing a signal indicative of whether such output signal is being properly applied.

32. The method of claim 28 wherein said precise frequency of said generated signal is in cycles per second and is selected from the following group of frequencies for a specific health science purpose each frequency of said group being selected for inactivating micro-organisms and viruses which may be present at specific locations and enhancing tissue regeneration in a mammal, said group of frequencies and the purpose therefore consist of Adynamia, geriatric 60, 27.5; Abdominal inflammation 380, 1.2, 2727, 2489, 2170, 1800, 1600, 2302, 880, 832, 787, 776, 727, 465, 444, 1865, 146, 125, 95, 72, 20, 450, 440, 428, 660, 589, 2000, 1570, 1770, 805.6, 811.91; Abdominal pain 3.0, 440, 95, 160, 26, 522, 146, 555, 333, 999, 10000, 3040, 1865, 125, 95, 72; Abscesses 2720, 2170, 880, 787, 727, 190, 500; Acidosis 10000, 880, 802, 787, 776, 727, 20, 146; Ache 2720, 2170, 1800, 1600, 1500, 880, 787, 727; Actinomycosis 465, 10000, 787, 727, 20; Acupuncture disturbance field 18; Acute Pain 160, 26, 3040, 95, 522, 146, 555, 333, 999, 10000, 880, 787, 727, 690, 666; Adenoids 1550, 802, 880, 787, 776, 727, 444, 20, 428, 660, 589, 333, 14, 2000, 770, 780, 805.6, 808.79, 2720, 2170; Adhesions 2720, 2170, 1550, 802, 880, 787, 776, 760, 727, 190; Adrenal stimulant 20; Allergy 10000, 3.0 and 330, 522, 146, 555, 333, 999, 125, 95, 72, 20, 444, 1865; Alopecia 10000, 880, 787, 727, 465, 146; Amenorrhea 444, 522, 146, 555, 333, 999, 125, 95, 72, 880, 10000, 3040, 787, 760, 727, 20; Anal itching 465, 444, 125, 95, 72, 444, 186, 20, 2000, 522, 146, 555, 333, 999, 10000, 880, 787, 760, 727; Angina 787, 776, 727, 465, 428, 660, 589, 333, 14, 2000, 780, 1570, 1770, 805.6; Ankylosing spondylitis 3040, 95, 3352, 880, 787, 776, 727, 1875, 28, 1.2, 10, 35, 28, 7.7, 1.2, 110, 100, 60, 808.79, 428, 660, 333, 14, 2000; Antiseptic effect 2352, 880, 787, 760, 727, 465, 444, 450, 428, 660, 589, 555, 333, 14, 2000, 1570, 1770; Apoplexy 40, 20, 1800, 1875, 125, 95, 72, 20, 2309, 522, 146, 555, 333, 999, 880, 787, 727; Appetite, lack of 465, 2309, 125, 95, 72, 20, 10000, 880, 787, 727; Arteriosclerosis 10000, 2720, 2170, 1800, 1600, 1500, 880, 787, 776, 727, 20, 808.79; Arthritis, 10000, 1550, 880, 802, 787, 727, 28, 20, 7.7, 3.0, 1.2; Arthritis, rheumatoid of the muscles and tendons 250, 1.2, 1875, 787, 727, 808.79; Arthritis, arthrosis and parathyroid disturbances affecting calcium metabolism, 9.6; Arthritis, arthralgia due to gout, 9.4; Arthritis focal origin 9.4; Asthma, 2720, 2170, 1800, 1600, 1500, 880, 787, 727, 808.79; Astrocytoma 9.2, 8.25, 7.7, 2170, 2127, 880, 690, 666; Ataxia 2720, 2170, 1800, 1600, 1500, 880, 787, 776, 727, 650, 625, 600, 2309, 125, 95, 72, 20, 805.6, 811.91, spastic ataxia, 9.2, 8.25, 7.7; Athlete's Foot 465, 1550, 880, 802, 727, 20, Autoimmune Disorders 10000, 3352, 880, 787, 776, 727, 650, 625, 600, 465, 250, 28, 20, 9.6, 9.4, 7.7, 3.0, 522, 146, 1850; Autointoxication 0.5, 522, 146, 10000, 880, 787, 727, 20, 555, 333, 999; Back pain 26, 186, 3040, 522, 146, 555, 333, 999, 10000, 760, 2352, 880, 787, 727; Bad Breath 2352, 880, 787, 727, 20; Bedsores 880, 2352, 787, 727, 485 followed by 1.2 and 73; Biliousness 2352, 10000, 880, 832, 787, 727, 465; Bladder and prostate complaints 880, 2352, 787, 727, 465, 20, 9.4 Boils 880, 2352, 787, 727, 465, 660, 589, 333; Bone trauma 380, 2352, 10000, 880, 787, 727; Bone/ periodontal disease 47.5, 1800, 1600, 1875, 880, 787, 776, 727; Bone protuberance 1.2 and 250; Brachial Neuralgia 0.5; Breast 880, 2352, 787, 776, 3083; Bright's Syndrome 1500, 880, 787, 727; Bronchial asthma 0.5, 522, 146, 125, 95, 72, 966, 20; Bronchitis 880, 727, 9.4, 9.35; Bronchial Pneumonia 2352, 880, 787, 776, 727; Bubonic Plague 500, plus secondary infections: 880, 787, 727, 20; Burns 190, 10000, 880, 787, 727, 465, 200; Bursitis 880, 787, 727; Cancer 465, 2127, 880, 787, 3083, 589; Cardiac Edema 9.2; Carpal Tunnel Syndrome 1550 thru 465, 6.3, 148, 2.5, 727, 522, 146, 444; Cataract 10000, 880, 787, 727; Catarrh 1550, 802, 880, 787, 727, 444, 20; Cerebral Palsy 880, 787, 727, 522, 146; Chicken Pox 2352, 1800, 1600, 1500, 880, 787, 727, 20; Cholera 880, 802, 450, 880, 787, 727; Chronic Fatigue Syndrome 10000, 2720, 1800, 880, 802, 787, 776, 727, 465, 966, 330, 148, 125, 95, 73, 72, 35, 27.5, 20, 6.3, 4.9, 428, 660; Circulatory stasis 40; Circulation disturbance problems 40,9.4; Concentration 7.83; Cold in head, chest 10,000, 1550, 880, 802, 787, 776, 727, 444, 20; Colic 1550, 832, 802, 787, 727, 20; Colitis 1550, 880, 832, 802, 440; Constipation 1550, 880, 802, 787, 776, 727, 20; Convulsions 10,000, 880, 787, 727; Contusions 9.1, 110; Costalgia 160, 26, 3040, 880, 787, 727, 10,000, 2353; Cramps 10,000, 880, 787, 727, 26; Cystitis (of urinary bladder) 1550, 880, 802, 787, 727, 465, 20; Deafness 10,000, 1550, 880, 802, 787, 727, 20; Dental foci 3040, 95, 190, 47.5, 1600, 1550, 2353, 1500, 880, 832, 787, 776, 760, 727, 1316, 1916, 465, 2720, 2489, 1800, 522, 146, 555, 333, 999; Depression, anxiety, trembling, weakness 3.5; Depression 35, 220, 1.1, 73; Detoxification 6.3, 148, 2.5, 727, 522, 146, 444, 666, 428, 880, 787, 555, 333, 999; Diabetes 837, 260, 1885, 125, 95, 1957, 522, 428, 49.4 for secondary diabetes infections 10,000, 2720, 2170, 1800, 1550, 880, 802, 727, 465, 20; Diabetic loading 35, 700; Diarrhea/Dysentery 1550, 880, 802, 787, 727, 465; Distorsion 9.1, 110; Dizziness 5.8; Dupuytren's Contracture 1.2, 250; Dysmenorrhea 26, 4.9, 2352, 880, 787, 727, 465; Dyspepsia 1550, 880, 802, 787, 727; Ears 9.2, 880, 787, 727, 20; Eczema 9.2, 1550, 802, 787, 727; Eczema 9.4; Enuresis 10,000, 880, 787, 727, 465; Edema 522, 146, 154.3, 444, 440, 880, 787, 727, 465; Epicondylitis 251.2, 3040, 160, 26; Epididymitis 1500, 880, 787, 7827, 20; Epilepsy 10,000, 880, 802, 787, 727, 700, 650, 600, 125, 20; Epstein-Bart 428, 660, 776, 465, 880, 787, 727; Erysipelas 660, 2000, 10,000, 880, 787, 727, 465, 20; Erythema nosodum 9.4; Esophagus 880, 787, 727; Eustachian tube inflammation 1550, 880, 802, 787, 776, 727, 465; Eye inflammation 1.2, 80; Eye Disorders 1600, 10,000, 880, 787, 727, 20; Eyes 1600, 880, 787, 727; Facial paralysis 10,000, 880, 787, 727; Fatigue 2720, 1800, 428, 660, 465, 125, 95, 72, 27.5, 20, 2309; Fever 880, 787, 727, 20; Fibroma 2127, 2008, 727, 690, 666, 1550, 802, 465; Fibrosis of lung 457.5; Fistulal Ulcer 880, 832, 787, 727; Flashes, hot (complications) 10,000, 880, 787, 727; Flatulence 1550, 880, 802, 787, 760, 727, 465; Flu 1550, 880, 802, 787, 727, 20; Foot (blisters) 10,000, 880, 787, 727, 600; Fractures 450, 10,000, 880, 787, 727; Frostbite 880, 787, 727; Frozen shoulder 10,000, 880, 802, 787, 727; Fungal infection 465, 1550, 880, 802, 727, 20; Furunkulosis herpes, skin diseases 1200, 1550, 802, 2000, 787, 727; Gall bladder dystonia with osteitis 2.6, 3040, 880, 787, 727, 20; Gallstones 2.65, 3040, 880, 787, 727, 20; Gangrene 880, 787, 727, 20, 73; Gas (intestinal) 1550, 880, 802, 787, 760, 727, 465; Gastritis and flatus 880, 832, 787, 727, 20; Gout 9.4, 3040, 880, 787, 727, 20; Gravel in urine 2.6, 3040, 880, 787, 727, 20; Gums (inflammation, gingivitis, pyorrhea) 1550, 880, 802, 787, 727, 465, 20; Hair loss 10,000, 880, 787, 727, 465, 146; Hallucinations 10,000, 880, 787, 727, 20; Hangover 10,000, 146, 410; Hay Fever 880, 787, 727, 20; Headaches 160, 10, 6.3, 522, 146, 4.9, 3040, 727, 148, 125, 95, 72, 20, 10, 5.8, 2.5, 444, 685, 880, 787, 650, 625, 600, 3040, 428, 660, 555, 333, 999; For headaches caused by parasites 160, 125, 95, 73, 20, 727, 3040; Headaches (urogenitaiiy caused) 160, 9.4, 3040, 555, 333, 999, 160, 9.6, 3040; Head Injuries 160, 9.6, 3040, 880, 787, 727, 522, 72, 5.8, 4.9; Hearing problems 10,000, 2158, 880, 787, 760, 727, 20; Heart (lab animals only) 80, 160, 20, 73, 3.9, 10,000, 880, 787, 727, 465, 4125 95, 20; Heartburn 832, 2720, 2170, 2127, 1800, 1600, 2352, 1500, 880, 787, 727, 685, 465, 2309, 125, 95, 72, 20; Hemorrhage 1550, 802; Hemorrhoids 1550, 880, 802, 727; Hepatitis (generic) 29.2, 1550, 880, 802, 727; Hernia 10,000, 787, 727; Herpes (zoster) 2720, 2170, 1800, 1600, 1500, 1550, 802, 1865,880, 787, 727, 20; High blood pressure 10,000, 880, 787, 727, 9.2; Hip Pain (as in coxarthritis) 3040, 880, 787, 727, 160, 26; Hives 1800, 880, 787, 727, 522, 146, 4.9; Hoarseness 880, 760, 727; Hyperacidity of stomach 7.83 on solar plexus and 230 on stomach; Hydrocele 880, 787, 727; Hyperosmia 20, 10,000, 522, 1865, 810.35; Hyperthyroid 3.0, 0.5; Hypoacidity of stomach 15, 20; Hypothyroid 12, 35; Hypertension 20, 95, 9.2, 6.0, 10,000, 880, 787, 727; Hypertension, spastic 95; Impotence 9.4, 2127, 2008, 465, 880, 802, 787, 2083, 125, 95, 73, 72, 20, 1875; Indigestion 10,000, 880, 787, 727, 465, 444, 20, 125, 95, 72, 4.9; Infantile Paralysis 1500, 880, 787, 727; Infections 1600, 1550, 1500, 880, 832, 802, 787, 776, 760, 727, 700, 690, 666, 650, 625, 600, 465, 444, 125, 95, 72, 20, 1865, 500, 450, 440, 428, 660; Infertility 2127, 2008, 465, 880, 802, 787, 2083, 1875, 9.4; Inflammation 1.5; Influenza 1550, 802, 1500, 880, 787, 727, 20; Insomnia 3.6, 3.0, 1550, 1500, 880, 802; Intercostal neuralgia 3040, 160, 26, 1550, 880, 802, 787, 776, 727, 125, 20, 1865, 444; Intermittent claudication 45, 48; Itching 880, 787, 727, 465, 444, 125, 95, 72, 7.83, 2309, 2000; Jaundice 1600, 1550, 1500, 880, 802, 650, 625, 600, 2309, 146, 250, 125, 95, 72, 20; Kidney insufficiency 50, 440, 1600, 1550, 1500, 880, 802, 787, 727, 650, 625, 600, 465, 73, 40, 10, 2309, 522, 146, 250, 148, 125, 95, 72, 20, 555, 333, 999; Knee/Joint pain 3040, 160, 26, 1550, 880, 802, 787, 727, 28, 20, 7.7, 3.0, 1.2, 250, 1.2, 9.6, 9.4; Larynx 440, 465, 444, 1550, 880, 802, 787, 727, 28, 7.7, 3.0, 1.2, 250, 1.2, 9.6, 9.4; Leprosy 600, 1600, 1550, 1500, 880, 832, 802, 787, 776, 760, 727, 700, 690, 666, 650, 625, 600, 465, 444, 20, 500, 450, 440, 428, 660; Leukemia 2127, 2008, 880, 787, 727, 690, 666, 589; Leukoderma 880, 787, 727, 444, 20, 589, 2000; Locomotor Dysfunction 10,000, 880, 787, 776, 727, 650, 625, 600, 2309, 125, 95, 72, 20; convulsions, spasticity 28, 8.25, 7.7; Low Blood Pressure 880, 787, 727, 20; Lumbago 10,000, 880, 787, 727, 125, 95, 72, 2309, 9.2, 8.25, 7.7; Lungs 1550, 802, 880, 787, 776, 727, 125, 95, 72, 20, 2309, 450, 589; Lupus Erythematosus 880, 787, 727, 776, 1850; Luxation 119.1;. Lymph stasis 154.3, 2.5, 727, 522, 146, 444, 428, 880, 787; Malaria 555; Measles 333; Mental Disorders 444, 148, 20, 6.3, 2.5, 522, 146, 10,000, 125, 95, 72, 4.9, 727, 428, 444, 465 to 1550; Menieres Disease 2352, 880, 787, 727, 465, 428, 589, 333; Meningitis 2352, 880, 832, 787, 727, 650, 625, 600, 465, 2309, 125, 95, 72, 20, 428, 660; Menstrual problems 26, 3040, 880, 787, 727, 465, 160, 20; Migraine 170; Motion Sickness 650, 625, 600, 465, 444, 1865, 522, 146, 125, 95, 72, 20; Mouth eruptions 465, 2127, 2008, 727, 690, 666; Herpes sores 2489, 1800, 465, 1550, 1500, 880, 787, 727, 1850, 428; Mucous membrane inflammation 380; Multiple Sclerosis use auto immune frequencies plus 880, 787, 727; Muscles, to relax 760, 6.8; Muscular Dystrophy 10,000, 2352, 880, 787, 776, 727, 650, 625, 600, 465, 250, 28, 20, 9.6, 9.4, 7.7, 3.0, 522, 610, 1850, 146, 555, 333, 999; Muscular pain 3040, 26, 160, 320, 250, 240, 80, 40, 10, 5.8, 2.5, 1.5, 1.2, 1.0, 0.5; Muscle pain from parasites 2309, 125, 811, 108, 72, 20; Mumps 10,000, 727, 2720, 2489, 2127, 2008, 14, 428, 880, 787, 727, 20; Nausea 880, 832, 787, 727, 20, 4.9; Nephritis/nephrosis 880, 787, 727, 10, 40, 73, 465; Nervousness 3.0; Nerve disorders 10,000, 2720, 2489, 2170, 1800, 1600, 2352, 880, 787, 148, 6.3, 2.5, 522, 610, 727, 650, 625, 600, 125, 95, 72, 20, 428, 660, 333; Neuralgia 3.9, 555, 333, 999; Neurosis 28; Nose infection, congestion 2352, 880, 787, 776, 727, 444, 440, 465, 20; Numbness 10,000, 2720, 2489, 2170, 1800, 1600, 2352, 880, 787, 727, 650, 625, 600, 440, 660, 333; Oral Lesions 2720, 2489, 2008, 1800, 1600, 2352, 880, 787, 776, 760, 727, 465, 444, 522, 146, 555, 333, 999; Orchitis 2720, 2489, 2170, 2127, 2008, 1800, 1600, 2352, 1500, 880, 832, 787, 776, 2083, 650, 625, 600, 125, 95, 72, 20, 14; Osteomyelitis 2.6, 2720, 2489, 2170, 2127, 2008, 1800, 1600, 2352, 1500, 880, 832, 787, 776, 2083; Otosclerosis 9.2; Ovarian disorders 1875, 465, 444, 26, 2720, 2489, 2170, 2127, 2008, 1800, 1600, 2352, 1500, 880, 832, 787, 776, 2083, 20; Pain 3040, 95, 160, 26; Pain of infection 3040, 160, 26, 95, 880, 2352, 787, 776, 727, 4.9; Pain of cancer 3040, 160, 26, 95, 2127, 2008, 2083; Pancreatic insufficiency 15, 10, 250, 1875, 465, 444, 26, 2720, 2489, 2170, 2127, 2008, 1800, 1600, 2352, 1500, 880, 832, 787, 776, 2083, 20; Paralysis, spastic 10,000, 880, 787, 776, 727, 650, 625, 600, 2309, 125, 95, 72, 20, 7.7; Paralysis, nonspastic 10,000, 880, 787, 776, 727, 650, 625, 600, 444, 1865, 125, 95, 72, 20, 9.2, 8.25; Parasites 125, 95, 72, 20, 2309; Pelvic Inflammatory Disease 2720, 2489, 2170, 2127, 2008, 1800, 1600, 2352, 787, 776, 2083, 650, 625, 600, 465, 966, 95, 72, 450, 428, 14, 589, 1570; Pericarditis 2720, 2170, 1600, 880, 2352, 787, 760, 727, 625, 465, 160, 125, 73, 26, 20, 3.9, 95, 80, 73, 72, 2309; Pharyngitis 440, 589, 380, 1600, 2352, 776, 787, 880, 727, 20, 522, 146; Pleurisy 1550, 802, 880, 787, 776, 727, 125, 95, 72, 20, 2309, 450, 589; Pneumonia 1550, 802, 880, 787, 776, 727, 20, 450, 589; Poliomyelitis 805.6 secondary complications 2158, 428, 1500, 880, 787, 727; Polyps 2720, 2489, 2170, 2127, 2008, 1800, 1600, 2083, 1875, 465, 444, 20, 522, 146; Pre-op and post-operation prevention and control of nosocomial and idiopathic infection 2170, 1800, 1600, 2352, 1500, 880, 832, 802, 787, 776, 727, 465, 444, 522, 146, 428, 589, 333; Prostatitis 510, 522, 146, 2720, 2489, 2170, 2127, 2008, 2352, 787, 776, 2083, 465, 125, 95, 72, 20, 1249; Prostate complaints 9.4, 2127, 2008, 727, 690, 666, 465, 880, 802, 787, 727, 125, 95, 73, 72, 20; Proritis 880, 787, 727, 465, 444, 125, 95, 72, 20, 2309, 2000; Prostate tumor (malignant) 2127, 2008, 2083; Psychosomatic pain 727, 160, 26, 148, 455, 511, 146, 555, 333, 99.9; Pyorrhea 2720, 2489, 2008, 1800, 1600, 2352, 880, 787, 776, 727, 465, 444, 522, 146; Rabies 807.23; Raynaud's Disease 727, 20; Rheumatoid arthritis of the muscles and tendons 251.2, 9.6, 9.4, 1875, 10,000, 2352, 880, 787, 727, 465, 20, 7.7, 3.0, 1.2; Rhinitis 10,000, 2352, 1500, 880, 787, 776, 727, 444, 7.83, 522, 146, 465; Sarcoma 2127, 2008, 880, 787, 727, 690, 666, 589; Scars 465 to 1568; Scarlet Fever 880, 787, 727, 1356; Sciatica or Ischia 2352, 880, 787, 727, 690, 666, 10; Sedative Effect 2.5; sexual Dysfunction 9.4, 2127 2008, 465, 880, 802, 787, 2083, 125, 95, 73, 72, 20, 1875; Shingles 2352, 802, 1800, 1865, 1880, 787, 727, 26; Sinusitis 2352, 880, 787, 727, 125, 72, 522; Sleeping Sickness 124; Slipped discs 26, 125, 880, 787, 333, 787, 727, 95, 72, 522, 146, 555, 333, 999; Smallpox 811.91, 1550, 802, 880, 787, 727; Sneezing 880, 787, 727, 465, 146; Sore Throat 2720, 2489, 1800, 1600, 2352, 880, 787, 776, 727, 465, 589, 808.79; Spasms, muscle 6.8; Spastic paresis 650, 625, 30.87,48; Spleen, enlarged 35, 787, 10,000, 2720, 2170, 1800, 1550, 880, 802, 727, 465, 20; Spondylitis, acute 1.2, 10, 7.7, 28; Staphylococci infection 727; Stiff neck 4.9; Spastic stiff neck 9.2, 6.0; Stiff muscles in general 320, 250, 240, 160, 125, 80, 40, 20, 10, 5.8, 2.5, 1.5, 1.2, 1.0, 0.5, 1800, 2352, 880, 787, 776, 727; Stomach disorders 2127, 2008, 880, 787, 727, 2083, 125, 95, 72, 20, 3.9, 450, 1570, 1770; Stones 3.5; Streptococci infection 880; Streptothrix infection 787; Sty 10,000, 880, 787, 727, 20; Subluxation induced disorders 9.6; Sun Allergy 3.0, 330; Sunstroke 444, 428, 190, 3040, 95, 522, 146, 880, 20; Surgery-Prevention and control of nosocomial and idiopathic infection 2170, 1800 1600, 2352, 1500, 880, 832, 802, 787, 776, 727, 465, 444, 522, 146, 428, 589, 333, 3040, 95, 160, 26, 544; Swelling 522, 146, 6.3, 148, 444, 428, 880, 787, 727; Swollen glands 880, 787, 727, 20; Syphilis 1875; Tachycardia (also used for pain of arthritis, headache, Tui-na, and facial toning) 1.2; Teeth 3040, 95, 190, 47.5, 1600, 2352, 1500, 880, 10,000, 2489, 787, 776, 760, 727, 1875, 465, 2720, 2489, 1800; Tendo myopathy 3040, 320, 250, 160, 80, 40, 26, 20, 10, 5.8, 2.5, 1.5, 1.2, 1.0, 0.5, 522, 146; Tetanus 811.91, 600, 880, 787, 727; Thrush 465; Tonsillitis 74.2, 73, 2352, 1500, 880, 832, 787, 776, 727, 1875, 465, 808.79, 589; Toothache 3040, 95, 190, 47.5, 2720, 2489, 1800, 1600, 2352, 1500, 880, 832, 787, 776, 727, 666, 650, 600, 465, 522, 146, 555, 333, 999; Tooth extraction, afterward 3040, 95, 47.5, 7.83; Toxins 444, 160, 522, 146, 555, 333, 999, 10,000, 880, 787, 727, 125, 95, 72, 20; Trauma 3040, 95, 190, 760, 880, 787, 727, 465; Trench Mouth 1875, 880, 787, 776, 727, 650, 625, 465; Trigeminal neuralgia 2720, 2489, 2170, 1800, 1600, 2352, 880, 832, 787, 776, 760, 727, 650, 146, 7.83, 27.5, 428, 660, 589, 333, 999, 770, 2000, 805.6, 807.23, 811.91, 810.35; Tuberculosis 2352, 1875, 776, 2127, 2008, 465, 589; Typhoid 1570, 1770, 2352, 690, 1800; ulcers 2489, 2170, 2127, 1800, 1600, 880, 832, 802, 787, 776, 727, 1.2 through 5.8, 1.2, 73; Urethritis 2720, 2170, 2127, 1800, 1600, 2352, 1500, 880, 832, 787, 776, 727, 1875, 455, 2309, 125, 95, 72, 1.2; Urticaria 1800, 444, 125, 95, 72, 522, 146, 787, 727, 6.3; Varicoses 1.2, 28; Vegetative Dystonia 40; Vein thrombosis 685; Vertigo 60, 5.8; Warts 3040, 5, 2170, 2127, 2008, 1800, 1600, 1500, 2083; Worms 125, 95, 6.0, 20, 2309; Wound healing 880, 787, 727, 220, 190, 20, 40; Yeast infection 465; Yellow Fever 999; Scan brain for troubled areas 7.83; For relaxation 4.9; To stimulate mental clarity 12; Facial toning 9.6; Kidney meridian 9.2.

33. The method of claim 28 wherein the generating step further includes generating a first precise frequency output signal for a predetermined period of time and subsequently generating a plurality of succeeding precise frequency output signals for predetermined time periods.

34. The method of claim 33 wherein the frequency of each such succeeding precise frequency output signal differs from the frequency of the present frequency signal by one Hz.

35. The method of claim 28 wherein the generating step further includes generating a first precise frequency output signal for a predetermined period of time and, upon completion of such time period, immediately generating at least one other precise frequency output signal for a predetermined time period.

36. The method of claim 35 which further includes the step of providing an audible signal upon initiation of each successive precise frequency output signal of a sequence of such signals.

37. The method of claim 35 which further includes the step of providing a visual display of information representative of a particular frequency or sequence of frequencies being presently generated and the time period remaining for that frequency to continue to be generated.

38. A system to generate an output signal having a predetermined precise frequency and particularly adapted for use in applications including health science and industrial by a user, comprising:

means responsive to a control signal to generate an output signal having a precise frequency;

control means coupled to the precise frequency generating means and operative to generate a determinable control signal selected by a user;

means responsive to the specific frequency signal generated to determine whether to selectively pulse the generated frequency signal ON and OFF in a predetermined sequence;

variable output means coupled to the precise frequency signal generating means to amplify the voltage of the generated signal to a determinable predetermined level, and application means coupled to the output means for application of the amplified output signal for uses including health science by a user, said precise frequency of said generated signal is in cycles per second and is selected from the following group of frequencies for a specific health science purpose each frequency of said group being selected for inactivating micro-organisms and viruses which may be present at specific locations and enhancing tissue regeneration in a mammal, said group of frequencies and the purpose therefore consist of Adynamia, geriatric 60, 27.5; Abdominal inflammation 380, 1.2, 2727, 2489, 2170, 1800, 1600, 2302, 880, 832, 787, 776, 727, 465, 444, 1865, 146, 125, 95, 72, 20, 450, 440, 428, 660, 589, 2000, 1570, 1770, 805.6, 811.91; Abdominal pain 3.0, 440, 95, 160, 26, 522, 146, 555, 333, 999, 10000, 3040, 1865, 125, 95, 72; Abscesses 2720, 2170, 880, 787, 727, 190, 500; Acidosis 10000, 880, 802, 787, 776, 727, 20, 146; Acne 2720, 2170, 1800, 1600, 1500, 880, 787, 727; Actinomycosis 465, 10000, 787, 727, 20; Acupuncture disturbance field 18; Acute Pain 160, 26, 3040, 95, 522, 146, 555, 333, 999, 10000, 880, 787, 727, 690, 666; Adenoids 1550, 802, 880, 787, 776, 727, 444, 20, 428, 660, 589, 333, 14, 2000, 770, 780, 805.6, 808.79, 2720, 2170; Adhesions 2720, 2170, 1550, 802, 880, 787, 776, 760, 727, 190; Adrenal stimulant 20; Allergy 10000, 3.0 and 330, 522, 146, 555, 333, 999, 125, 95, 72, 20, 444, 1865; Alopecia 10000, 880, 787, 727, 465, 146; Amenorrhea 444, 522, 146, 555, 333, 999, 125, 95, 72, 880, 10000, 3040, 787, 760, 727, 20; Anal itching 465, 444, 125, 95, 72, 444, 186, 20, 2000, 522, 146, 555, 333, 999, 10000, 880, 787, 760, 727; Angina 787, 776, 727, 465, 428, 660, 589, 333, 14, 2000, 780, 1570, 1770, 805.6; Ankylosing spondylitis 3040, 95, 3352, 880, 787, 776, 727, 1875, 28, 1.2, 10, 35, 28, 7.7, 1.2, 110, 100, 60, 808.79, 428, 660, 333, 14, 2000; Antiseptic effect 2352, 880, 787, 760, 727, 465, 444, 450, 428, 660, 589, 555, 333, 14, 2000, 1570, 1770; Apoplexy 40, 20, 1800, 1875, 125, 95, 72, 20, 2309, 522, 146, 555, 333, 999, 880, 787, 727; Appetite, lack of 465, 2309, 125, 95, 72, 20, 10000, 880, 787, 727; Arteriosclerosis 10000, 2720, 2170, 1800, 1600, 1500, 880, 787, 776, 727, 20, 808.79; Arthritis, 10000, 1550, 880, 802, 787, 727, 28, 20, 7.7, 3.0, 1.2; Arthritis, rheumatoid of the muscles and tendons 250, 1.2, 1875, 787, 727, 808.79; Arthritis, arthrosis and parathyroid disturbances affecting calcium metabolism, 9.6; Arthritis, arthralgia due to gout, 9.4; Arthritis focal origin 9.4; Asthma, 2720, 2170, 1800, 1600, 1500, 880, 787, 727, 808.79; Astrocytoma 9.2, 8.25, 7.7, 2170, 2127, 880, 690, 666; Ataxia 2720, 2170, 1800, 1600, 1500, 880, 787, 776, 727, 650, 625, 600, 2309, 125, 95, 72, 20, 805.6, 811.91, spastic ataxia, 9.2, 8.25, 7.7; Athlete's Foot 465, 1550, 880, 802, 727, 20, Autoimmune Disorders 10000, 3352, 880, 787, 776, 727, 650, 625, 600, 465, 250, 28, 20, 9.6, 9.4, 7.7, 3.0, 522, 146, 1850; Autointoxication 0.5, 522, 146, 10000, 880, 787, 727, 20, 555, 333, 999; Back pain 26, 186, 3040, 522, 146, 555, 333, 999, 10000, 760, 2352, 880, 787, 727; Bad Breath 2352, 880, 787, 727, 20; Bedsores 880, 2352, 787, 727, 485 followed by 1.2 and 73; Biliousness 2352, 10000, 880, 832, 787, 727, 465; Bladder and prostate complaints 880, 2352, 787, 727, 465, 20, 9.4 Boils 880, 2352, 787, 727, 465, 660, 589, 333; Bone trauma 380, 2352, 10000, 880, 787, 727; Bone/ periodontal disease 47.5, 1800, 1600, 1875, 880, 787, 776, 727; Bone protuberance 1.2 and 250; Brachial Neuralgia 0.5; Breast 880, 2352, 787, 776, 3083; Bright's Syndrome 1500, 880, 787, 727; Bronchial asthma 0.5, 522, 146, 125, 95, 72, 966, 20; Bronchitis 880, 727, 9.4, 9.35; Bronchial Pneumonia 2352, 880, 787, 776, 727; Bubonic Plague 500, plus secondary infections: 880, 787, 727, 20; Burns 190, 10000, 880, 787, 727, 465, 200; Bursitis 880, 787, 727; Cancer 465, 2127, 880, 787, 3083, 589; Cardiac Edema 9.2; Carpal Tunnel Syndrome 1550 thru 465, 6.3, 148, 2.5, 727, 522, 146, 444; Cataract 10000, 880, 787, 727; Catarrh 1550, 802, 880, 787, 727, 444, 20; Cerebral Palsy 880, 787, 727, 522, 146; Chicken Pox 2352, 1800, 1600, 1500, 880, 787, 727, 20; Cholera 880, 802, 450, 880, 787, 727; Chronic Fatigue Syndrome 10000, 2720, 1800, 880, 802, 787, 776, 727, 465, 966, 330, 148, 125, 95, 73, 72, 35, 27.5, 20, 6.3, 4.9, 428, 6607 Circulatory stasis 407 Circulation disturbance problems 40,9.4; Concentration 7.83; Cold in head, chest 10,000, 1550, 880, 802, 787, 776, 727, 444, 20; Colic 1550, 832, 802, 787, 727, 20; Colitis 1550, 880, 832, 802, 440; Constipation 1550, 880, 802, 787, 776, 727, 20; Convulsions 10,000, 880, 787, 727; Contusions 9.1; 110; Costalgia 160, 26, 3040, 880, 787, 727, 10,000, 2353; Cramps 10,000, 880, 787, 727, 26; Cystiris (of urinary bladder) 1550, 880, 802, 787, 727, 465, 20; Deafness 10,000, 1550, 880, 802, 787, 727, 20; Dental foci 3040, 95, 190, 47.5, 1600, 1550, 2353, 1500, 880, 832, 787, 776, 760, 727, 1316, 1916, 465, 2720, 2489, 1800, 522, 146, 555, 333, 999; Depression, anxiety, trembling, weakness 3.5; Depression 35, 220, 1.1, 73; Detoxification 6.3, 148, 2.5, 727, 522, 146, 444, 666, 428, 880, 787, 555, 333, 999; Diabetes 837, 260, 1885, 125, 95, 1957, 522, 428, 49.4 for secondary diabetes infections 10,000, 2720, 2170, 1800, 1550, 880, 802, 727, 465, 20; Diabetic loading 35, 700; Diarrhea/Dysentery 1550, 880, 802, 787, 727, 465; Distortion 9.1, 110; Dizziness 5.8; Dupuytren's Contracture 1.2, 250; Dysmenorrhea 26, 4.9, 2352, 880, 787, 727, 465; Dyspepsia 1550, 880, 802, 787, 727; Ears 9.2, 880, 787, 727, 20; Eczema 9.2, 1550, 802, 787, 727; Eczema 9.4; 20; Enuresis 10,000, 880, 787, 727, 465; Edema 522, 146, 154.3, 444, 440, 880, 787, 727, 465; Epicondylitis 251.2, 3040, 160, 26; Epididymitis 1500, 880, 787, 7827, 20; Epilepsy 10,000, 880, 802, 787, 727, 700, 650, 600, 125, 20; Epstein-Bart 428, 660, 776, 465, 880, 787, 727; Erysipelas 660, 2000, 10,000, 880, 787, 727, 465, 20; Erythema nosodum 9.4; Esophagus 880, 787, 727; Eustachian tube inflammation 1550, 880, 802, 787, 776, 727, 465; Eye inflammation 1.2, 80; Eye Disorders 1600, 10,000, 880, 787, 727, 20; Eyes 1600, 880, 787, 727; Facial paralysis 10,000, 880, 787, 727; Fatigue 2720, 1800, 428, 660, 465, 125, 95, 72, 27.5, 20, 2309; Fever 880, 787, 727, 20; Fibroma 2127, 2008, 727, 690, 666, 1550, 802, 465; Fibrosis of lung 457.5; Fistulal Ulcer 880, 832, 787, 727; Flashes, hot (complications) 10,000, 880, 787, 727; Flatulence 1550, 880, 802, 787, 760, 727, 465; Flu 1550, 880, 802, 787, 727, 20; Foot (blisters) 10,000, 880, 787, 727, 600; Fractures 450, 10,000, 880, 787, 727; Frostbite 880, 787, 727; Frozen shoulder 10,000, 880, 802, 787, 727; Fungal infection 465, 1550, 880, 802, 727, 20; Furunkulosis herpes, skin diseases 1200, 1550, 802, 2000, 787, 727; Gall bladder dystonia with osteitis 2.6, 3040, 880, 787, 727, 20; Gallstones 2.65, 3040, 880, 787, 727, 20; Gangrene 880, 787, 727, 20, 73; Gas (intestinal) 1550, 880, 802, 787, 760, 727, 465; Gastritis and flatus 880, 832, 787, 727, 20; Gout 9.4, 3040, 880, 787, 727, 20; Gravel in urine 2.6, 3040, 880, 787, 727, 20; Gums (inflammation, gingivitis, pyorrhea) 1550, 880, 802, 787, 727, 465, 20; Hair loss 10,000, 880, 787, 727, 465, 146; Hallucinations 10,000, 880, 787, 727, 20; Hangover 10,000, 146, 610; Hay Fever 880, 787, 727, 20; Headaches 160, 10, 6.3, 522, 146, 4.9, 3040, 727, 148, 125, 95, 72, 20, 10, 5.8, 2.5, 444, 685, 880, 787, 650, 625, 600, 3040, 428, 660, 555, 333, 999; For headaches caused by parasites 160, 125, 95, 73, 20, 727, 3040; Headaches (urogenitaiiy caused) 160, 9.4, 3040, 555, 333, 999, 160, 9.6, 3040; Head Injuries 160, 9.6, 3040, 880, 787, 727, 522, 72, 5.8, 4.9; Hearing problems 10,000, 2158, 880, 787, 760, 727, 20; Heart (lab animals only) 80, 160, 20, 73, 3.9, 10,000, 880, 787, 727, 465, 4125 95, 20; Heartburn 832, 2720, 2170, 2127, 1800, 1600, 2352, 1500, 880, 787, 727, 685, 465, 2309, 125, 95, 72, 20; Hemorrhage 1550, 802; Hemorrhoids 1550, 880, 802, 727; Hepatitis (generic)29.2, 1550, 880, 802, 727; Hernia 10,000, 787, 727; Herpes (zoster) 2720, 2170, 1800, 1600, 1500, 1550, 802, 1865, 880, 787, 727, 20; High blood pressure 10,000, 880, 787, 727, 9.2; Hip Pain (as in coxarthritis) 3040, 880, 787, 727, 160, 26; Hives 1800, 880, 787, 727, 522, 146, 4.9; Hoarseness 880, 760, 727; Hyperacidity of stomach 7.83 on solar plexus and 230 on stomach; Hydrocele 880, 787, 727; Hyperosmia 20, 10,000, 522, 1865, 810.35; Hyperthyroid 3.0, 0.5; Hypoacidity of stomach 15, 20; Hypothyroid 12, 35; Hypertension 20, 95, 9.2, 6.0, 10,000, 880, 787, 727; Hypertension, spastic 95; Impotence 9.4, 2127, 2008, 465, 880, 802, 787, 2083, 125, 95, 73, 72, 20, 1875; Indigestion 10,000, 880, 787, 727, 465, 444, 20, 125, 95, 72, 4.9; Infantile Paralysis 1500, 880, 787, 727; Infections 1600, 1550, 1500, 880, 832, 802, 787, 776, 760, 727, 700, 690, 666, 650, 625, 600, 465, 444, 125, 95, 72, 20, 1865, 500, 450, 440, 428, 660; Infertility 2127, 2008, 465, 880, 802, 787, 2083, 1875, 9.4; Inflammation 1.5; Influenza 1550, 802, 1500, 880, 787, 727, 20; Insomnia 3.6, 3.0, 1550, 1500, 880, 802; Intercostal neuralgia 3040, 160, 26, 1550, 880, 802, 787, 776, 727, 125, 20, 1865, 444; Intermittent claudication 45, 48; Itching 880, 787, 727, 465, 444, 125, 95, 72, 7.83, 2309, 2000; Jaundice 1600, 1550, 1500, 880, 802, 650, 625, 600, 2309, 146, 250, 125, 95, 72, 20; Kidney insufficiency 50, 440, 1600, 1550, 1500, 880, 802, 787, 727, 650, 625, 600, 465, 73, 40, 10, 2309, 522, 146, 250, 148, 125, 95, 72, 20, 555, 333, 999; Knee/Joint pain 3040, 160, 26, 1550, 880, 802, 787, 727, 28, 20, 7.7, 3.0, 1.2, 250, 1.2, 9.6, 9.4; Larynx 440, 465, 444, 1550, 880, 802, 787, 727, 28, 7.7, 3.0, 1.2, 250, 1.2, 9.6, 9.4; Leprosy 600, 1600, 1550, 1500, 880, 832, 802, 787, 776, 760, 727, 700, 690, 666, 650, 625, 600, 465, 444, 20, 500, 450, 440, 428, 660; Leukemia 2127, 2008, 880, 787, 727, 690, 666, 589; Leukoderma 880, 787, 727, 444, 20, 589, 2000; Locomotor Dysfunction 10,000, 880, 787, 776, 727, 650, 625, 600, 2309, 125, 95, 72, 20; convulsions, spasticity 28, 8.25, 7.7; Low Blood Pressure 880, 787, 727, 20; Lumbago 10,000, 880, 787, 727, 125, 95, 72, 2309, 9.2, 8.25, 7.7; Lungs 1550, 802, 880, 787, 776, 727, 125, 95, 72, 20, 2309, 450, 589; Lupus Erythematosus 880, 787, 727, 776, 1850; Luxation 119.1; Lymph stasis 154.3, 2.5, 727, 522, 146, 444, 428, 880, 787; Malaria 555; Measles 333; Mental Disorders 444, 148, 20, 6.3, 2.5, 522, 146, 10,000, 125, 95, 72, 4.9, 727, 428, 444, 465 to 1550; Menieres Disease 2352, 880, 787, 727, 465, 428, 589, 333; Meningitis 2352, 880, 832, 787, 727, 650, 625, 600, 465, 2309, 125, 95, 72, 20, 428, 660; Menstrual problems 26, 3040, 880, 787, 727, 465, 160, 20; Migraine 170; Motion Sickness 650, 625, 600, 465, 444, 1865, 522, 146, 125, 95, 72, 20; Mouth eruptions 465, 2127, 2008, 727, 690, 666; Herpes sores 2489, 1800, 465, 1550, 1500, 880, 787, 727, 1850, 428; Mucous membrane inflammation 380; Multiple Sclerosis use auto immune frequencies plus 880, 787, 727; Muscles, to relax 760, 6.8; Muscular Dystrophy 10,000, 2352, 880, 787, 776, 727, 650, 625, 600, 465, 250, 28, 20, 9.6, 9.4, 7.7, 3.0, 522, 610, 1850, 146, 555, 333, 999; Muscular pain 3040, 26, 160, 320, 250, 240, 80, 40, 10, 5.8, 2.5, 1.5, 1.2, 1.0, 0.5; Muscle pain from parasites 2309, 125, 811, 108, 72, 20; Mumps 10,000, 727, 2720, 2489, 2127, 2008, 14, 428, 880, 787, 727, 20; Nausea 880, 832, 787, 727, 20, 4.9; Nephritis\nephrosis 880, 787, 727, 10, 40, 73, 465; Nervousness 3.0; Nerve disorders 10,000, 2720, 2489, 2170, 1890, 1600, 2352, 880, 787, 148, 6.3, 2.5, 522, 610, 727, 650, 625, 600, 125, 95, 72, 20, 428, 660, 333; Neuralgia 3.9, 555, 333, 999; Neurosis 28; Nose infection, congestion 2352, 880, 787, 776, 727, 444, 440, 465, 20; Numbness 10,000, 2720, 2489, 2170, 1800, 1600, 2352, 880, 787, 727, 650, 625, 600, 440, 660, 333; Oral Lesions 2720, 2489, 2008, 1800, 1600, 2352, 880, 787, 776, 760, 727, 465, 444, 522, 146, 555, 333, 999; Orchitis 2720, 2489, 2170, 2127, 2008, 1800, 1600, 2352, 1500, 880, 832, 787, 776, 2083, 650, 625, 600, 125, 95, 72, 20, 14; Osteomyelitis 2.6, 2720, 2489, 2170, 2127, 2008, 1800, 1600, 2352, 1500, 880, 832, 787, 776, 2083; Otosclerosis 9.2; Ovarian disorders 1875, 465, 444, 26, 2720, 2489, 2170, 2127, 2008, 1800, 1600, 2352, 1500, 880, 832, 787, 776, 2083, 20; Pain 3040, 95, 160, 26; Pain of infection 3040, 160, 26, 95, 880, 2352, 787, 776, 727, 4.9; Pain of cancer 3040, 160, 26, 95, 2127, 2008, 2083; Pancreatic insufficiency 15, 10, 250, 1875, 465, 444, 26, 2720, 2489, 2170, 2127, 2008, 1800, 1600, 2352, 1500, 880, 832, 787, 776, 2083, 20; Paralysis, spastic 10,000, 880, 787, 776, 727, 650, 625, 600, 2309, 125, 95, 72, 20, 7.7; Paralysis, nonspastic 10,000, 880, 787, 776, 727, 650, 625, 600, 444, 1865, 125, 95, 72, 20, 9.2, 8.25; Parasites 125, 95, 72, 20, 2309; Pelvic Inflammatory Disease 2720, 2489, 2170, 2127, 2008, 1800, 1600, 2352, 787, 776, 2083, 650, 625, 600, 465, 966, 95, 72, 450, 428, 14, 589, 1570; Pericarditis 2720, 2170, 1600, 880, 2352, 787, 760, 727, 625, 465, 160, 125, 73, 26, 20, 3.9, 95, 80, 73, 72, 2309; Pharyngitis 440, 589, 380, 1600, 2352, 776, 787, 880, 727, 20, 522, 146; Pleurisy 1550, 802, 880, 787, 776, 727, 125, 95, 72, 20, 2309, 450, 589; Pneumonia 1550, 802, 880, 787, 776, 727, 20, 450, 589; Poliomyelitis 805.6 secondary complications 2158, 428, 1500, 880, 787, 727; Polyps 2720, 2489, 2170, 2127, 2008, 1800, 1600, 2083, 1875, 465, 444, 20, 522, 146; Pre-op and post-operation prevention and control of nosocomial and idiopathic infection 2170, 1800, 1600, 2352, 1500, 880, 832, 802, 787, 776, 727, 465, 444, 522, 146, 428, 589, 333; Prostatitis 510, 522, 146, 2720, 2489, 2170, 2127, 2008, 2352, 787, 776, 2083, 465, 125, 95, 72, 20, 1249; Prostate complaints 9.4, 2127, 2008, 727, 690, 666, 465, 880, 802, 787, 727, 125, 95, 73, 72, 20; Proritis 880, 787, 727, 465, 444, 125, 95, 72, 20, 2309, 2000; Prostate tumor (malignant) 2127, 2008, 2083; Psychosomatic pain 727, 160, 26, 148, 455, 511, 146, 555, 333, 999; Pyorrhea 2720, 2489, 2008, 1800, 1600, 2352, 880, 787, 776, 727, 465, 444, 522, 146; Rabies 807.23; Raynaud's Disease 727, 20; Rheumatoid arthritis of the muscles and tendons 251.2, 9.6, 9.4, 1875, 10.000, 2352, 880, 787, 727, 465, 20, 7.7, 3.0, 1.2; Rhinitis 10,000, 2352, 1500, 880, 787, 776, 727, 444, 7.83, 522, 146, 465; Sarcoma 2127, 2008, 880, 787, 727, 690, 666, 589; Scars 465 to 1568; Scarlet Fever 880, 787, 727, 1356; Sciatica or Ischia 2352, 880, 787, 727, 690, 666, 10; Sedative Effect 2.5; Sexual Dysfunction 9.4, 2127 2008, 465, 880, 802, 787, 2083, 125, 95, 73, 72, 20, 1875; Shingles 2352, 802, 1800, 1865, 1880, 787, 727, 26; Sinusitis 2352, 880, 787, 727, 125, 72, 522; Sleeping Sickness 124; Slipped discs 26, 125, 880, 787, 333, 787, 727, 95, 72, 522, 146, 555, 333, 999; Smallpox 811.91, 1550, 802, 880, 787, 727; Sneezing 880, 787, 727, 465, 146; Sore Throat 2720, 2489, 1800, 1600, 2352, 880, 787, 776, 727, 465, 589, 808.79; Spasms, muscle 6.8; Spastic paresis 650, 625, 30.87.48; Spleen, enlarged 35, 787, 10,000, 2720, 2170, 1800, 1550, 880, 802, 727, 465, 20; Spondylitis, acute 1.2, 10, 7.7, 28; Staphylococci infection 727; Stiff neck 4.9; Spastic stiff neck 9.2, 6.0; Stiff muscles in general 320, 250, 240, 160, 125, 80, 40, 20, 10, 5.8, 2.5, 1.5, 1.2, 1.0, 0.5, 1800, 2352, 880, 787, 776, 727; Stomach disorders 2127, 2008, 880, 787, 727, 2083, 125, 95, 72, 20, 3.9, 450, 1570, 1770; Stones 3.5; Streptococci infection 880; Streptothrix infection 787; Sty 10,000, 880, 787, 727, 20; Subluxation induced disorders 9.6; Sun Allergy 3.0, 330; Sunstroke 444, 428, 190, 3040, 95, 522, 146, 880, 20; Surgery-Prevention and control of nosocomial and idiopathic infection 2170, 1800 1600, 2352, 1500, 880, 832, 802, 787, 776, 727, 465, 444, 522, 146, 428, 589, 333, 3040, 95, 160, 26, 544; Swelling 522, 146, 6.3, 148, 444, 428, 880, 787, 727; Swollen glands 880, 787, 727, 20; Syphilis 1875; Tachycardia (also used for pain of arthritis, headache, Tui-na, and facial toning) 1.2; Teeth 3040, 95, 190, 47.5, 1600, 2352, 1500, 880, 10,000, 2489, 787, 776, 760, 727, 1875, 465, 2720, 2489, 1800; Tendo myopathy 3040, 320, 250, 160, 80, 40, 26, 20, 10, 5.8, 2.5, 1.5, 1.2, 1.0, 0.5, 522, 146; Tetanus 811.91, 600, 880, 787, 727; Thrush 465; Tonsillitis 74.2, 73, 2352, 1500, 880, 832, 787, 776, 727, 1875, 465, 808.79, 589; Toothache 3040, 95, 190, 47.5, 2720, 2489, 1800, 1600, 2352, 1500, 880, 832, 787, 776, 727, 666, 650, 600, 465, 522, 146, 555, 333, 999; Tooth extraction, afterward 3040, 95, 47.5, 7.83; Toxins 444, 160, 522, 146, 555, 333, 999, 10,000, 880, 787, 727, 125, 95, 72, 20; Trauma 3040, 95, 190, 760, 880, 787, 727, 465; Trench Mouth 1875, 880, 787, 776, 727, 650, 625, 465; Trigeminal neuralgia 2720, 2489, 2170, 1800, 1600, 2352, 880, 832, 787, 776, 760, 727, 650, 146, 7.83, 27.5, 428, 660, 589, 333, 999, 770, 2000, 805.6, 807.23, 811.91, 810.35; Tuberculosis 2352, 1875, 776, 2127, 2008, 465, 589; Typhoid 1570, 1770, 2352, 690, 1800; Ulcers 2489, 2170, 2127, 1800, 1600, 880, 832, 802, 787, 776, 727, 1.2 through 5.8, 1.2, 73; Urethritis 2720, 2170, 2127, 1800, 1600, 2352, 1500, 880, 832, 787, 776, 727, 1875, 455, 2309, 125, 95, 72, 1.2; Urticaria 1800, 444, 125, 95, 72, 522, 146, 787, 727, 6.3; Varicoses 1.2, 28; Vegetative Dystonia 40; Vein thrombosis 685; Vertigo 60, 5.8; Warts 3040, 5, 2170, 2127, 2008, 1800, 1600, 1500, 2083; Worms 125, 95, 6.0, 20, 2309; Wound healing 880, 787, 727, 220, 190, 20, 40; Yeast infection 465; Yellow Fever 999; Scan brain for troubled areas 7.83; For relaxation 4.9; To stimulate mental clarity 12; Facial toning 9.6; Kidney meridian 9.2.

39. A system to generate an output signal having a predetermined precise frequency and particularly adapted for use in applications for health science, comprising:

frequency generation means for generating an output signal having a predetermined precise frequency within a frequency range from at least 0.00004 Hz to 3 Mhz;

means coupled to the frequency generation means and responsive to the specific precise frequency being generated to permit selective control of the generated frequency signal;

output means coupled to the frequency generation means to amplify the voltage of the generated frequency signal to a predetermined level, and application means coupled to the output means for application of the output signal for applications for health science wherein the frequency of said generated signal comprises selected frequency in cycles per second from a group of specific frequencies for inactivating microorganisms and viruses which may be present and enhancing specific tissue regeneration in a mammal, said group of frequencies and the purpose therefore consisting of Adynamia, geriatric 60, 27.5; Abdominal inflammation 380, 1.2, 2727,. 2489, 2170, 1800, 1600, 2302, 880, 832, 787, 776, 727, 465, 444, 1865, 146, 125, 95, 72, 20, 450, 440, 428, 660, 589, 2000, 1570, 1770, 805.6, 811.91; Abdominal pain 3.0, 440, 95, 160, 26, 522, 146, 555, 333, 999, 10000, 3040, 1865, 125, 95, 72; Abscesses 2720, 2170, 880, 787, 727, 190, 500; Acidosis 10000, 880, 802, 787, 776, 727, 20, 146; Ache 2720, 2170, 1800, 1600, 1500, 880, 787, 727; Actinomycosis 465, 10000, 787, 727, 20; Acupuncture disturbance field 18; Acute Pain 160, 26, 3040, 95, 522, 146, 555, 333, 999, 10000, 880, 787, 727, 690, 666; Adenoids 1550, 802, 880, 787, 776, 727, 444, 20, 428, 660, 589, 333, 14, 2000, 770, 780, 805.6, 808.79, 2720, 2170; Adhesions 2720, 2170, 1550, 802, 880, 787, 776, 760, 727, 190; Adrenal stimulant 20; Allergy 10000, 3.0 and 330, 522, 146, 555, 333, 999, 125, 95, 72, 20, 444, 1865; Alopecia 10000, 880, 787, 727, 465, 146; Amenorrhea 444, 522, 146, 555, 333, 999, 125, 95, 72, 880, 10000, 3040, 787, 760, 727, 20; Anal itching 465, 444, 125, 95, 72, 444, 186, 20, 2000, 522, 146, 555, 333, 999, 10000, 880, 787, 760, 727; Angina 787, 776, 727, 465, 428, 660, 589, 333, 14, 2000, 780, 1570, 1770, 805.6; Ankylosing spondylitis 3040, 95, 3352, 880, 787, 776, 727, 1875, 28, 1.2, 10, 35, 28, 7.7, 1.2, 110, 100, 60, 808.79, 428, 660, 333, 14, 2000; Antiseptic effect 2352, 880, 787, 760, 727, 465, 444, 450, 428, 660, 589, 555, 333, 14, 2000, 1570, 1770; Apoplexy 40, 20, 1800, 1875, 125, 95, 72, 20, 2309, 522, 146, 555, 333, 999, 880, 787, 727 Appetite, lack of 465, 2309, 125, 95, 72, 20, 10000, 880, 787, 727; Arteriosclerosis 10000, 2720, 2170, 1800, 1600, 1500, 880, 787, 776, 727, 20, 808.79; Arthritis, 10000, 1550, 880, 802, 787, 727, 28, 20, 7.7, 3.0, 1.2; Arthritis, rheumatoid of the muscles and tendons 250, 1.2, 1875, 787, 727, 808.79; Arthritis, arthrosis and parathyroid disturbances affecting calcium metabolism, 9.6; Arthritis, arthralgia due to gout, 9.4; Arthritis focal origin 9.4; Asthma, 2720, 2170, 1800, 1600, 1500, 880, 787, 727, 808.79; Astrocytoma 9.2, 8.25, 7.7, 2170, 2127, 880, 690, 666; Ataxia 2720, 2170, 1800, 1600, 1500, 880, 787, 776, 727, 650, 625, 600, 2309, 125, 95, 72, 20, 805.6, 811.91, spastic ataxia, 9.2, 8.25, 7.7; Athlete's Foot 465, 1550, 880, 802, 727, 20, Autoimmune Disorders 10000, 3352, 880, 787, 776, 727, 650, 625, 600, 465, 250, 28, 20, 9.6, 9.4, 7.7, 3.0, 522, 146, 1850; Autointoxication 0.5, 522, 146, 10000, 880, 787, 727, 20, 555, 333, 999; Back pain 26, 186, 3040, 522, 146, 555, 333, 999, 10000, 760, 2352, 880, 787, 727; Bad Breath 2352, 880, 787, 727, 20; Bedsores 880, 2352, 787, 727, 485 followed by 1.2 and 73; Biliousness 2352, 10000, 880, 832, 787, 727, 465; Bladder and prostate complaints 880, 2352, 787, 727, 465, 20, 9.4 Boils 880, 2352, 787, 727, 465, 660, 589, 333; Bone trauma 380, 2352, 10000, 880, 787, 727; Bone/ periodontal disease 47.5, 1800, 1600, 1875, 880, 787, 776, 727; Bone protuberance 1.2 and 250; Brachial Neuralgia 0.5; Breast 880, 2352, 787, 776, 3083; Bright's Syndrome 1500, 880, 787, 727; Bronchial asthma 0.5, 522, 146, 125, 95, 72, 966, 20; Bronchitis 880, 727, 9.4, 9.35; Bronchial Pneumonia 2352, 880, 787, 776, 727; Bubonic Plague 500, plus secondary infections: 880, 787, 727, 20; Burns 190, 10000, 880, 787, 727, 465, 200; Bursitis 880, 787, 727; Cancer 465, 2127, 880, 787, 3083, 589; Cardiac Edema 9.2; Carpal Tunnel Syndrome 1550 thru 465, 6.3, 148, 2.5, 727, 522, 146, 444; Cataract 10000, 880, 787, 727; Catarrh 1550, 802, 880, 787, 727, 444, 20; Cerebral Palsy 880, 787, 727, 522, 146; Chicken Pox 2352, 1800, 1600, 1500, 880, 787, 727, 20; Cholera 880, 802, 450, 880, 787, 727; Chronic Fatigue Syndrome 10000, 2720, 1800, 880, 802, 787, 776, 727, 465, 966, 330, 148, 125, 95, 73, 72, 35, 27.5, 20, 6.3, 4.9, 428, 660; Circulatory stasis 40; Circulation disturbance problems 40,9.4; Concentration 7.83; Cold in head, chest 10,000, 1550, 880, 802, 787, 776, 727, 444, 20; Colic 1550, 832, 802, 787, 727, 20; Colitis 1550, 880, 832, 802, 440; Constipation 1550, 880, 802, 787, 776, 727, 20; Convulsions 10,000, 880, 787, 727; Contusions 9.1, 110; Costalgia 160, 26, 3040, 880, 787, 727, 10,000, 2353; Cramps 10,000, 880, 787, 727, 26; Cystiris (of urinary bladder) 1550, 880, 802, 787, 727, 465, 20; Deafness 10,000, 1550, 880, 802, 787, 727, 20; Dental foci 3040, 95, 190, 47.5, 1600, 1550, 2353, 1500, 880, 832, 787, 776, 760, 727, 1316, 1916, 465, 2720, 2489, 1800, 522, 146, 555, 333, 999; Depression, anxiety, trembling, weakness 3.5; Depression 35, 220, 1.1, 73; Detoxification 6.3, 148, 2.5, 727, 522, 146, 444, 666, 428, 880, 787, 555, 333, 999; Diabetes 837, 260, 1885, 125, 95, 1957, 522, 428, 49.4 for secondary diabetes infections 10,000, 2720, 2170, 1800, 1550, 880, 802, 727, 465, 20; Diabetic loading 35, 700; Diarrhea/Dysentery 1550, 880, 802, 787, 727, 465; Distortion 9.1, 110; Dizziness 5.8; Dupuytren's Contracture 1.2, 250; Dysmenorrhea 26, 4.9, 2352, 880, 787, 727, 465; Dyspepsia 1550, 880, 802, 787, 727; Ears 9.2, 880, 787, 727, 20; Eczema 9.2, 1550, 802, 787, 727; Eczema 9.4; Enuresis 10,000, 880, 787, 727, 465; Edema 522, 146, 154.3, 444, 440, 880, 787, 727, 465; Epicondylitis 251.2, 3040, 160, 26; Epididymitis 1500, 880, 787, 7827, 20; Epilepsy 10,000,.880, 802, 787, 727, 700, 650, 600, 125, 20; Epstein-Bart 428, 660, 776, 465, 880, 787, 727; Erysipelas 660, 2000, 10,000, 880, 787, 727, 465, 20; Erythema nosodum 9.4; Esophagus 880, 787, 727; Eustachian tube inflammation 1550, 880, 802, 787, 776, 727, 465; Eye inflammation 1.2, 80; Eye Disorders 1600, 10,000, 880, 787, 727, 20; Eyes 1600, 880, 787, 727; Facial paralysis 10,000, 880, 787, 727; Fatigue 2720, 1800, 428, 660, 465, 125, 95, 72, 27.5, 20, 2309; Fever 880, 787, 727, 20; Fibroma 2127, 2008, 727, 690, 666, 1550, 802, 465; Fibrosis of lung 457.5; Fistulal Ulcer 880, 832, 787, 727; Flashes, hot (complications) 10,000, 880, 787, 727; Flatulence 1550, 880, 802, 787, 760, 727, 465; Flu 1550, 880, 802, 787, 727, 20; Foot (blisters) 10,000, 880, 787, 727, 600; Fractures 450, 10,000, 880, 787, 727; Frostbite 880, 787, 727; Frozen shoulder 10,000, 880, 802, 787, 727; Fungal infection 465, 1550, 880, 802, 727, 20; Furunkulosis herpes, skin diseases 1200, 1550, 802, 2000, 787, 727; Gall bladder dystonia with osteitis 2.6, 3040, 880, 787, 727, 20; Gallstones 2.65, 3040, 880, 787, 727, 20; Gangrene 880, 787, 727, 20, 73; Gas (intestinal) 1550, 880, 802, 787, 760, 727, 465; Gastritis and flatus 880, 832, 787, 727, 20; Gout 9.4, 3040, 880, 787, 727, 20; Gravel in urine 2.6, 3040, 880, 787, 727, 20; Gums (inflammation, gingivitis, pyorrhea) 1550, 880, 802, 787, 727, 465, 20; Hair loss 10,000, 880, 787, 727, 465, 146; Hallucinations 10,000, 880, 787, 727, 20; Hangover 10,000, 146, 610; Hay Fever 880, 787, 727, 20; Headaches 160, 10, 6.3, 522, 146, 4.9, 3040, 727, 148, 125, 95, 72, 20, 10, 5.8, 2.5, 444, 685, 880, 787, 650, 625, 600, 3040, 428, 660, 555, 333, 999; For headaches caused by parasites 160, 125, 95, 73, 20, 727, 3040; Headaches (urogenitaiiy caused) 160, 9.4, 3040, 555, 333, 999, 160, 9.6, 3040; Head Injuries 160, 9.6, 3040, 880, 787, 727, 522, 72, 5.8, 4.9; Hearing problems 10,000, 2158, 880, 787, 760, 727, 20; Heart (lab animals only) 80, 160, 20, 73, 3.9, 10,000, 880, 787, 727, 465, 4125 95, 20; Heartburn 832, 2720, 2170, 2127, 1800, 1600, 2352, 1500, 880, 787, 727, 685, 465, 2309, 125, 95, 72, 20; Hemorrhage 1550, 802; Hemorrhoids 1550, 880, 802, 727; Hepatitis (generic)29.2, 1550, 880, 802, 727; Hernia 10,000, 787, 727; Herpes (zoster) 2720, 2170, 1800, 1600, 1500, 1550, 802, 1865,880, 787, 727, 20; High blood pressure 10,000, 880, 787, 727, 9.2; Hip Pain (as in coxarthritis) 3040, 880, 787, 727, 160, 26; Hives 1800, 880, 787, 727, 522, 146, 4.9; Hoarseness 880, 760, 727; Hyperacidity of stomach 7.83 on solar plexus and 230 on stomach; Hydrocele 880, 787, 727; Hyperosmia 20, 10,000, 522, 1865, 810.35; Hyperthyroid 3.0, 0.5; Hypoacidity of stomach 15, 20; Hypothyroid 12, 35; Hypertension 20, 95, 9.2, 6.0, 10,000, 880, 787, 727; Hypertension, spastic 95; Impotence 9.4, 2127, 2008, 465, 880, 802, 787, 2083, 125, 95, 73, 72, 20, 1875; Indigestion 10,000, 880, 787, 727, 465, 444, 20, 125, 95, 72, 4.9; Infantile Paralysis 1500, 880, 787, 727; Infections 1600, 1550, 1500, 880, 832, 802, 787, 776, 760, 727, 700, 690, 666, 630, 623, 600, 465, 444, 123, 95, 72, 20, 1865, 300, 430, 440, 428, 660; Infertility 2127, 2008, 465, 880, 802, 787, 2083, 1873, 9.4; Inflammation 1.5; Influenza 1550, 802, 1500, 880, 787, 727, 20; Insomnia 3.6, 3.0, 1530, 1300, 880, 802; Intercostal neuralgia 3040, 160, 26, 1550, 880, 802, 787, 776, 727, 125, 20, 1865, 444; Intermittent claudication 45, 48; Itching 880, 787, 727, 465, 444, 125, 95, 72, 7.83, 2309, 2000; Jaundice 1600, 1550, 1500, 880, 802, 650, 625, 600, 2309, 146, 250, 125, 93, 72, 20; Kidney insufficiency 50, 440, 1600, 1550, 1500, 880, 802, 787, 727, 650, 625, 600, 465, 73, 40, 10, 2309, 522, 446, 250, 148, 125, 95, 72, 20, 555, 333, 999; Knee/joint pain 3040, 160, 26, 1550, 880, 802, 787, 727, 28, 20, 7.7, 3.0, 1.2, 250, 1.2, 9.6, 9.4; Larynx 440, 465, 444, 1550, 880, 802, 787, 727, 28, 7.7, 3.0, 1.2, 250, 1.2, 9.6, 9.4; Leprosy 600, 1600, 1550, 1500, 880, 832, 802, 787, 776, 760, 727, 700, 690, 666, 650, 625, 600, 465, 444, 20, 500, 450, 440, 428, 660; Leukemia 2127, 2008, 880, 787, 727, 690, 666, 589; Leukoderma 880, 787, 727, 444, 20, 589, 2000; Locomotor Dysfunction 10,000, 880, 787, 776, 727, 650, 625, 600, 2309, 125, 95, 72, 20; convulsions, spasticity 28, 8.25, 7.7; Low Blood Pressure 880, 787, 727, 20; Lumbago 10,000, 880, 787, 727, 125, 95, 72, 2309, 9.2, 8.25, 7.7.; Lungs 1550, 802, 880, 787, 776, 727, 125, 95, 72, 20, 2309, 450, 589; Lupus Erythematosus 880, 787, 727, 776, 1850; Luxation 119.1; Lymph stasis 154.3, 2.5, 727, 522, 146, 444, 428, 880, 787; Malaria 555; Measles 333; Mental Disorders 444, 148, 20, 6.3, 2.5, 522, 146, 10,000, 125, 95, 72, 4.9, 727, 428, 444, 465 to 1550; Menieres Disease 2352, 880, 787, 727, 465, 428, 589, 333; Meningitis 2352, 880, 832, 787, 727, 650, 625, 600, 465, 2309, 125, 95, 72, 20, 428, 660; Menstrual problems 26, 3040, 880, 787, 727, 465, 160, 20; Migraine 170; Motion Sickness 650, 625, 600, 465, 444, 1865, 522, 146, 125, 95, 72, 20; Mouth eruptions 465, 2127, 2008, 727, 690, 666; Herpes sores 2489, 1800, 465, 1550, 1500, 880, 787, 727, 1850, 428; Mucous membrane inflammation 380; Multiple Sclerosis use auto immune frequencies plus 880, 787, 727; Muscles, to relax 760, 6.85 Muscular Dystrophy 10,000, 2352, 880, 787, 776, 727, 650, 625, 600, 465, 250, 28, 20, 9.6, 9.4, 7.7, 3.0, 522, 610, 1850, 146, 555, 333, 999; Muscular pain 3040, 26, 160, 320, 250, 240, 80, 40, 10, 5.8, 2.5, 1.5, 1.2, 1.0, 0.5; Muscle pain from parasites 2309, 125, 811, 108, 72, 20; Mumps 10,000, 727, 2720, 2489, 2127, 2008, 14, 428, 880, 787, 727, 20; Nausea 880, 832, 787, 727, 20, 4.9; Nephritis\nephrosis 880, 787, 727, 10, 40, 73, 465; Nervousness 3.0; Nerve disorders 10,000, 2720, 2489, 2170, 1800, 1600, 2352, 880, 787, 148, 6.3, 2.5, 522, 610, 727, 650, 625, 600, 125, 95, 72, 20, 428, 660, 333; Neuralgia 3.9, 555, 333, 999; Neurosis 28; Nose infection, congestion 2352, 880, 787, 776, 727, 444, 440, 465, 20; Numbness 10,000, 2720, 2489, 2170, 1800, 1600, 2352, 880, 787, 727, 650, 625, 600, 440, 660, 333; Oral Lesions 2720, 2489, 2008, 1800, 1600, 2352, 880, 787, 776, 760, 727, 465, 444, 522, 146, 555, 333, 999; Orchitis 2720, 2489, 2127, 2008, 1800, 1600, 2352, 1500, 880, 832, 787, 776, 2083; 650, 625, 600, 125, 95, 72, 20, 14; Osteomyelitis 2.6, 2720, 2489, 2170, 2127, 2008, 1800, 1600, 2352, 1500, 880, 832, 787, 776, 2083; Otosclerosis 9.2; Ovarian disorders 1875, 465, 444, 26, 2720, 2489, 2170, 2127, 2008, 1800, 1600, 2352, 1500, 880, 832, 787, 776, 2083, 20; Pain 3040, 95, 160, 26; Pain of infection 3040, 160, 26, 95, 880, 2352, 787, 776, 727, 4.9; Pain of cancer 3040, 160, 26, 95, 2127, 2008, 2083; Pancreatic insufficiency 15, 10, 250, 1875, 465, 444, 26, 2720, 2489, 2170, 2127, 2008, 1800, 1600, 2352, 1500, 880, 832, 787, 776, 2083, 20; Paralysis, spastic 10,000, 880, 787, 776, 727, 650, 625, 600, 2309, 125, 95, 72, 20, 7.7; Paralysis, nonspastic 10,000, 880, 787, 776, 727, 650, 625, 600, 444, 1865, 125, 95, 72, 20, 9.2, 8.25; Parasites 125, 95, 72, 20, 2309; Pelvic Inflammatory Disease 2720, 2489, 2170, 2127, 2008, 1800, 1600, 2352, 787, 776, 2083, 650, 625, 600, 465, 966, 95, 72, 450, 428, 14, 589, 1570; Pericarditis 2720, 2170, 1600, 880, 2352, 787, 760, 727, 625, 465, 160, 125, 73, 26, 20, 3.9, 95, 80, 73, 72, 2309; Pharyngitis 440, 589, 380, 1600, 2352, 776, 787, 880, 727, 20, 522, 146; Pleurisy 1550, 802., 880, 787, 776, 727, 125, 95, 72, 20, 2309, 450, 589; Pneumonia 1550, 802, 880, 787, 776, 727, 20, 450, 589; Poliomyelitis 805.6 secondary complications 2158, 428, 1500, 880, 787, 727; Polyps 2720, 2489, 2170, 2127, 2008, 1800, 1600, 2083, 1875, 465, 444, 20, 522, 146; Pre-op and post-operation prevention and control of nosocomial and idiopathic infection 2170, 1800, 1600, 2352, 1500, 880, 832, 802, 787, 776, 727, 465, 444, 522, 146, 428, 589, 333; Prostatitis 510, 522, 146, 2720, 2489, 2170, 2127, 2008, 2352, 787, 776, 2083, 465, 125, 95, 72, 20, 1249; Prostate complaints 9.4, 2127, 2008, 727, 690, 666, 465, 880, 802, 787, 727, 125, 95, 73, 72, 20; Proritis 880, 787, 727, 465, 444, 125, 95, 72, 20, 2309, 2000; Prostate tumor (malignant) 2127, 2008, 2083; Psychosomatic pain 727, 160, 26, 148, 455, 511, 146, 555, 333, 999; Pyorrhea 2720, 2489, 2008, 1800, 1600, 2352, 880, 787, 776, 727, 465, 444, 522, 146; Rabies 807.23; Raynaud's Disease 727, 20; Rheumatoid arthritis of the muscles and tendons 251.2, 9.6, 9.4, 1875, 10,000, 2352, 880, 787, 727, 465, 20, 7.7, 3.0, 1.2; Rhinitis 10,000, 2352, 1500, 880, 787, 776, 727, 444, 7.83, 522, 146, 465; Sarcoma 2127, 2008, 880, 787, 727, 690, 666, 589; Scars 465 to 1568; Scarlet Fever 880, 787, 727, 1356; Sciatica or Ischia 2352, 880, 787, 727, 690, 666, 10; Sedative Effect 2.5; Sexual Dysfunction 9.4, 2127 2008, 465, 880, 802, 787, 2083, 125, 95, 73, 72, 20, 1875; Shingles 2352, 802, 1800, 1865, 1880, 787, 727, 26; Sinusitis 2352, 880, 787, 727, 125, 72, 522; Sleeping Sickness 124; Slipped discs 26, 125, 880, 787, 333, 787, 727, 95, 72, 522, 146, 555, 333, 999; Smallpox 811.91, 1550, 802, 880, 787, 727; Sneezing 880, 787, 727, 465, 146; Sore Throat 2720, 2489, 1800, 1600, 2352, 880, 787, 776, 727, 465, 589, 808.79; Spasms, muscle 6.8; Spastic paresis 650, 625, 30.87,48; Spleen, enlarged 35, 787, 10,000, 2720, 2170, 1800, 1550, 880, 802, 727, 465, 20; Spondylitis, acute 1.2, 10, 7.7, 28; Staphylococci infection 727; Stiff neck 4.9; Spastic stiff neck 9.2, 6.0; Stiff muscles in general 320, 250, 240, 160, 125, 80, 40, 20, 10, 5.8, 2.5, 1.5, 1.2, 1.0, 0.5, 1800, 2352, 880, 787, 776, 727; Stomach disorders 2127, 2008, 880, 787, 727, 2083, 125, 95, 72, 20, 3.9, 450, 1570, 1770; Stones 3.5; Streptococci infection 880; Streptothrix infection 787; Sty 10,000, 880, 787, 727, 20; Subluxation induced disorders 9.6; Sun Allergy 3.0, 330; Sunstroke 444, 428, 190, 3040, 95, 522, 146, 880, 20; Surgery—Prevention and control of nosocomial and idiopathic infection 2170, 1800 1600, 2352, 1500, 880, 832, 802, 787, 776, 727, 465, 444, 522, 146, 428, 589, 333, 3040, 95, 160, 26, 544; Swelling 522, 146, 6.3, 148, 444, 428, 95, 880, 787, 727; Swollen glands 880, 787, 727, 20; Syphilis 1875; Tachycardia (also used for pain of arthritis, headache, Tui-na, and facial toning) 1.2; Teeth 3040, 95, 190, 47.5, 1600, 2352, 1500, 880, 10,000, 2489, 787, 776, 760, 727, 1875, 465, 2720, 2489, 1800; Tendo myopathy 3040, 320, 250, 160, 80, 40, 26, 20, 10, 5.8, 2.5, 1.5, 1.2, 1.0, 0.5, 522, 146; Tetanus 811.91, 600, 880, 787, 727; Thrush 465; Tonsillitis 74.2, 73, 2352, 1500, 880, 832, 787, 776, 727, 1875, 465, 808.79, 589; Toothache 3040, 95, 190, 47.5, 2720, 2489, 1800, 1600, 2352, 1500, 880, 832, 787, 776, 727, 666, 650, 600, 465, 522, 146, 555, 333, 999; Tooth extraction, afterward 3040, 95, 47.5, 7.83; Toxins 444, 160, 522, 146, 555, 333, 999, 10,000, 880, 787, 727, 125, 95, 72, 20; Trauma 3040, 95, 190, 760, 880, 787, 727, 465; Trench Mouth 1875, 880, 787, 776, 727, 650, 625, 465; Trigeminal neuralgia 2720, 2489, 2170, 1800, 1600, 2352, 880, 832, 787, 776, 760, 727, 650, 146, 7.83, 27.5, 428, 660, 589, 333, 999, 770, 2000, 805.6, 807.23, 811.91, 810.35; Tuberculosis 2352, 1875, 776, 2127, 2008, 465, 589; Typhoid 1570, 1770, 2352, 690, 1800; Ulcers 2489, 2170, 2127, 1800, 1600, 880, 832, 802, 787, 776, 727, 1.2 through 5.8, 1.2, 73; Urethritis 2720, 2170, 2127, 1800, 1600, 2352, 1500, 880, 832, 787, 776, 727, 1875, 455, 2309, 125, 95, 72, 1.2; Urticaria 1800, 444, 125, 95, 72, 522, 146, 787, 727, 6.3; Varicoses 1.2, 28; Vegetative Dystonia 40; Vein thrombosis 685; Vertigo 60, 5.8; Warts 3040, 5, 2170, 2127, 2008, 1800, 1600, 1500, 2083; Worms 125, 95, 6.0, 20, 2309; Wound healing 880, 787, 727, 220, 190, 20, 40; Yeast infection 465; Yellow Fever 999; Scan brain for troubled areas 7.83; For relaxation 4.9; To stimulate mental clarity 12; Facial toning 9.6; Kidney meridian 9.2.

* * * * *